United States Patent
Bromley

(10) Patent No.: US 11,491,194 B2
(45) Date of Patent: Nov. 8, 2022

(54) STABLE DRY POWDERS AND EMULSIONS CONTAINING PROBIOTICS

(71) Applicant: Virun, Inc., Pomona, CA (US)

(72) Inventor: Philip J. Bromley, Fullerton, CA (US)

(73) Assignee: Virun, Inc., Pomona, CA (US)

( * ) Notice: Subject to any disclaimer, the term of this patent is extended or adjusted under 35 U.S.C. 154(b) by 151 days.

(21) Appl. No.: 16/569,580

(22) Filed: Sep. 12, 2019

(65) Prior Publication Data

US 2020/0000860 A1    Jan. 2, 2020

Related U.S. Application Data

(63) Continuation of application No. PCT/US2017/051923, filed on Sep. 15, 2017.

(60) Provisional application No. 62/475,803, filed on Mar. 23, 2017.

(51) Int. Cl.
| | |
|---|---|
| A61K 35/747 | (2015.01) |
| A23L 33/12 | (2016.01) |
| A23L 33/17 | (2016.01) |
| A23L 33/135 | (2016.01) |
| A23P 10/40 | (2016.01) |
| A61K 9/06 | (2006.01) |
| A61K 9/107 | (2006.01) |
| A61K 9/14 | (2006.01) |
| A61K 47/10 | (2017.01) |
| A61K 47/12 | (2006.01) |
| A61K 47/14 | (2017.01) |
| A61K 47/26 | (2006.01) |
| A61K 47/42 | (2017.01) |
| A61K 9/00 | (2006.01) |

(52) U.S. Cl.
CPC ............ *A61K 35/747* (2013.01); *A23L 33/12* (2016.08); *A23L 33/135* (2016.08); *A23L 33/17* (2016.08); *A23P 10/40* (2016.08); *A61K 9/006* (2013.01); *A61K 9/107* (2013.01); *A61K 9/14* (2013.01); *A61K 47/10* (2013.01); *A61K 47/12* (2013.01); *A61K 47/14* (2013.01); *A61K 47/26* (2013.01); *A61K 47/42* (2013.01); *A23V 2002/00* (2013.01); *A23Y 2220/03* (2013.01); *A23Y 2220/73* (2013.01); *A23Y 2300/45* (2013.01); *A23Y 2300/49* (2013.01); *A23Y 2300/55* (2013.01)

(58) Field of Classification Search
CPC ............... A23L 33/12; A61K 35/747
See application file for complete search history.

(56) References Cited

U.S. PATENT DOCUMENTS

| | | | |
|---|---|---|---|
| 3,480,616 A | 11/1969 | Osipow et al. | 536/119 |
| 3,644,333 A | 2/1972 | Osipow et al. | 536/119 |
| 3,714,144 A | 1/1973 | Feuge et al. | 536/119 |
| 4,353,365 A | 10/1982 | Hallworth et al. | 128/203.15 |
| 4,524,769 A | 6/1985 | Wetterlin et al. | 128/203.15 |
| 4,710,567 A | 12/1987 | Kea et al. | 536/119 |
| 4,898,935 A | 2/1990 | Nakamura et al. | 536/119 |
| 4,995,911 A | 2/1991 | Matsumoto et al. | 127/48 |
| 4,996,309 A | 2/1991 | Matsumoto et al. | 536/119 |
| 5,011,922 A | 4/1991 | Matsumoto et al. | 536/119 |
| 5,017,697 A | 5/1991 | Matsumoto et al. | 536/127 |
| 5,033,252 A | 7/1991 | Carter | 534/25 |
| 5,035,237 A | 7/1991 | Newell et al. | 128/203.15 |
| 5,052,558 A | 10/1991 | Carter | 206/439 |
| 5,239,993 A | 8/1993 | Evans et al. | 128/203.15 |
| 5,323,907 A | 6/1994 | Kalvelage | 206/531 |
| 5,415,162 A | 5/1995 | Caspser et al. | 128/203.12 |
| 5,430,021 A | 7/1995 | Rudnic et al. | 514/10.1 |
| 5,715,810 A | 2/1998 | Armstrong et al. | 128/230.15 |
| 6,265,717 B1 | 7/2001 | Sakata et al. | 250/289 |
| 6,378,519 B1 | 4/2002 | Davies et al. | 128/203.21 |
| 6,475,511 B2 | 11/2002 | Gohlke et al. | 424/441 |
| 6,534,085 B1 | 3/2003 | Zeligs | 424/451 |
| 7,906,140 B2 | 3/2011 | Bromley et al. | 424/450 |
| 8,252,323 B2 | 8/2012 | Bromley | 424/450 |
| 8,282,977 B2 | 10/2012 | Bromley | 426/72 |
| 8,414,914 B2 | 4/2013 | Bromley et al. | 424/450 |
| 8,722,131 B2 | 5/2014 | Tang et al. | 426/604 |
| 9,320,295 B2 | 4/2016 | Bromley | 424/94.1 |
| 9,345,743 B2 | 5/2016 | Oda et al. | 530/300 |
| 9,549,984 B2 | 1/2017 | Weinrich et al. | |
| 9,788,564 B2 | 10/2017 | Bromley | 514/1 |
| 9,861,611 B2 | 1/2018 | Bromley | 424/456 |
| 10,016,363 B2 | 7/2018 | Bromley | 424/439 |
| 10,213,490 B2 | 2/2019 | Bromley et al. | 424/450 |
| 10,220,007 B2 | 3/2019 | Bromley | 426/602 |
| 10,285,971 B2 | 5/2019 | Bromley | 424/456 |
| 10,335,385 B2 | 7/2019 | Bromley et al. | 426/602 |

(Continued)

FOREIGN PATENT DOCUMENTS

| | | |
|---|---|---|
| CN | 103566376 A | 2/2014 |
| JP | H07-267866 A | 10/1995 |
| WO | WO 2007/082149 | 7/2007 |
| WO | WO 2016/032000 | 3/2016 |

(Continued)

OTHER PUBLICATIONS

Innerbio Formula XP-002776260 As cited in applicants IDS (Year: 2004).*

(Continued)

*Primary Examiner* — Louise W Humphrey
*Assistant Examiner* — Trevor L Kane
(74) *Attorney, Agent, or Firm* — Dentons US LLP; Stephanie Seidman

(57) ABSTRACT

Compositions and methods for mucosal delivery of agents are provided. The emulsion compositions are intended for administration to a mucosal surface, such as oral, gastrointestinal and nasal mucosa. The emulsion compositions provided contain one or more mucoadhesive proteins and an agent to be delivered. Methods for delivery of agents using the compositions provided herein are also provided.

16 Claims, No Drawings

(56) References Cited

U.S. PATENT DOCUMENTS

| | | | |
|---|---|---|---|
| 2005/0196440 A1 | 9/2005 | Masters et al. | 424/464 |
| 2005/0197495 A1 | 9/2005 | Naidu | 530/400 |
| 2006/0093594 A1 | 5/2006 | Naidu | 424/93.45 |
| 2007/0184117 A1 | 8/2007 | Gregory et al. | 424/489 |
| 2009/0297491 A1 | 12/2009 | Bromley | 424/94.1 |
| 2009/0297665 A1 | 12/2009 | Bromley | 426/72 |
| 2011/0117184 A1 | 5/2011 | Bromley | 424/450 |
| 2011/0236364 A1* | 9/2011 | Bromley | A23L 33/12 424/94.1 |
| 2012/0016026 A1 | 1/2012 | Bromley | 514/560 |
| 2014/0271593 A1 | 9/2014 | Bromley | 424/94.1 |
| 2016/0081927 A1 | 3/2016 | Bromley | 424/439 |
| 2016/0193146 A1 | 7/2016 | Bromley | 424/94.1 |
| 2016/0227832 A1 | 8/2016 | Bromley | 424/94.1 |
| 2017/0273326 A1 | 9/2017 | Tsubota et al. | 424/93.4 |
| 2018/0042865 A1 | 2/2018 | Bromley | 426/72 |

FOREIGN PATENT DOCUMENTS

| | | |
|---|---|---|
| WO | WO 2016/044813 | 3/2016 |
| WO | WO 2017/049162 | 3/2017 |

OTHER PUBLICATIONS

Lim JH, Yoon SM, Tan PL, Yang S, Kim SH, Park HJ. Probiotic Properties of Lactobacillus Plantarum LRCC5193, a Plant-Origin Lactic Acid Bacterium Isolated from Kimchi and Its Use in Chocolates. J Food Sci. Nov. 2018;83(11):2802-2811. doi: 10.1111/1750-3841.14364. Epub Oct. 16, 2018. PMID: 30325520. (Year: 2018).*
Griffiths, E.A., Duffy, L.C., Schanbacher, F.L. et al. In Vitro Growth Responses of Bifidobacteria and Enteropathogens to Bovine and Human Lactoferrin. Dig Dis Sci 48, 1324-1332 (2003). https://doi.org/10.1023/A:1024111310345 (Year: 2003).*
Letter/Written Disclosure of the Information Disclosure Statement for the above-referenced application, filed herewith on Oct. 18, 2019, 2 pages.
Analytical Chemistry An Introduction 6$^{th}$ Ed., Douglas A. Skoog et al., Chapters 22, "Applications of molecular absorption spectroscopy," (pp. 421-442) and 27, "Applications of chromatography," (pp. 509-530) (1994).
Azuma et al., "Bifidus Growth-promoting Activity of a Glycomacropeptide Derived from Human κ-Casein," Agric. Biol. Chem. 48:2159-2162 (1984).
Bailey et al., "Identification and Characterisation of an Iron-Responsive Candidate Probiotic," PLoS One 6(10):e26507 (2011), 10 pages.
Bevnet website, "Virun Releases Episode 2 of Probiotic and Omega Supplement Video Series," published on Feb. 13, 2017 [online], Retrieved from <URL:bevnet.com/news/2017/virun-releases-episode-2-probiotic-omega-supplement-video-series [retrieved onFeb. 13, 2017], 2 pages.
"CRC Handbook of Chemistry and Physics," Lide, D., ed., 82$^{nd}$ Edition, Cleveland, OH:CRC Press 15(14)-15(18) (2001).
Daniells, S., "Virun develops shelf-stable, non-refrigerate probiotic powders, emulsions," published onNov. 16, 2016, Retrieved from: <URL:www.nutraingredients-usa.com/Article/2016/11/16/Virun-develops-self-stable-non-refrigerate-probiotic-powders-emulsions [retrieved on Nov. 20, 2017], 1 page.
Database GNPD [online] Mintel; Annonymous: "Innerbio-Formula," XP002776260, Retrieved from: <URL:www.gnpd.com, Database Accession No. 281180, 2 pages.
Degnan, F.H., "The US Food and Drug Administration and Probiotics: Regulatory Categorization," Clin. Infect. Dis. 46 (Supplement 2):S133-S136 (2008).
Deschemin et al.,"The microbiota shifts the iron sensing of intestinal cells," FASEB J. 30(1):252-261 (2015).
Dionysius, D.A. and J.M. Milne, "Antibacterial Peptides of Bovine Lactoferrin: Purification and Characterization," J. Dairy Sci. 80(4):667-674 (1997).
Ferdousi et al., "Evaluation of Probiotic Survivability in Yogurt Exposed To Cold Chain Interruption," Iran. J. Pharm. Res. 12(Suppl):139-144 (2013).
Gale, K., "Probiotic May Block HIV from Breast Milk," Reuters Health, Published May 25, 2004 [online], Retrieved on Oct. 26, 2018 from <URL: web.archive.org/web/20071208202224/http://www.pronutrition.org:80/archive/200406/msg00002.php, 2 pages.
Giddings et al., "High pressure gas chromatography of nonvolatile species. Compressed gas is used to cause migration of intractable solutes," Science 162:67-73 (1968).
Good, R.J., "Surface free energy of solids and liquids: Thermodynamics, molecular forces, and structure," Journal of Colloid and Interface Science 59(3):398-419 (1977).
Griffin, W.C., "Classification of surface-active agents by HLB," J. Soc. Cosmet. Chem. 1:311-326 (1949).
Gutmann, V., "Solvent effects on the reactivities of organometallic compounds," Coord. Chem. Rev. 18:225-255 (1976).
Iravani et al., "Technology and potential applications of probiotic encapsulation in fermented milk products," J. Food Sci. Technol. 52(8):4679-4696 (2015).
Kosower, E.M., "2.6 Solvent polarity: Empirical Measures," in: An Introduction to Physical Organic Chemistry, New York: Wiley, p. 293 (1969), 2 pages.
Liepke et al., "Human milk provides peptides highly stimulating the growth of bifidobacteria," Eur. J. Biochem. 269:712-718 (2002).
Lowery et al., "2.4 Solutions," in: Mechanism and Theory in Organic Chemistry, Harper Collins Publishers, 3$^{rd}$ Edition, p. 177 (1987).
Machine-generated English translation of Chinese Patent Publication No. CN103566376 (A), published Feb. 12, 2014, accessed from Espacenet on Oct. 9, 2019, 15 pages.
Machine-generated English translation of Japanese Patent Publication No. H07-267866 (A), published on Oct. 17, 1995, accessed from <URL:j-platpat.inpit.go.jp on Oct. 8, 2019, 8 pages.
Masco et al., "Polyphasic taxonomic analysis of *Bifidobacterium animalis* and *Bifidobacterium lactis* reveals relatedness at the subspecies level: reclassification of *Bifidobacterium animalis* as *Bifidobacterium animalis* subsp. *animalis* subsp. nov. and *Bifidobacterium lactis* as *Bifidobacterium animalis* subsp. *lactis* subsp. nov.," Int. J. Syst. Evol. Microbiol. 54(Pt 4):1137-1143 (2004).
Mitropoulou et al., "Immobilization Technologies in Probiotic Food Production," J. Nutr. Metab. 2013:716861 (2013), 15 pages.
Mitsuoka, T., "Human Microbiota Research-Present and Future," Journal of Intestinal Microbiology, 19:179-192 (2005) [In Japanese with an English language abstract].
Muthu et al., "Theranostic vitamin E TPGS micelles of transferrin conjugation for targeted co-delivery of docetaxel and ultra bright gold nanoclusters," Biomaterials 39:234-248 (2015).
NUTRAingredients-Usa, "Virun develops shelf-stable, non-refrigerate probiotic powders, emulsions," published on Nov. 16, 2016 [online], Retrieved from <URL: nutraingredients-usa.com/Suppliers2/Virun-develops-shelf-stable-non-refrigerate-probiotic-powders-emulsions [retrieved on Feb. 13, 2017], 2 pages.
Nutritional Outlook, "Virun Unveils New Shelf-Stable Probiotic Powders, Emulsions," published on Nov. 17, 2016 [online], Retrieved from <URL:nutritionaloutlook.com/digestive-health/virun-unveils-new-shelf-stable-probiotic-powders-emulsions [retrieved on Feb. 13, 2017], 2 pages.
Okamoto et al., "Effect of Sucrose Fatty Acid Esters on Transdermal Permeation of Lidocaine and Ketoprofen," Biol. Pharm. Bull. 28(9):1689-1694 (2005).
Perry, R. and D. Green, "Perry's Chemical Engineers' Handbook," 6$^{th}$ Edition, New York:McGraw-Hill, pp. 20-54 to 20-57 (1984), 5 pages.
Press Release, "VIRUN Patent Granted Mucosal Adhesive Penetrating Technology Delivering Naive Compounds and Peptides Orally," published on Mar. 23, 2011, Retrieved from <URL:pr.com/press-release/307987, 2 pages.
Press Release, "VIRUN® Launches a Line of Shelf-Stable Probiotic Multi-Serving Powders and Emulsions," published onNov. 15, 2016 [online], Retrieved from <URL:pr.com/press-release/695282 [retrieved on Nov. 22, 2016], 3 pages.

(56) References Cited

OTHER PUBLICATIONS

Press Release, "VIRUN® Releases STATIC™ Episode 2 While Under the Influence of Sulfur Hexaflouride, and New Probiotic Technology Makes Wholefoods Take Notice," published on Feb. 14, 2017 [online], Retrieved from <URL:pr.com/press-release/705384 [retrieved on Mar. 15, 2017], 3 pages.

Rahman et al., "Screening of *Bifidobacterium* spp. based on in vitro growth responses to bovine lactoferrin," Int. J. Food Sci. Technol. 45(3):453-458 (2010) [Abstract only].

Saarela et al., "Improving the storage stability of *Bifidobacterium breve* in low pH fruit juice," Int. J. Food Microbiol. 149(1):106-110 (2011).

Shah et al., "Improving the Stability of Probiotic Bacteria in Model Fruit Juices Using Vitamins and Antioxidants," J. Food Sci. 75(5):M278-M282 (2010).

Sherman et al., "Neonatal small bowel epithelia: enhancing antibacterial defense with lactoferrin and *Lactobacillus* GG," Biometals 17(3):285-289 (2004).

Smart et al., "An in-vitro investigation of mucosa-adhesive materials for use in controlled drug delivery," J. Pharm. Pharmacol. 36:295-299 (1984).

Smart et al., "In vitro techniques for measuring mucoadhesion," J. Pharm. Pharmacol. 34:70P (1982).

Snyder, L.R., "Classification of the solvent properties of common liquids," J. Chromatography 92:223-230 (1974).

Sreeja, V. and J.B. Prajapati, "Probiotic Formulations: Application and Status as Pharmaceuticals—A Review," Probiotics and Antimicro. Prot. 5(2):81-91 (2013).

Tabor D., "Surface forces and surface interactions," Journal of Colloid and Interface Science 58(1):2-13 (1977).

Tian et al., "Influence of bovine lactoferrin on selected probiotic bacteria and intestinal pathogens," Biometals 23(3):593-596 (2010).

VIRUN News, "Probiferrin Debuts at Ingredient Marketplace, New Website for Virun, and STATIC 3 Underway," email newsletter received on May 2, 2017, 5 pages.

Virun STATIC blog, "Three Separations of Product Brands and Distribution from a Developer," published on Nov. 8, 2016 [online], Retrieved from <URL:virun.com/blog [retrieved on Nov. 22, 2016], 2 pages.

Virun STATIC blog, "Not all Probiotics are Created Equal—How Industry is Fooling the Consumer," published on Mar. 22, 2017 [online], Retrieved from <URL:virun.com/blog [retrieved on Mar. 24, 2017], 5 pages.

Virun STATIC Episode 2 Transcript, "Under the Influence," published on Feb. 7, 2017, Retrieved from <URL:youtube.com/watch?v=VvrhuZNUD-8, 6 pages.

Youan et al., "Evaluation of Sucrose Esters as Alternative Surfactants in Microencapsulation of Proteins by the Solvent Evaporation Method," AAPS PharmSci. 5(2):E22 (2003), 9 pages.

International Search Report and Written Opinion, dated Mar. 8, 2017, in connection with International Patent Application No. PCT/US2016/052256, 19 pages.

Response, filed Jul. 18, 2017, to International Search Report and Written Opinion, dated Mar. 8, 2017, in connection with International Patent Application No. PCT/US2016/052256, 33 pages.

Written Opinion, dated Aug. 30, 2017, in connection with International Patent Application No. PCT/US2016/052256, 6 pages.

Response, filed Oct. 27, 2017, to Written Opinion, dated Aug. 30, 2017, in connection with International Patent Application No. PCT/US2016/052256, 40 pages.

International Search Report and Written Opinion, dated Dec. 20, 2017, in connection with corresponding International Patent Application No. PCT/US2017/051923, 13 pages.

International Preliminary Report on Patentability, dated Jan. 19, 2018, in connection with International Patent Application No. PCT/US2016/052256, 8 pages.

Examination Report, dated Apr. 16, 2018, in connection with United Kingdom Patent Application No. GB 1804800.9, 4 pages.

Response, filed Jun. 14, 2018, to Examination Report, dated Apr. 16, 2018, in connection with United Kingdom Patent Application No. 1804800.9 [D2=CN 103566376], 9 pages.

Office Action, dated Jul. 25, 2018, in connection with U.S. Appl. No. 15/461,389, 10 pages.

Response, filed Aug. 22, 2018, to Office Action, dated Jul. 25, 2018, in connection with U.S. Appl. No. 15/461,389, 6 pages.

International Preliminary Report on Patentability, dated Oct. 3, 2019, in connection with corresponding International Patent Application No. PCT/US2017/051923, 8 pages.

* cited by examiner

STABLE DRY POWDERS AND EMULSIONS CONTAINING PROBIOTICS

RELATED APPLICATIONS

This application is a continuation of International PCT Application No. PCT/US17/51923, filed on Sep. 15, 2017, to inventor Philip J. Bromley and to applicant Virun Inc., entitled "STABLE DRY POWDERS AND EMULSIONS CONTAINING PROBIOTICS," which claims priority to U.S. provisional application Ser. No. 62/475,803, filed Mar. 23, 2017, entitled "STABLE DRY POWDERS AND EMULSIONS CONTAINING PROBIOTICS," to Philip J. Bromley and applicant Virun, Inc. Benefit of priority also is claimed to U.S. provisional application Ser. No. 62/475,803, filed Mar. 23, 2017, entitled "STABLE DRY POWDERS AND EMULSIONS CONTAINING PROBIOTICS," to inventor Philip J. Bromley, and applicant Virun, Inc. The subject matter of each of these applications is incorporated by reference in their entirety.

FIELD

Provided are shelf-stable emulsions and powders that contain probiotics.

BACKGROUND

The use of probiotics for human and animal health is increasing, as is the demand for products that provide effective amounts of probiotics. Probiotics, not only must be safe, they must be provided in a sufficient amount to be effective and in a form that is a live microorganism that can colonize its targeted locus. Generally, such concentration is at least $10^6$ viable cells (colony forming unit, CFU) per gram of the product. It is challenging to produce products in which the probiotics have a reasonably long shelf life, and particularly in a form that does not require refrigeration. Generally probiotics are provided in capsules or yogurts, which are refrigerated. There is a need to develop products that provide high concentrations of probiotics in a viable form that are effective when administered. It is an object herein to do so.

SUMMARY

Shelf-stable multi-serving powders and emulsions that contain mucoadhesive proteins and probiotics are provided. The emulsions further contain a suitable ingestible or consumable oil and an ingestible or consumable polar protic solvent. Additional ingredients include surfactants (other than a polyalkylene glycol- or PEG-derivative of vitamin E), such as a sucrose fatty acid ester (SFAE) surfactant, a binder, such as a dextrin or maltodextrin, and a stabilizer, such as a carbonate, such $KHCO$, or a bicarbonate and/or ascorbic acid, and, optionally, emulsifiers, optional preservatives that do not affect the viability of the probiotic microorganism, co-solvents and other such ingredients. The emulsions and powders optionally include flavoring to render them palatable. The pH of the emulsions can be adjusted as appropriate, such as with a citric acid or other ingestible acid, and typically is about neutral or slightly basic, such as between about 6 and about 8 to 8.5, particularly, about or at 7 to 8, at room temperature, or equivalent conditions.

The emulsions are prepared so that the mucoadhesive protein, such as lactoferrin, interacts or associates with the surface proteins on the probiotic microorganism, such as bacteria, so that the probiotic is microencapsulated or associated through surface proteins on the surface of the microorganism with the mucoadhesive protein, such as lactoferrin, via physical and/or chemical interactions. This is achieved by preparing emulsions with the appropriate stoichiometric ratios of mucoadhesive protein to probiotic (roughly 1:5 to 5:1, 1:4 to 4:1, 1:3 to 3:1, 1:2 to 2:1 and 1:1 and ranges in between) and a sufficient concentration of probiotic, such as at least 3%, generally at least 4%, by weight, of the emulsion.

The emulsion compositions contain about or at 1-10% probiotic and 2-10% Lactoferrin, so that the total of both is about 10%, or in the range of 10% to 15%, and contain no less than 2% mucoadhesive protein, such as lactoferrin. In contrast, prior art compositions that contain lactoferrin and probiotics, such as infant formulas, do not produce them by having the probiotic and lactoferrin interact, and, in general, the amount of lactoferrin is much lower, typically 0.2% at most.

The emulsions are stable oil in polar protic solvent or polar protic solvent in oil, and are prepared by dissolving the components of the composition in the oil and/or polar protic solvent, other than water, phases and mixing the two phases under constant temperature and pressure to form emulsions, which are then spray-dried to produce the powders. They can be prepared by any suitable method for making emulsions.

Also provided are powders. The powders are prepared by spray drying the emulsions, which contain the lactoferrin and probiotics. The powders are produced by spray drying the emulsions, which removes any solvent that can evaporate. The powders contain the same ingredients as the emulsions, but without the polar protic solvent, thereby containing the probiotic with the encapsulating mucoadhesive protein bound thereto, and the other ingredients, including dry forms of one or more of the binder, surfactant, stabilizer, oil, and emulsifier and flavorings. In contrast to prior art powders in which powdered forms of lactoferrin and probiotic are mixed, in the powders provided herein, the mucoadhesive protein, such as the lactoferrin, interacts via a chemical or physical interaction. The mucoadhesive protein interacts or associates with surface proteins on the probiotic microorganism. The mucoadhesive protein interacts or associates with surface proteins on the probiotic microorganism to encapsulate the probiotic microorganism whereby the stability of the microorganism increases. The powders and emulsions do not require refrigeration and have shelf-life that is as long as a year or more. The instantly claimed emulsions and spray dried powders produced therefrom are shelf stable at room temperature for up to 3 months, 6 months, or a year or more. Combining the mucoadhesive protein, such as lactoferrin, with probiotics as described herein so that the mucoadhesive protein, such as lactoferrin, interacts or associates with the probiotic not only increases shelf life of the probiotic, but results in increased colonization and increased probiotic growth upon ingestion.

Methods of making the compositions also are provided. The emulsions can be prepared as described in copending applications International PCT application publication WO 2016/044813 and U.S. application Ser. No. 14/866,717, which is published as U.S. Publication No. 2016/0081927, or any suitable methods, whereby the mucoadhesive protein, such as lactoferrin, and the probiotic are associated via interactions, which can be physical and/or chemical, between the lactoferrin and the proteins on the surface of the probiotic bacteria. Such bonds typically are physical or chemical bonds. The mucoadhesive protein, such as lactoferrin, when prepared as an emulsion with the probiotic such that the total amount of probiotic and mucoadhesive protein, is about 5%-20%, by weight of the emulsion composition, where the amount of probiotic is at least about 2%, such as 3%-8%, by weight of the composition. The amount of probiotic can be between about or at 3%-8%, such as 4% to 5%, up to about 20%, and the mucoadhesive protein is the same, such that the total of the two is 5%-20%, such as 10%, by weight of the composition. It is important to have this stoichiometry of probiotic and mucoadhesive protein, such as lactoferrin, so that the lactoferrin can encapsulate all or a sufficient amount of the probiotic to render the probiotic shelf stable at room temperature for extended periods of time, including more than 6 months, 12 months, 18 months, and typically at least 12 months.

The compositions provided herein are prepared by mixing an oil phase with a polar phase at a mixing speed that does not degrade and disintegrate any of the active ingredients of the composition. The mixing speed can range from about 100 RPM up to about 60,000 RPM. The temperature, pressure, and pH conditions during the mixing step are maintained so that all the components in the oil and polar protic solvent, other than water, phase are dissolved and the active ingredients are not degraded in any way. A suitable temperature during the mixing step can be determined empirically for a particular combination of ingredients in the composition. Typically, the temperature is maintained at about 100-120° F., in some embodiments at about 115° F. The pressure during the mixing is maintained at about 25 PSI (pounds per square inch). The pH during the mixing step is a function of the particular mucoadhesive protein and the agent to be delivered in the composition. Typically the pH is basic or neutral.

The emulsions provided herein are spray dried to produce powders. Provided are methods for spray drying the compositions. Hence provided are compositions containing a mucoadhesive protein, such as any listed herein, including a transferrin, such as a lactoferrin, and the probiotic. Because the mucoadhesive proteins are thermally sensitive and can denature at 60° C., it is difficult to spray dry the compositions using a conventional heated spray dryer as these proteins precipitate and clog in the nozzle, and also denature the protein. Compositions containing mucoadhesive proteins, such lactoferrin, typically are freeze-dried as a spray dried powder in order to pasteurize and preserve its bioactivity functions. Provided herein is an alternative method, which allows the composition containing the mucoadhesive protein, such as lactoferrin, to be heated in a spray dryer without impairing its biological activity. The methods herein permit pasteurization of the compositions and spray drying at high temperature, while maintaining solubility and biological activity of the compositions and components, such as probiotics, of the compositions. By processing the probiotic and the mucoadhesive protein in the oil phase, the resulting emulsion is less susceptible to degradation and can be spray-dried without inactivating the probiotic component.

In accord with the methods, the mucoadhesive protein, such as lactoferrin, is introduced into the oil phase of an emulsion, such as any described herein. The oil ingredients, encapsulate or interact with the temperature sensitive mucoadhesive protein, such as lactoferrin, and act to protect, such as, as a protective layer or medium, that withstands the heat during preparation of the emulsion phase and also during the spray drying process. This is advantageous for formulating the probiotics.

For example, in an exemplary embodiment, the mucoadhesive protein, such as lactoferrin, is dissolved in the oil phase at or about 40° C. (35° C.–45° C.). For probiotic formulations, the probiotic is processed with the mucoadhesive protein, such as lactoferrin. The preparation of the emulsion of the oil and the polar protic solvent phase is performed at or about at 50° C. to 55° C. to produce the emulsion. The emulsion is cooled down to at or about 25° C. to 35° C., such as to about or at 30° C. The emulsion then is spray dried using a conventional heated spray dryer (i.e., a Model: CIT-LSD-H1500) at inlet temperature of 155° C. to 165° C. such as 160° C. or in some embodiments at a temperature of 270° C. to 290° C. such as 280° C. to produce a powder. In accord with such methods, no precipitate forms, so that the nozzle does not clog.

DETAILED DESCRIPTION

Outline
A. Definitions
B. Compositions
  1. Mucoadhesive proteins
  2. Probiotic microorganisms
  4. Surface Active Agents
  5. Polymers
  6. Cosolvents
  7. Binders
  8. Other additives
C. Exemplary Compositions and their preparation
  1. Preparation of the emulsions
    a. Formulating the emulsions
    b. Exemplary ingredients and typical concentration ranges
      i. Surfactants
      ii. Sucrose fatty acid ester surfactants
      iii. Production of sucrose esters
      iv. Stabilizers
        (a) Bicarbonates and carbonates
        (b) Edible or ingestible acids
        (c) Antioxidants
      v. Polar solvents
      vi. Binders
      vii. Co-surfactants (emulsifiers)
      viii. Emulsion stabilizers (co-emulsifiers)
      ix. pH adjusters
  2. Powder compositions containing probiotics and a mucoadhesive proteins
    a. Formulating the powder compositions
    b. Ingredients and concentration ranges
D. Exemplary methods for preparing the emulsions
  1. Equipment employed in the methods
    a. Scales
    b. Purifiers
    c. Vessels
    d. Mixers
    e. Heating/cooling apparatuses
    f. Transfer devices
    g. Evaluation equipment
  2. General methods for producing the compositions
    a. Oil phase ingredients
    b. Oil phase production
    c. Polar phase ingredients
    d. Polar phase production
    e. Combining phases
    f. Cooling
    g. Spray drying
    h. Filtration, additions, evaluation and packaging
    i. Cleaning the equipment
E. Methods of use
F. Articles of manufacture
G. Examples

A. DEFINITIONS

Unless defined otherwise, all technical and scientific terms used herein have the same meaning as is commonly understood by one of skill in the art to which the invention(s) belong. All patents, patent applications, published applications and publications, GenBank sequences, websites and other published materials referred to throughout the entire disclosure herein, unless noted otherwise, are incorporated by reference in their entirety. In the event that there are a plurality of definitions for terms herein, those in this section prevail. Where reference is made to a URL or other such identifier or address, it is understood that such identifiers can change and particular information on the internet can come and go, but equivalent information can be found by searching the internet. Reference thereto evidences the availability and public dissemination of such information.

As used herein, "probiotics" are live microorganisms that confer health benefits when consumed. Probiotics include among other species of microorganisms, bacteria of the *Bifidobacterium* and *Lactobacillus* genera. Probiotics are consumed because they have a beneficial effect on animal and/or human health, such as in the human gastrointestinal (GI) and vaginal tracts. The bacterial genera that are probiotics include *lactobacilli* and *bifidobacteria*, and other beneficial bacterial species, such as *Streptococcus thermophilis*.

As used herein, "mucoadhesive proteins" refer to any natural or synthetic proteins, polypeptides or fragments thereof that possess the mucoadhesive property. Non-limiting examples of mucoadhesive proteins include mucin proteins and transferrins. In certain embodiments, the protein for use in the compositions and methods provided herein is lactoferrin. In certain embodiments, the mucoadhesive protein present in a composition provided herein is in an amount sufficient to confer a mucoadhesive property to the composition.

As used herein, "mucoadhesive property" refers to a property whereby a natural or synthetic substance, such as a protein, when applied to a mucosal epithelium adheres to or penetrates a subject's mucous membrane for a period of time sufficient to quantitatively deliver a composition provided herein to the subject. The composition can anchor in and/or penetrate into a mucosal surface. Adhesion of mucoadhesive proteins to a mucous membrane occurs generally, although not necessarily or exclusively, via secondary chemical bonds, such as hydrogen bonding and van der Waal forces (see, e.g., Tabor et al. (1977) *J. Colloid Interface Sci.* 58:213 and Good (1977) *J. Colloid Interface Sci.* 59:398-419). Parameters, such as mechanical binding to mucous membrane per se or the degree of biological effect of an agent delivered can be used as a measurement parameter to detect and quantitate mucoadhesion.

As used herein, mucoadhesive compositions contain mucoadhesive proteins. Their mucoadhesive (or penetrative) properties can be assessed by comparison to a control composition that does not contain the mucoadhesive protein(s) added to the composition. At similar viscosities, the emulsion prepared with a mucoadhesive protein or protein binds to a mucosal surface more strongly (i.e., more is bound or penetrates or is delivered) compared to a control emulsion without the mucoadhesive protein or protein(s). Such increase in delivery or binding or penetration is at least about 10%, 20%, 30%, 40%, 50%, 60%, 70%, 80%, 90% or 100% or greater mucosal binding than a control emulsion.

As used herein, "shelf life" refers to the time during which the probiotic in the emulsion or powder retains at least 90% of the original concentration of live probiotic microorganism when stored at room temperature. Reference to the concentration of probiotic is colony forming units/unit volume or unit mass. Colony forming units refer to the amount of actual microorganisms that, for example, can colonize the gut. It does not refer to spores, which can germinate, but which generally do not have probiotic activity because they cannot populate the gut or other body cavity. The emulsions and powders provided herein have longer shelf lives than prior powders and compositions that contain mixtures of mucoadhesive protein and probiotics, where they are not produced so that the mucoadhesive protein encapsulates or partially encapsulates the probiotic as described and provided herein.

As used herein, "room temperature" is about 20 to 25 degrees Celsius with an average of 23° C.

As used herein, "organoleptic properties" refer to sensory attributes of a food or beverage. Those of skill in the art understand such properties and they can be quantitated if needed. Organoleptic properties include, but are not limited to, taste, odor and/or appearance. Desirable organoleptic properties include those organoleptic properties that make a food or beverage composition desirable for consumption by an average human subject, such as a desirable odor, taste and/or appearance, or the lack of an undesirable odor, taste and/or appearance. Undesirable organoleptic properties include the presence of, for example, an undesirable taste, odor or appearance attribute, such as the presence of an "off-taste" or "off-odor," for example a fishy, grassy, metal or iron, sharp or tingling taste or odor, or the presence of an undesirable appearance attribute, such as separation or precipitation. In one example, the provided beverage compositions retain the same or about the same taste, odor and/or appearance as the same beverage composition that does not contain the one or more probiotics and/or mucoadhesive, i.e., lactoferrin, that is, the provided beverage compositions retain organoleptic properties desirable for consumption by an average human subject. Desirable and undesirable organoleptic properties can be measured by a variety of methods known to those skilled in the art, including, for example, organoleptic evaluation methods by which undesirable properties are detectable by sight, taste and/or smell and chemical tests, as well as by chemical analytical methods.

As used herein, a "solvent" is an ingredient that can be used to dissolve another ingredient. Solvents include polar and non-polar solvents. Non-polar solvents include oils and other non-polar ingredients that dissolve non-polar compounds. Typically, the non-polar solvent is an oil that is included in the concentrates or liquid dilution compositions provided herein in addition to the non-polar compound. The non-polar solvent typically is not the non-polar compound itself, i.e., is distinct from the non-polar compound. More than one non-polar solvent can be used. Certain compounds, for example, flaxseed oil and safflower oil, can be non-polar solvents and non-polar active ingredients. Typically, the non-polar solvent contains one or more oils, typically oils other than the non-polar active ingredient or oil(s) not contained in the active ingredient. Exemplary non-polar solvents include, but are not limited to, oils (in addition to the non-polar active ingredient), for example, vitamin E oil, flaxseed oil, CLA, borage oil, rice bran oil, D-limonene, canola oil, corn oil, MCT (medium chain triglycerides) oil and oat oil. Other oils also can be used.

As used herein, MCT oil is comprised of primarily caprylic and capric fatty acids, and is a light-yellow, odorless, translucent liquid at room temperature. MCT oil occurs naturally in coconut oil and other foods.

As used herein, "polar solvent" refers to a solvent that is readily miscible with water and other polar solvents. Polar solvents are well-known and can be assessed by measuring any parameter known to those of skill in the art, including dielectric constant, polarity index and dipole moment (see, e.g., Przybitek (1980) "High Purity Solvent Guide," Burdick and Jackson Laboratories, Inc.). For example, polar solvents generally have high dielectric constants, such as greater than or about 15, generally have high polarity indices, typically greater than or about 3, and generally large dipole moments, for example, greater than or about 1.4 Debye. Polar solvents include polar protic solvents and polar aprotic solvents.

As used herein, a "polar protic solvent" is a solvent containing a hydrogen atom attached to an electronegative atom, such that the hydrogen has a proton-like character and/or the bond between the hydrogen and electronegative atom is polarized. Exemplary polar protic solvents include, but are not limited to, water, alcohols, including monohydric, dihydric and trihydric alcohols, including, but not limited to, methanol, ethanol, glycerin and propylene glycol.

As used herein, glycerin is interchangeable with glycerine and glycerol (IUPAC name propane-1,2,3-triol) and has the formula: HO—CH$_2$CH(OH)CH$_2$—OH.

As used herein, cluster dextrin (also called highly branched cyclic dextrin) is a type of dextrin that is produced from amylopectin via cyclization reaction of a branching enzyme (BE,1,4-α-D-glucan: 1,4-α-D-glucan 6-α-D-(1,4-α-D-glucano)-transferase, EC 2.4.1.18).

As used herein, "biologically compatible substance" refers to a substance that, when administered to a subject, such as a human, does not produce undesired or toxic effects.

As used herein, "an agent" is any substance that can be delivered via compositions provided herein to a mucosal surface of a subject. Generally for purposes herein, the agent is one that is susceptible to degradation in the presence of water or is unstable in the presence of water or moisture.

As used herein, "a biologically active agent," "a biological agent," or "an agent" is any substance which when introduced into the body causes a desired biological response, such as altering body function at the cellular, tissue or organ level and/or altering cosmetic appearance. Such substance can be any synthetic or natural element or compound, protein, cell, or tissue including a pharmaceutical, drug, therapeutic, nutritional supplement, herb, hormone, or the like, or any combinations thereof. The terms also encompass pharmaceutically acceptable, pharmacologically active derivatives of those active agents specifically mentioned herein, including, but not limited to, salts, esters, amides, prodrugs, active metabolites, isomers, fragments and analogs. When the terms "biologically active agent," "biological agent" and "agent" are used, then, or when an active agent is specifically identified, it is intended to include the active agent per se as well as pharmaceutically acceptable, pharmacologically active salts, esters, amides, prodrugs, active metabolites, isomers, fragments and analogs.

As used herein, a "subject" is defined as an animal, including a mammal, typically a human.

As used herein, "quantitative delivery" refers to delivery of a substantial portion of the amount administered, and is typically, greater than 50%, 60%, 70%, 80%, 85%, 90%, 91%, 92%, 93%, 94%, 95%, 96%, 97%, 98%, or 99%.

As used herein, "therapeutically effective amount" refers to an amount of the active agent for a desired therapeutic, prophylactic, or other biological effect or response when a composition is administered to a subject in a single dosage form. The particular amount of active agent in a dosage will vary widely according to conditions such as the nature of the active agent, the nature of the condition being treated, the age and size of the subject.

As used herein, an "emulsion" is a colloidal dispersion of two immiscible liquids, such as oil and water, in the form of droplets. The emulsions are generally stabilized by an interfacial film of surface active agents or surfactant molecules, such as polysorbate-80 and the stability of an emulsion can be determined by well-known routine methods.

As used herein, surfactants (or "surface-active agents") are chemical or naturally occurring entities which, when dissolved in an aqueous solution, reduce the surface tension of the solution or the interfacial tension between the aqueous phase and the oil phase, to form a stable oil in polar protic solvent, other than water, or polar protic solvent, other than water, in oil emulsion. The surfactant molecules are amphiphilic and contain hydrophilic head groups and hydrophobic tails. The surfactant molecules form various macro-molecular structures in an emulsion, such as micelles, inverse micelles, lipid bilayers (liposomes) and cubosomes. The exact macromolecular structure which is formed depends on the relative sizes of the hydrophilic and hydrophobic regions of the surface active molecules.

As used herein, "mucoadhesive protein associated with a probiotic" means the mucoadhesive protein is associated with the probiotic bacterium via chemical or physical interaction, such as hydrogen bond or van der Waal's forces, particularly with a surface protein or proteins. The mucoadhesive protein, such as lactoferrin, when mixed with a probiotic in an emulsion can encapsulate partially or completely the probiotic microorganism, such as bacteria, to protect it from degradation, thereby improving shelf-life of the probiotic in an emulsion or a powder produced by drying, such as spray drying, the emulsion. The probiotic is a live bacterium, not a spore thereof, that can colonize the gut and intestinal tract or other body cavity substantially as well as the probiotic that has not been stored.

As used herein, "viscosity" refers to a physical property of fluids that determines the internal resistance to shear forces and is expressed in centipoise (cp).

As used herein, "medium chain" represents a hydrocarbon chain of $C_8$ to $C_{12}$ and short chain is a hydrocarbon chain of less than $C_8$ and long chain means a hydrocarbon chain of more than $C_{12}$. The polar protic solvent, other than water, phase in the emulsion can be water, aqueous solutions, alcohols and alcohol solutions.

As used herein, the stability of a composition provided herein refers to the length of time at a given temperature that greater than 10%, 20%, 30%, 40%, 50%, 60%, 70%, 80%, 85%, 90%, 91%, 92%, 93%, 94%, 95%, 96%, 97%, 98% or 99% of the initial amount of the agent to be delivered, e.g., a probiotic, is present in the composition. Thus, for example, a composition that is stable for 30 days at 25° C. would have greater than 10%, 20%, 30%, 40%, 50%, 60%, 70%, 80%, 85%, 90% 91%, 92%, 93%, 94%, 95%, 96%, 97%, 98% or 99% of the initial amount of active ingredient present in the composition at 30 days following storage at 25° C.

As used herein, pharmaceutically acceptable solvates and hydrates are complexes of a compound with one or more polar protic solvent molecules, in certain embodiments 1 to about 100, in other embodiments 1 to about 10, in further embodiments one to about 2, 3 or 4, solvent molecules.

As used herein, "treatment" means any manner in which one or more of the symptoms of a condition, disorder or disease are ameliorated or otherwise beneficially altered. Treatment also encompasses any pharmaceutical use of the compositions herein, such as use for treating diabetes.

As used herein, amelioration of the symptoms of a particular disorder by administration of a particular pharmaceutical composition refers to any lessening, whether permanent or temporary, lasting or transient that can be attributed to or associated with administration of the composition.

As used herein, a "composition" refers to a mixture of two or more ingredients.

As used herein, "co-surfactant" is used to refer to a surfactant that is used in the provided compositions in combination with the primary surfactant, for example, sucrose fatty acid esters described herein, for example, to improve the emulsification of the provided compositions and/or compounds, for example, to emulsify the ingredients. In one example, the provided compositions can contain at least one surfactant and at least one co-surfactant. Typically, the co-surfactant represents a lower percent, by weight (w/w), of the provided compositions, compared to the surfactant. Thus, the provided compositions typically have a lower concentration of the co-surfactant(s) than of the surfactant.

As used herein, "HLB" refers to a value that is used to index and describe a surfactant according to its relative hydrophobicity/hydrophilicity, relative to other surfactants. A surfactant's HLB value is an indication of the molecular balance of the hydrophobic and hydrophilic portions of the surfactant, which is an amphipathic molecule. Each surfactant and mixture of surfactants (and/or co-surfactants) has an HLB value that is a numerical representation of the relative weight percent of hydrophobic and hydrophilic portions of the surfactant molecule(s). HLB values are derived from a semi-empirical formula. The relative weight percentages of the hydrophobic and hydrophilic groups are indicative of surfactant properties, including the molecular structure, for example, the types of aggregates the surfactants form and the solubility of the surfactant (see, for example, Griffin (1949) *J. Soc. Cos. Chem.* 1:311). Surfactant HLB values range from 1-45, while the range for non-ionic surfactants typically is from 1-20. The more lipophilic a surfactant is, the lower its HLB value. Conversely, the more hydrophilic a surfactant is, the higher its HLB value.

As used herein, "polymer" also includes combinations or mixtures of more than one polymer wherein such combination or mixture exists in single or multiphase blends.

As used herein, "unit-dose forms" refers to physically discrete units suitable for human and animal subjects and packaged individually as is known in the art.

B. COMPOSITIONS

Provided herein are emulsions and powders that contain mucoadhesive protein, such as lactoferrin, probiotics and oils and polar solvents. The compositions provided herein do not contain any polyalkylene derivatives of vitamin E, such as a PEG-derivative of vitamin E, including any of tocopheryl polyethylene glycol succinate (TPGS), tocopheryl polyethylene glycol sebacate, tocopheryl polyethylene glycol dodecanodioate, tocopheryl polyethylene glycol suberate, tocopheryl polyethylene glycol azelaate, tocopheryl polyethylene glycol citraconate, tocopheryl polyethylene glycol methylcitraconate, tocopheryl polyethylene glycol itaconate, tocopheryl polyethylene glycol maleate, tocopheryl polyethylene glycol glutarate, tocopheryl polyethylene glycol glutaconate, tocopheryl polyethylene glycol fumarate, tocopheryl polyethylene glycol phthalate, tocotrienol polyethylene glycol succinate, tocotrienol polyethylene glycol sebacate, tocotrienol polyethylene glycol dodecanodioate, tocotrienol polyethylene glycol suberate, tocotrienol polyethylene glycol azelaate, tocotrienol polyethylene glycol citraconate, tocotrienol polyethylene glycol methylcitraconate, tocotrienol polyethylene glycol itaconate, tocotrienol polyethylene glycol maleate, tocotrienol polyethylene glycol glutarate, tocotrienol polyethylene glycol glutaconate, tocotrienol polyethylene glycol fumarate and tocotrienol polyethylene glycol phthalate.

Probiotics are among the ingredients. The probiotics are formulated in the oil phase of the emulsions with the mucoadhesive protein, such as lactoferrin, so that the mucoadhesive protein, such as lactoferrin, interacts with proteins on the surface of the microorganism to encapsulate (partially or completely, but sufficiently, to increase shelf life at room temperature (about 20° C.)) of the emulsions and powders. The powders are produced by spray-drying the emulsions. The following discussion describes the components of the emulsions; the powders result from spray drying the emulsions. Hence the amounts and ratios of ingredients are different in the powders and emulsions, depending upon how much protic polar solvent and other components that evaporate when spray dried.

1. Mucoadhesive Proteins

The compositions contain one or more mucoadhesive proteins. The mucoadhesive proteins for use in the compositions and methods provided herein include any protein that imparts a mucoadhesive property to the composition whereby the composition, adheres, via physical or chemical interactions to the surface of the probiotic microorganism. Interaction of a mucoadhesive protein to a cell, such as a microorganism, occurs primarily via secondary chemical bonds, such as hydrogen bonding and van der Waal forces.

Any mucoadhesive protein that is biologically compatible can be employed. Mucoadhesive proteins for use herein include, but are not limited to, natural or synthetic proteins, polypeptides or fragments thereof that possess the mucoadhesive property. Mucoadhesive proteins can be screened for their ability to be used as mucoadhesives compositions provided herein according to the methodology described in Smart et al., 1982 *J. Pharm. Pharmacol.* 34:70P and Smart et al., 1984 *J. Pharm. Pharmacol.* 36:295. The methodology involves estimating values of adhesive strength between the mucoadhesive protein and the mucous membrane.

In certain embodiments, the mucoadhesive proteins are selected from a family of mucin proteins and transferrins. In certain embodiments, the mucoadhesive protein is from the transferrin family and is selected from bovine lactoferrin, human lactoferrin, lactoferrin binding proteins, recombinant human lactoferrin, lactoferricin, lactoferricin b, transferrin binding proteins, bovine transferrin, ovotransferrin, neutrophil granules, apo-lactoferrin and lanthanide-lactoferrin. In certain embodiments, the mucoadhesive proteins are selected from among lactoferrin, lactoferrin binding proteins, recombinant lactoferrin, lactoferricin, lactoferricin b, transferrin binding proteins, transferrin, ovotransferrin, neutrophil granules, apo-lactoferrin, immunoglobulin, albumin and lanthanide-lactoferrin. In certain embodiments, the mucoadhesive protein is selected from albumin, immunoglobulin and lactoferrin.

In certain embodiments, the mucoadhesive protein for use in the compositions and methods provided herein is lactoferrin. In certain embodiments, the compositions contain one, two or three mucoadhesive proteins. In certain embodiments, the compositions contain one mucoadhesive protein. In certain embodiments, the mucoadhesive protein in the compositions provided herein is present in an amount sufficient to confer a mucoadhesive property to the composition.

The mucoadhesive proteins can associate with the microorganism via a chemical or physical interaction. The amount of mucoadhesive protein in the emulsions is typically about 1% to 10%, by weight, and in the powder is higher, typically about 2% to 20% by weight. In the powders, the total amount of probiotic and mucoadhesive protein, such as lactoferrin, is about 20% to 35% by weight, with a minimum of at least about 5% probiotic, and at least about 5% mucoadhesive protein.

Typically, the mucoadhesive protein is present at a concentration of about 5% up to about 25%, by weight, such that the total amount of mucoadhesive protein, such as lactoferrin, and probiotic is up to or is about 20%-35%, particularly about or at 25% or 30%, by weight, of the powder composition. To achieve the increased stability and enhanced shelf life, these relatively high amounts of mucoadhesive protein, such as lactoferrin, and probiotic and stoichiometry thereof is important.

2. Probiotic Microorganisms

The mucoadhesive protein, such as lactoferrin, reduces degradation of probiotics in the compositions. The probiotic and mucoadhesive protein, such as lactoferrin, are processed in the oil phase. Probiotics include bacterial strains that improve health or digestion, such as by colonizing the digestive tract to improve digestive flora. Such probiotics are well known and include, for example, those sold under the trademark FloraFIT® probiotics by the Dupont™ Danisco® corporation, and include strains of genera of *Bifidobacteria* and *Lactobacillus*. Any such probiotic or mixture thereof, known to the skilled artisan, can be included in the water-free emulsion formulations and powders provided herein. Generally, the amount of probiotic in the composition will vary from at least about 5% or 5% up to about 25%-35%, by weight of the composition.

The compositions can be formulated for multiple dosage administration or single dosage administration. They can be provided in suitable containers. The emulsions can be provided in syringes for ease of delivery. Generally, the amount of probiotic in the composition will vary from at least about 5% or 5% up to about 25%, by weight of the powder composition, so that the total of probiotic and mucoadhesive protein, such as lactoferrin, is about 25%-35%, 25%-30%, or around or at 25%, by weight of the powder composition. This stoichiometry helps ensure that the stability of probiotic by virtue of interaction with the mucoadhesive protein is exploited.

The compositions can contain other agents, such as other supplements and therapeutics. The additional agent is selected, for example, from anticonvulsants, analgesics, antiparkinsons, anti-inflammatories, calcium antagonists, anesthetics, antimicrobials, antimalarials, antiparasitics, antihypertensives, antihistamines, antipyretics, alpha-adrenergic agonists, alpha-blockers, biocides, bactericides, bronchial dilators, beta-adrenergic blocking drugs, contraceptives, cardiovascular drugs, calcium channel inhibitors, depressants, diagnostics, diuretics, electrolytes, enzymes, hypnotics, hormones, hypoglycemics, hyperglycemics, muscle contractants, muscle relaxants, neoplastics, glycoproteins, nucleoproteins, lipoproteins, non denatured whey protein, ophthalmics, psychic energizers, sedatives, steroids, sympathomimetics, parasympathomimetics, tranquilizers, urinary tract drugs, vaccines, vaginal drugs, vitamins, minerals, nonsteroidal anti-inflammatory drugs, angiotensin converting enzymes, polynucleotides, polypeptides, polysaccharides, and nutritional supplements including herbal supplements. See, U.S. Pat. Nos. 8,252,323; 7,906,140 and 8,414,914, which describe agents for inclusion in such compositions.

Probiotics, including species of *Lactobacilli* and *Bifidobacteria*, can be isolated from traditional fermented products, such as fermented foods; non-fermented foods, such as fresh fruits and vegetables, grains, honeycombs or honey, animal milk; the intestine and/or digestive tract of animals and/or humans; feces; the breast milk of human subjects or other animals; and other food and non-food sources. Probiotics are commercially available from various sources (see, e.g., the Examples).

The genera and species of bacteria, yeast and mold are considered probiotics include, but are not limited to: *Lactobacillus, Streptococcus, Leuconostoc, Streptococcus, Leuconostoc, Pediococcus, Propionibacterium, Enterococcus, Bifidobacterium, Bacillus, Saccharomyces cerevisiae, Candida pintoloesii, Aspergillus niger* and *Aspergillus oryza*. Other exemplary species include, but are not limited to, *Bifidobacterium adolescentis, Bifidobacterium angulatum, Bifidobacterium animalis, Bifidobacterium asteroides, Bifidobacterium bifidum, Bifidobacterium boum, Bifidobacterium breve, Bifidobacterium catenulaturn, Bifidobacterium choerinurn, Bifidobacterium coryneforme, Bifidobacterium cuniculi, Bifidobacterium dentium, Bifidobacterium gallicum, Bifidobacterium gallinarum, Bifidobacterium indicum, Bifidobacterium infantis, Bifidobacterium longum, Bifidobacterium longum DJO10A, Bifidobacterium longum NCC2705, Bifidobacterium magnum, Bifidobacterium merycicum, Bifidobacterium minimum, Bifidobacterium pseudocatenulatum, Bifidobacterium pseudolongum, Bifidobacterium pseudolongum* subsp. *globosum, Bifidobacterium pullorum, Bifidobacterium ruminantium, Bifidobacterium saeculare, Bifidobacterium scardovii, Bifidobacterium subtile, Bifidobacterium suis, Bifidobacterium thermacidophilum, Bifidobacterium thermacidophilum* subsp. *suis, Bifidobacterium thermophilum, Bifidobacterium urinalis, Lactobacillus acetotolerans, Lactobacillus acidipiscis, Lactobacillus acidophilus, Lactobacillus agilis, Lactobacillus algidus, Lactobacillus alimentarius, Lactobacillus amylolyticus, Lactobacillus amylophilus, Lactobacillus amylovorus, Lactobacillus animalis, Lactobacillus arizonensis, Lactobacillus aviarius, Lactobacillus bifermentans, Lactobacillus brevis, Lactobacillus buchneri, Lactobacillus casei, Lactobacillus cellobiosus, Lactobacillus coleohominis, Lactobacillus collinoides, Lactobacillus coryniformis, Lactobacillus coryniformis* subsp. *coryniformis, Lactobacillus coryniformis* subsp. *torquens, Lactobacillus crispatus, Lactobacillus curvatus, Lactobacillus cypricasei, Lactobacillus delbrueckii, Lactobacillus delbrueckii* subsp. *bulgaricus, Lactobacillus delbrueckii* subsp. *delbrueckii, Lactobacillus delbrueckii* subsp. *lactis, Lactobacillus durianis, Lactobacillus equi, Lactobacillus farciminis, Lactobacillus ferintoshensis, Lactobacillus fermentum, Lactobacillus fornicalis, Lactobacillus fructivorans, Lactobacillus frumenti, Lactobacillus fuchuensis, Lactobacillus gallinarum, Lactobacillus gasseri, Lactobacillus graminis, Lactobacillus hamsteri, Lactobacillus helveticus, Lactobacillus helveticus* subsp. *jugurti, Lactobacillus heterohiochii, Lactobacillus hilgardii, Lactobacillus homohiochii, Lactobacillus intestinalis, Lactobacillus japonicus, Lactobacillus jensenii, Lactobacillus johnsonii, Lactobacillus kefir, Lactobacillus kefiri, Lactobacillus kefiranofaciens, Lactobacillus kefirgranum, Lactobacillus kimchii, Lactobacillus kunkeei, Lactobacillus leichmannii, Lactobacillus letivazi, Lactobacillus lindneri, Lactobacillus malefermentans, Lactobacillus mali, Lactobacillus maltaromicus, Lactobacillus manihotivorans, Lactobacillus mindensis, Lactobacillus mucosae, Lactobacillus murinus, Lactobacillus nagelii, Lactobacillus oris, Lactobacillus panis, Lactobacillus pantheris, Lactobacillus parabuchneri, Lactobacillus paracasei, Lactobacillus paracasei* subsp. *paracasei, Lactobacillus paracasei* subsp. *tolerans, Lactobacillus parakefiri, Lactobacillus paralimentarius, Lactobacillus paraplantarum,*

*Lactobacillus pentosus, Lactobacillus perolens, Lactobacillus plantarum, Lactobacillus pontis, Lactobacillus psiffaci, Lactobacillus reuteri, Lactobacillus rhamnosus, Lactobacillus ruminis, Lactobacillus sakei, Lactobacillus sakei* L45, *Lactobacillus salivarius, Lactobacillus salivarius* subsp. *salicinius, Lactobacillus salivarius* subsp. *salivarius, Lactobacillus sanfranciscensis, Lactobacillus sharpeae, Lactobacillus* sp. NGRI 0001, *Lactobacillus suebicus, Lactobacillus thermotolerans, Lactobacillus vaccinostercus, Lactobacillus vaginalis, Lactobacillus vermiforme, Lactobacillus versmoldensis, Lactobacillus zeae, Lactococcus garvieae, Lactococcus lactis, Lactococcus lactis* subsp. *cremoris, Lactococcus lactis* subsp. *hordniae, Lactococcus lactis* subsp. *lactis, Lactococcus lactis* subsp. *lactis* bv. *diacetylactis, Lactococcus piscium, Lactococcus plantarum, Lactococcus raffinolactis, Leuconostoc argentinum, Leuconostoc carnosum, Leuconostoc citreum, Leuconostoc fallax, Leuconostoc ficulneum, Leuconostoc fructosum, Leuconostoc gasicomitatum, Leuconostoc gelidum, Leuconostoc inhae, Leuconostoc kimchii, Leuconostoc lactis, Leuconostoc mesenteroides, Leuconostoc mesenteroides* subsp. *cremoris, Leuconostoc mesenteroides* subsp. *dextranicum, Leuconostoc mesenteroides* subsp. *mesenteroides, Leuconostoc mesenteroides* subsp. *mesenteroides* ATCC 8293, *Leuconostoc pseudomesenteroides, Propionibacterium acidipropionici, Propionibacterium acnes, Propionibacterium australiense, Propionibacterium avidum, Propionibacterium cyclohexanicum, Propionibacterium freudenreichii, Propionibacterium freudenreichii* subsp. *freudenreichii, Propionibacterium freudenreichii* subsp. *shermanii, Propionibacterium granulosum, Propionibacterium jensenii, Propionibacterium lymphophilum, Propionibacterium microaerophilum, Propionibacterium propionicum, Propionibacterium. thoenii, Saccharomyces delbrueckii, Saccharomyces cerevisiae, Saccharomyces unisporus, Saccharomyces globosus, Saccharomyces carlsbergensis, Kluyveromyces fragilis, Kluyveromyces bulgaricus, Kluyveromyces lactis, Torula holmii, Candida tenuis*, R2C2, INIX, ES1 and K2. Other exemplary species include, but are not limited to, *Lactobacillus acidophilus, Lactobacillus brevis, Lactobacillus bulgaricus, Lactobacillus buchneri, Lactobacillus casei, Lactobacillus curvatus, Lactobacillus fermenturn, Lactobacillus johnsonii, Lactobacillus mesenteroides, Lactobacillus murinus, Lactobacillus paracasei, Lactobacillus pentosus, Lactobacillus plantarum, Lactobacillus rapi, Lactobacillus rhamnosus, Lactobacillus salivarius, Lactobacillus rhamnosus* GG, *Lactobacillus kunkeei, Lactobacillus sakei, Bifidobacterium bifidum, Bifidobacterium infantis, Bifidobacterium lactis, Bifidobacterium longum, Streptococcus thermophilis, Enterococcus faecalis, Enterococcus facecium, Enterococcus thailandensis, Bacillus lichenformis, Bacillus cereus* var. *toyoi, Bacillus clausii, Bacillus coagulans, Bacillus laterosporus, Bacillus pumilus, Bacillus racemilacticus, Pediococcus pentosaceus, Pediococcus acidilactici, Pediococcus lolii, Propionibacterium freudenreichii, Aerococcus viridans, Leuconostoc cremoris, Leuconostoc fallax, Leuconostoc mesenteroides, Staphylococcus arlettae*, and *Weissella cibaria*.

Exemplary of beneficial effects of probiotics include, for example, the following. The *lactobacillus* species are gram-positive lactic acid bacteria that absorb lactose and other monosaccharides in the intestinal tract to produce lactic acid, which has the beneficial effect of lowering the pH of the organs making the environment of the organs hostile for the growth of harmful bacterial. The *Bifidobacterium* species are the first species of microorganisms to colonize the sterile colon of a newborn baby that is nursed by its mother. *Bifidobacteria* use the mechanism of crowding to digest the nutrients that otherwise harmful bacteria would use for reproduction. (see, e.g., U.S. Pat. No. 9,549,984). *L. acidophilus* also produces anti-microbial substances (i.e., natural antibiotics) acidolin, acidolphilin, lactocidin, and bacteriocin, which increase the immune system's resistance against fungus, such as *Candida albican*, and the harmful bacterial species *Escherichia coli, Staphylococcus aureus, Listeria monocytogenes*, and *salmonella*.

*L. bulgaricus* enhances the digestibility of proteins and milk products, aids in the production of natural antibiotics, and has been used to treat gastrointestinal disorders such as enterocolitis. *L. casei* has protective activity against pathogenic *listeria* bacteria. *L. fermentum* prevents human immunodeficiency virus ("HIV") from infecting immune cells in infants (From Reuters Health, May 25, 2004, author Karla Gale, available at URL: pronutrition.org/archive/200406/msg00002.php).

*L. plantarum* helps produce lactolin, a natural antibiotic, and synthesizes L-lysine; *L. salivarius* is a facultative bacterium (i.e., a bacterial species that survives and grows in both anaerobic and aerobic environments) that is most abundant in the mouth and gums. *L. salivarius* has several advantages as a probiotic: it has the ability to break down undigested protein and disengage the toxins produced by protein putrefactions; it is useful to prevent and fight *Helicobacter pylori*, which is known to be a cause of ulcers; and because its population doubles every 20 minutes, smaller amounts of the probiotic can be administered.

*L. rhamnosus* exhibits stability over a broad range of temperatures and pH levels; it relieves hypersensitivity reactions and intestinal inflammation in individuals with eczema and food allergies. *B. animalis* is a probiotic bacterium that plays a role in intestinal mucosal defense. *B. animalis* has two subspecies: *B. animalis* subsp. *Animalis* and *B. animalis* subsp. *Lactis*, both of which prior to 2004 were referred to as *B. animalis* and *B. animalis* subsp. *Lactis*. (see Masco et al., *Int'l J Syst Evol Biol* 54:1137-1143 (2004)). Because *B. animalis* subsp. *Animalis* only grows in anaerobic environments and is incapable of growth in milk cultures, it is not useful as a probiotic. By contrast, *B. animalis* subsp. *Lactis*, which is a lactic acid bacterium characterized by its high oxygen resistance and production of considerable amounts of formate, grows well in milk cultures and thus, is a useful probiotic. *B. animalis* subsp. *Lactis* is added to infant formulas to ensure that newborn babies not being nursed have sufficient colonization of *bifidobacteria* and is the only *bifidobacterium* species that is found in yogurt cultures.

*B. bifidum* inhibits the growth of the harmful bacterial species *salmonella, listeria, shigella, E. coli*, and *Clostridium perfringens* by consuming their nutrients, such as for example, ferrous ions, which many harmful bacterial species require for growth. *B. bifidum* also synthesizes some vitamins and aids in the absorption of minerals such as calcium, magnesium, and zinc. *B. infantis* is the first probiotic to colonize the sterile digestive tract of an infant that is nursed by its mother. For infants that are formula fed, this probiotic may be administered in supplemental form in order to ensure that the newborn has the proper intestinal flora. *B. longum biovar longum* (referred to as *B. longum*) has been found to be able to eliminate nitrates from the intestinal tract. *S. thermophilis* generates lactase activity, facilitating the digestion of lactose in milk. *E. faecalis* and *E. faecium* are both lactic acid bacteria that have inhibitory effects against enteropathogens such as *E. coli, salmonellae, shigellae* and *clostridia*.

Infant formulae, however, whether powdered or liquid, differ from the powders and emulsions provided herein, in that because of the relatively high concentrations of the probiotic and mucoadhesive protein, such as lactoferrin, and the stoichiometry (i.e., 1:5 to 5:1, including 1:2 to 2:1, 1:3 to 3:1, 1:4 to 4:1) the mucoadhesive protein interacts with surface proteins on the probiotic, increasing its stability in a form that can colonize the gastrointestinal tract, vaginal track, and other body cavities to which it is administered. In the infant formulae and other commercial formulations, the amounts of lactoferrin and/or probiotic are far lower so that the encapsulation or interaction does not occur or is not sufficient to exploit the advantageous interaction.

3. Oils

The oils for use in the compositions include any oil obtained from a natural or synthetic source that is suitable for consumption by a subject. Oils suitable for administration to subjects, including humans, are known. Any such oil can be used. The oil can be of vegetable or animal origin. The oil phase also can be synthetic or semisynthetic oils that are nontoxic to a subject. Exemplary of oils for use herein include, but are not limited to mono-, di- and triglycerides, fatty acids, such as oleic, linoleic, palmitic, stearic, conjugated forms thereof and their esters, ethers and esters of propylene glycol and other polyols. The oil phase in the emulsion provided herein can contain any nontoxic oil, biocompatible oil, which includes, but is not limited to mono-, di- and triglycerides, fatty acids and their esters, ethers and esters of propylene glycol or other polyols. The fatty acids and esters (used as such or where they form part of a glyceride) can be short chain, medium chain or long chain. Exemplary oils include, but are not limited to, vitamin E oil, flaxseed oil, CLA, borage oil, rice bran oil, d-limonene, canola oil, corn oil, MCT oil, and oat oil. Other oils also can be used.

In certain embodiments, the oils are short, medium or long chain triglycerides. In certain embodiments, the oils are medium chain triglycerides (MCTs). In certain embodiments, the MCT is tricaprylic triglyceride ester (e.g., sold under the trademark Neobee® M5). Exemplary sources for oils contemplated herein include, but are not limited to All Spice, Almond, Anise, Apple, Apricot, Avocado, Basil, Bayberry, Benzoin, Bergamot, Borage Seed, Cajeput, Calendula, Canola, Carnation, Carrot seed, *Cassia* bark, Castor, Cayenne, Cedarwood, Chamomile, Cinnamon, Citronella, Conjugated Linolenic Acid, Clary sage, Clove bud, Coconut, Cod Liver, Corn, Cranberry, Cypress, Evening Primrose, *Eucalyptus*, Evergreen, Fir, Fish 18:12, Flax Seed, Frangipani, Frankincense, Freesia, *Gardenia*, Ginger, Grape Seed, Grapefruit, Heather, Honeysuckle, Hyacinth, Jasmine, Jojoba, Juniper berry, Lavender, Lecithin, Lemon, Lemon balm, Lemon, *verbena*, Lemongrass, Lilac, Lily of the valley, Lime, *Magnolia*, MCT, Menthol, Mulberry, Musk, Myrrh Oat, Olive, Orange, Oregano, Palm, Patchouli, Peach, Pennyroyal, Peppermint, Petitgrain, Pine, Pumpkin Seed, Rice Bran, Rose, Rosemary, Rosewood, Safflower, Sage, Salmon, Sandalwood, Sesame, Shark Liver, Soy Bean, Spearmint, Squalene, Strawberry, Sunflower, Tangerine, Tea tree, *Thuja* (Cedar leaf), Thyme, Tuna, Vanilla, Vitamin E, Wheat Germ, Wintergreen and Ylang ylang. In certain embodiments, the oil phase contains oat oil and tri caprylic triglyceride ester (e.g., sold under the trademark Neobee® M5).

The oil is present in an amount sufficient to dissolve the oil soluble ingredients in the composition. The amount generally is a function of the locus of administration, the agent to be administered and other such parameters and can be empirically determined. For example, in some embodiments, the oil is present at a concentration of about 1%, 2%, 3%, 4%, 5%, 10%, 20%, 25%, 30%, 35%, 40%, 45%, 50%, 55%, 60%, 65%, 70%, 75%, 80%, 85%, 90%, 95% or more by weight. Thus, in certain embodiments, the oil is present at about 3, 4, or 5% by weight up to about 90% by weight of the total weight of the composition. In other embodiments, the oil is present at a concentration of about 3, 4, or 5% by weight up to about 85% by weight of the total weight of the composition. In other embodiments, the oil is present at a concentration of about 5% by weight up to about 70% by weight of the total weight of the composition. In other embodiments, the oil is present at a concentration of about 5% by weight up to about 50% by weight of the total weight of the composition. In other embodiments, the oil is present at a concentration of about 5% by weight up to about 45% by weight of the total weight of the composition. In other embodiments, the oil is present at a concentration of about 5% by weight up to about 40% by weight of the total weight of the composition. In other embodiments, the oil is present at a concentration of about 5% by weight up to about 35% by weight of the total weight of the composition. In other embodiments, the oil is present at a concentration of about 5% by weight up to about 30% by weight of the total weight of the composition. In other embodiments, the oil is present at a concentration of about 5% by weight up to about 20% by weight of the total weight of the composition. In other embodiments, the oil is present at a concentration of about 45% by weight of the total weight of the composition. In other embodiments, the oil is present at a concentration of about 40% by weight of the total weight of the composition. In other embodiments, the oil is present at a concentration of about 35% by weight of the total weight of the composition. In other embodiments, the oil is present at a concentration of about 30% by weight of the total weight of the composition. In other embodiments, the oil is present at a concentration of about 20% by weight of the total weight of the composition. In other embodiments, the oil is present at a concentration of about 10% by weight of the total weight of the composition. In other embodiments, the oil is present at a concentration of about 7% by weight of the total weight of the composition. In other embodiments, the oil is present at a concentration of about 5% by weight of the total weight of the composition.

4. Surface Active Agents

The compositions provided herein can contain one or more surface active agents that are added in an amount sufficient to form a stable emulsion or facilitate such formation. The appropriate amount of surface active agent is a function of the agent for delivery and other components present in the emulsion, since some agents can have self-emulsifying properties and other agents and components affect surface tension. The surface active agents do not include vitamin E derivatives, such as polyalkylene-derivatives of vitamin E, including PEG-derivative of vitamin E.

The surface active agents for use herein are substances which, when dissolved in an aqueous solution, reduce the surface tension of the solution or the interfacial tension between the aqueous phase and the oil phase, to form a stable oil in polar protic solvent, other than water, or polar protic solvent, other than water, in oil emulsion. The surfactant molecules are amphiphilic and contain hydrophilic head groups and hydrophobic tails. The surfactant molecules form various macro-molecular structures in an emulsion, such as micelles, inverse micelles, lipid bilayers (liposomes) and cubosomes. The exact macromolecular structure which is formed depends on the relative sizes of the hydrophilic and hydrophobic regions of the surface active molecule. In certain embodiments, the surface active agent is selected from sodium lauryl sulfate; sorbitan laureate, sorbitan palmitate, sorbitan stearate (available under the trademark Span® 20, 40, 60etc.); polysorbates such as polyoxyethylene (20) sorbitan monolaurate, polyoxyethylene (20) sorbitan monopalmitate, polyoxyethylene (20) sorbitan monostearate (available under the trademark TWEEN NED 20, 40, 60, etc.); benzalkonium chloride, mixed chain phospholipids, cationic lipids, oligolipids, phospholipids, carnitines, sphingosines, sphingomyelins, ceramides, glycolipids, lipoproteins, apoproteins, amphiphilic proteins, amphiphilic peptides, and amphiphilic synthetic polymers, and combinations thereof. Other exemplary surface active agents for use herein include, but are not limited to:

i) Natural lipids, i.e. Cholesterol, Sphingosine and Derivatives, Gangliosides, Sphingosine derivatives (Soy Bean), Phytosphingosine and derivatives (Yeast), Choline (Phosphatidylcholine), Ethanolamine (Phosphatidylethanolamine), Glycerol (Phosphatidyl-DL-glycerol), Inositol (Phosphatidylinositol), Serine (Phosphatidylserine (Sodium Salt)), Cardiolipin, Phosphatidic Acid, Egg Derived, Lyso (Mono Acyl) Derivatives (Lysophosphatides), Hydrogenated Phospholipids, Lipid Tissue Extracts, ii) Synthetic lipids, i.e. Asymmetric Fatty Acid, Symmetric Fatty Acid-Saturated Series, Symmetric Fatty Acid-Unsaturated Series, Acyl Coenzyme A (Acetoyl Coenzyme A, Butanoyl Coenzyme A, Crotanoyl Coenzyme A, Hexanoyl Coenzyme A, Octanoyl Coenzyme A, Decanoyl Coenzyme A, Lauroyl Coenzyme A, Myristoyl Coenzyme A, Palmitoyl Coenzyme A, Stearoyl Coenzyme A, Oleoyl Coenzyme A, Arachidoyl Coenzyme A, Arachidonoyl Coenzyme A, Behenoyl Coenzyme A, Tricosanoyl Coenzyme A, Lignoceroyl Coenzyme A, Nervonoyl Coenzyme A, Hexacosanoyl Coenzyme A, iii) Sphingolipids, i.e. D-erythro (C-18) Derivatives (Sphingosine, such as: D-erythro Sphingosine (synthetic), Sphingosine-1-Phosphate, N,N Dimethylsphingosine, N,N, N-Trimethylsphingosine, Sphingosylphosphorylcholine, Sphingomyelin and Glycosylated Sphingosine), Ceramide Derivatives (Ceramides, D-erythro Ceramide-1-Phosphate, Glycosulated Ceramides), Sphinganine (Dihydrosphingosine) (Sphinganine-1-Phosphate, Sphinganine (C20), D-erythro Sphinganine, N-Acyl-Sphinganine C2, N-Acyl-Sphinganine C8, N-acyl-Sphinganine C16, N-Acyl-Sphinganine C18, N-Acyl-Sphinganine C24, N-Acyl-Sphinganine C24:1), Glycosylated (C18) Sphingosine and Phospholipid Derivatives (Glycosylated-Sphingosine) (Sphingosine, β D-Glucosyl, Sphingosine, β D-Galactosyl, Sphingosine,β D-Lactosyl), Glycosylated-Ceramide (D-Glucosyl-β1-1' Ceramide (C8), D-Galactosyl-β1-1' Ceramide (C8), D-Lactosyl-β1-1' Ceramide (C8), D-Glucosyl-β1-1' Ceramide (C12), D-Galactosyl-β1-1' Ceramide (C12), D-Lactosyl-β1-1' Ceramide (C12)), Glycosylated-Phosphatidylethanolamine (1,2-Dioleoyl-sn-Glycero-3-Phosphoethanolamine-N-Lactose), D-erythro (C17) Derivatives (D-erythro Sphingosine, D-erythro Sphingosine-1-phosphate), D-erythro (C20) Derivatives (D-erythro Sphingosine), L-threo (C18) Derivatives (L-threo Sphingosine, Safingol (L-threo Dihydrosphingosine)), Sphingosine Derivatives (Egg, Brain & Milk) (D-erythro-Sphingosine, Sphingomyelin, Ceramides, Cerebrosides, Brain Sulfatides), Gangliosides (Gangliosides Structures, Gangliosides-Ovine Brain, Gangliosides-Porcine Brain), Sphingosine Derivatives (Soy Bean) (Glucosylceramide), Phytosphingosine Derivatives (Yeast) (Phytosphingosine, D-ribo-Phytosphingosine-1-Phosphate, N-Acyl Phytosphingosine C2, N-Acyl Phytosphingosine C8, N-Acyl Phytosphingosine C18, iv) Acyl coenzyme A, i.e. Acetoyl Coenzyme A (Ammonium Salt), Butanoyl Coenzyme A (Ammonium Salt), Crotanoyl Coenzyme A (Ammonium Salt), Hexanoyl Coenzyme A (Ammonium Salt), Octanoyl Coenzyme A (Ammonium Salt), Decanoyl Coenzyme A (Ammonium Salt), Lauroyl Coenzyme A (Ammonium Salt), Myristoyl Coenzyme A (Ammonium Salt), Palmitoyl Coenzyme A (Ammonium Salt), Stearoyl Coenzyme A (Ammonium Salt), Oleoyl Coenzyme A (Ammonium Salt), Arachidoyl Coenzyme A (Ammonium Salt), Arachidonoyl Coenzyme A (Ammonium Salt), Behenoyl Coenzyme A (Ammonium Salt), Tricosanoyl Coenzyme A (Ammonium Salt), Lignoceroyl Coenzyme A (Ammonium Salt), Nervonoyl Coenzyme A (Ammonium Salt), Hexacosanoyl Coenzyme A (Ammonium Salt), Docosahexaenoyl Coenzyme A (Ammonium Salt), v) Oxidized lipids, i.e. 1-Palmitoyl-2-Azelaoyl-sn-Glycero-3-Phosphocholine, 1-O-Hexadecyl-2-Azelaoyl-sn-Glycero-3-Phosphocholine, 1-Palmitoyl-2-Glutaroyl-sn-Glycero-3-Phosphocholine (PGPC), 1-Palmitoyl-2-(9'-oxo-Nonanoyl)-sn-Glycero-3-Phosphocholine, 1-Palmitoyl-2-(5'-oxo-Valeroyl)-sn-Glycero-3-Phosphocholine, vi) Ether lipids, i.e. Diether Lipids (Dialkyl Phosphatidylcholine, Diphytanyl Ether Lipids), Alkyl Phosphocholine (Dodedylphosphocholine), O-Alkyl diacylphosphatidylcholinium (1,2-Diacyl-sn-Glycero-3-Ethylphosphocholine), Synthetic PAF & Derivatives (1-Alkyl-2-Acyl-Glycero-3-Phosphocholine & Derivatives), vii) Fluorescent lipids, i.e. Glycerol Based (Phosphatidylcholine (NBD), Phosphatidic Acid (NBD), Phosphatidylethanolamine (NBD), Phosphatidylglycerol (NBD), Phosphatidylserine (NBD)), Sphingosine Based (Ceramide (NBD), Sphingomyelin (NBD), Phytosphingosine (NBD), Galactosyl Cerebroside (NBD)), Headgroup Labeled Lipids (Glycerol Based) (Phosphatidylethanolamine (NBD), Phosphatidylethanolamine (Lissamine Rhodamine B), Dioleoyl Phosphatidylethanolamine (Dansyl, Pyrene, Fluorescein), Phosphatidylserine (NBD), Phosphatidylserine (Dansyl)), 25-NBD-Cholesterol, viii) Other lipids including, but not limited to Lecithin, Ultralec-P (ADM), Soy powder, and ix) Surfactants including, but not limited to polyethylene glycol 400; sodium lauryl sulfate; sorbitan laurate, sorbitan palmitate, sorbitan stearate (available under the trademark Span® 20-40-60 etc.); polysorbates such as polyoxyethylene (20) sorbitan monolaurate, polyoxyethylene (20) sorbitan monopalmitate, polyoxyethylene (20) sorbitan monostearate (available under the trademark TWEEN® 20-40-60 etc.); benzalkonium chloride.

In certain embodiments, the phospholipids for use herein are phosphatidylcholines, phosphatidylethanolamines, phosphatidylserines, phosphatidylglycerols, phosphatidylinositols, phosphatidic acids, mixed chain phospholipids, lysophospholipids, hydrogenated phospholipids, partially hydrogenated phospholipids, and mixtures thereof.

In certain embodiments, the surface active agent is selected from polysorbate-80, lecithin and phosphatidylcholine. The surface active agents are present in an amount sufficient to form a stable emulsion.

The amount of surface active agent can be empirically determined and is a function of the agent selected and the desired form of the resulting composition. The amount included can be from less than 0.1% by weight up to 35% or more. In certain embodiments, the surface active agent is present at a concentration of about 1%, 2%, 3%, 4%, 5%, 6%, 7%, 8%, 9%, 10%, 15%, 20% or 25% by weight up to about 30% by weight of the total weight of the composition.

In certain embodiments, the surface active agent is present at a concentration of about 1% by weight up to about 20% by weight of the total weight of the composition. In certain embodiments, the surface active agent is present at a concentration of about 1% by weight up to about 15% by weight of the total weight of the composition. In other embodiments, the surface active agent is present at a concentration of about 1% by weight up to about 10% by weight of the total weight of the composition. In other embodiments, the surface active agent is present at a concentration of about 1% by weight up to about 8% by weight of the total weight of the composition. In other embodiments, the surface active agent is present at a concentration of about 1% by weight up to about 6% by weight of the total weight of the composition. In other embodiments, the surface active agent is present at a concentration of about 1% by weight up to about 4% by weight of the total weight of the composition. In other embodiments, the surface active agent is present at a concentration of about 20% by weight of the total weight of the composition. In other embodiments, the surface active agent is present at a concentration of about 15% by weight of the total weight of the composition. In other embodiments, the surface active agent is present at a concentration of about 13% by weight of the total weight of the composition. In other embodiments, the surface active agent is present at a concentration of about 11% by weight of the total weight of the composition. In other embodiments, the surface active agent is present at a concentration of about 8% by weight of the total weight of the composition. In other embodiments, the surface active agent is present at a concentration of about 6% by weight of the total weight of the composition. In other embodiments, the surface active agent is present at a concentration of about 4% by weight of the total weight of the composition. In other embodiments, the surface active agent is present at a concentration of about 2% by weight of the total weight of the composition. In other embodiments, the surface active agent is present at a concentration of about 1% by weight of the total weight of the composition.

The stable emulsions provided herein can contain one or more delivery vehicles selected from among micelles, liposomes and cubosomes and mixtures thereof, that encapsulate the probiotic. The compositions do not include any PEG derivatives of vitamin E.

5. Polymers

The compositions optionally contain one or more polymers that modify the viscosity of the composition. In certain embodiments, the polymers for use herein are selected from homopolymers such as polyolefins including polyethylene, polypropylene, polybutene, and polymers of higher alpha-olefins; styrenic polymers including polystyrene, polymers made from styrene monomers with pendant alkyl groups such as poly(alpha-methylstyrene) and poly(para-methyl styrene), and halogenated versions of the above styrenic polymers; polydienes including polybutadiene, polyisoprene, and other polymers made from alkylated diene monomers; polyamides; polyimides; polycarbonates; polyisobutylene; acrylics such as poly(methyl methacrylate), poly(butyl methacrylate), poly(acrylic acid); silicones such as poly(dimethyl siloxane); polysulfones; vinyl polymers such as poly(vinyl chloride), poly(vinyl fluoride), poly(vinyl alcohol), poly(vinyl phenol), poly(vinylidene chloride), poly(vinylidene fluoride), poly(tetrafluoro ethylene), poly(acrylonitrile); polyesters including poly(ethylene glycol) esters, poly(ethylene terephthalate), poly(butylene terephthalate); polyethers including poly(ethylene oxide), poly(propylene-oxide), poly(oxymethylene; poly(phenylene oxide); poly(phenylene sulfide); poly(acrylates); poly(benzimidazoles; and other polymers made from polymerizable monomers; statistical copolymers of the monomers or repeat units described above including for example copolymers of ethylene with other monomers such as alpha-olefins including propylene, butene-1, hexene, octene; dienes; vinyl acetate; vinyl alcohol; vinyl chloride; vinylidene chloride; copolymers of isobutylene with other monomers including isoprene, butadiene, para methylstyrene, styrene; copolymers of styrene with other monomers including butadiene, isoprene, maleic anhydride, acrylonitrile, oxazoline; copolymers of butadiene with other monomers including acrylonitrile; copolymers of propylene with other monomers including ethylene, butene, hexane and dienes; block copolymers made from units of any of the above homopolymers or copolymers including styrene-diene block polymers such as styrene-isoprene-styrene triblock copolymer, styrene-butadiene-styrene triblock copolymers, styrene-ethylene/propylene-styrene triblock copolymers (all ratios of ethylene to propylene); graft copolymers made from units of any of the above homopolymers or copolymers including poly(ethylene-graft-propylene), poly(styrene-graft-butadiene); and derivatized versions of any of the above homopolymers or copolymers including for example those made by sulfonation, amination, and carboxylation, such as sulfonated polystyrene, sulfonated ethylene-propylene-diene monomer.

Generally the identity and composition (i.e., the ratio or amount of each type of copolymer unit desired) of the copolymer can be varied depending on the characteristics desired in the end product. It is within the skill of one skilled in the art to make such selections.

In certain embodiments, the polymer for use herein is polyethylene glycol ester. In certain embodiments, the polyethylene glycol ester is selected from PEG 200 monolaurate, PEG 200 dilaurate, PEG 300 monolaurate, PEG 300 dilaurate, PEG 400 monolaurate, PEG 600 dilaurate, PEG 600 monolaurate, PEG 200 dilaurate, PEG 1000 monolaurate, PEG 1000 dilaurate, PEG 1540 monolaurate, PEG 1540 dilaurate, PEG 4000 monolaurate, PEG 4000 dilaurate, PEG 6000 monolaurate, PEG 6000 dilaurate, PEG 200 monostearate, PEG 200 distearate, PEG 300 monostearate, PEG 300 distearate, PEG 400 monostearate, PEG 600 distearate, PEG 600 monostearate, PEG 200 distearate, PEG 1000 monostearate, PEG 1000 distearate, PEG 1540 monostearate, PEG 1540 distearate, PEG 4000 monostearate, PEG 4000 distearate, PEG 6000 monostearate, PEG 6000 distearate, PEG 200 monooleate, PEG 200 dioleate, PEG 300 monooleate, PEG 300 dioleate, PEG 400 monooleate, PEG 600 dioleate, PEG 600 monooleate, PEG 200 dioleate, PEG 1000 monooleate, PEG 1000 dioleate, PEG 1540 monooleate, PEG 1540 dioleate, PEG 4000 monooleate, PEG 4000 dioleate, PEG 6000 monooleate and PEG 6000 dioleate.

In certain embodiments, the polymer used herein is PEG 400 distearate. In certain embodiments, PEG 400 distearate is present at a concentration of about 0.1% by weight up to about 10% by weight of the total weight of the composition. In other embodiments, PEG 400 distearate is present at a concentration of about 0.1% by weight up to about 8% by weight of the total weight of the composition. In other embodiments, PEG 400 distearate is present at a concentration of about 0.1% by weight up to about 6% by weight of the total weight of the composition. In other embodiments, PEG 400 distearate is present at a concentration of about 0.1% by weight up to about 4% by weight of the total weight of the composition. In other embodiments, PEG 400 distearate is present at a concentration of about 0.1% by weight up to about 2% by weight of the total weight of the composition. In other embodiments, PEG 400 distearate is present at a concentration of about 2% by weight of the total weight of the composition. In other embodiments, PEG 400 distearate is present at a concentration of about 1.8% by weight of the total weight of the composition. In other embodiments, PEG 400 distearate is present at a concentration of about 1.5% by weight of the total weight of the composition. In other embodiments, PEG 400 distearate is present at a concentration of about 1% by weight of the total weight of the composition. In other embodiments, PEG 400 distearate is present at a concentration of about 0.1% by weight of the total weight of the composition.

6. Cosolvents

The compositions provided herein can also contain one or more cosolvents. Such cosolvents are non-toxic, pharmaceutically acceptable substances, typically liquids, which do not substantially negatively affect the solubility of the active agents at the concentrations used. The cosolvent can aid in dissolving the active agent or for the mucoadhesive materials, or both. The cosolvent in certain embodiments, is a polyhydric alcohol or combination of polyhydric alcohols. In certain embodiments, the cosolvent is ethylene glycol, dipropylene glycol, propylene glycol, polyethylene glycol, glycerin, butylene glycol, hexylene glycol, polyoxyethylene, polypropylene glycol, sorbitol, ethylene glycol, or a mixture thereof. As discussed above, the cosolvent can be glycerin, but this is in addition to the glycerin employed as the polar protic solvent.

The amount of cosolvent in the compositions provided herein depends on the solubility of the active agent and/or the mucoadhesive substance in the oil or polar protic solvent, other than water, phase. Typically, the cosolvent is present in an amount sufficient to achieve complete dissolution of the active agent. In certain embodiments, the cosolvent is propylene glycol and is present at a concentration of about 1% by weight up to about 30% by weight of the total weight of the total composition. In other embodiments, propylene glycol is present at a concentration of about 1% by weight up to about 20% by weight of the total weight of the total composition. In other embodiments, propylene glycol is present at a concentration of about 1% by weight up to about 15% by weight of the total weight of the total composition. In other embodiments, propylene glycol is present at a concentration of about or at least 1% by weight up to about 10% by weight of the total weight of the total composition. In other embodiments, propylene glycol is present at a concentration of about 15% by weight of the total weight of the total composition. In other embodiments, propylene glycol is present at a concentration of about or at least 13% by weight of the total weight of the total composition. In other embodiments, propylene glycol is present at a concentration of about or at least 11% by weight of the total weight of the total composition. In other embodiments, propylene glycol is present at a concentration of about or at least 9.5% by weight of the total weight of the total composition. In other embodiments, propylene glycol is present at a concentration of about or at least 7.5% by weight of the total weight of the total composition. In other embodiments, propylene glycol is present at a concentration of about or at least 5% by weight of the total weight of the total composition. In other embodiments, propylene glycol is present at a concentration of about or at least 3% by weight of the total weight of the total composition. In other embodiments, propylene glycol is present at a concentration of about or at least 1% by weight of the total weight of the total composition.

7. Binders

The compositions further can contain at least one excipient. Excipients include, but are not limited to, diluents (sometimes referred to as fillers) including, for example, microcrystalline cellulose, mannitol, lactose, calcium phosphate, dextrates, dextrins, including cluster dextrins, maltodextrin, starch, sucrose, and pregelatinized starch; disintegrants including, for example, crospovidone, sodium starch glycolate, croscarmellose sodium, starch, pregelatinized starch, and carboxymethylcellulose sodium; binders including, for example, starch, hydroxypropyl cellulose, hydroxypropylmethyl cellulose, pregelatinized starch, guar gum, alginic acid, acacia, carboxymethylcellulose sodium, and polyvinyl pyrrolidone; glidants including, for example, colloidal silicon dioxide and talc; and lubricants/antiadherents including, for example, magnesium stearate, calcium stearate, stearic acid, sodium stearyl fumarate, glyceryl monostearate, hydrogenated vegetable oil, and talc. In one particular example, the excipients are selected from any one or more of maltodextrin and gum acacia.

8. Other Additives

The compositions provided herein can further contain one or more other additives such as taste modifying agents, a buffering agent, a chelating agent, a colorant, an osmotic modifier, a solubilizer, a tonicifier, a trace element, and a viscomodulator. Additional agents do not include any that are harmful to probiotic microorganisms.

Taste modifying agents for use herein include, but are not limited to flavoring agents, sweetening agents and taste masking agents and are exemplified by: the essential oils or water soluble extracts of menthol, wintergreen, peppermint, sweet mint, spearmint, natural and artificial vanilla, cherry, chocolate, fudge, butterscotch, cinnamon, clove, lemon, orange, raspberry, rose, spice, violet, herbal, fruit, strawberry, grape, pineapple, peach, kiwi, *papaya*, mango, coconut, apple, coffee, plum, watermelon, nuts, durean, green tea, grapefruit, banana, butter, cream custard, camomile, sugar, dextrose, lactose, mannitol, sucrose, xylitol, maltitol, acesulfame potassium, talin, glycyrrhizin, sucralose, aspartame, saccharin, sodium saccharin, sodium cyclamate and honey. In certain embodiments, the taste modifying agent is selected from natural and artificial vanilla, cream custard, banana, fudge, butterscotch, coconut and chocolate. Many such agents are commercially available.

Buffering agents and pH adjusters include, but are not limited to acidulants and alkalizing agents exemplified by citric acid, fumaric acid, lactic acid, tartaric acid, malic acid, as well as sodium citrate, sodium bicarbonate and carbonates, including $KHCO_3$, sodium or potassium phosphate and magnesium oxide. pH adjuster-1 is triethanolamine or potassium bicarbonate, pH adjuster-2 is soda ash or sodium bicarbonate. The particular pH at which the compositions are formulated depends upon the selected agent(s). For example, the emulsions generally have a pH compatible with maintaining viability of the miroorganism, typically, between about 7 and 8. Coloring agents for use in the compositions include, but are not limited to FD & C coloring agents, natural coloring agents, and natural juice concentrates, pigments such as titanium oxide, silicon dioxide and zinc oxide.

Stabilizers as used in the compositions provided herein, include, but are not limited to anti-oxidants, chelating agents, and enzyme inhibitors as exemplified by ascorbic acid, vitamin E, butylated hydroxyanisole (BHA), butylated hydroxytoluene (BHT), propyl gallate, dilauryl thiodipropionate, thiodiproprionic acid, gum guaiac, citric acid, edetic acid and its salts and glutathione.

The compositions can contain preservatives which include, but are not limited to benzyl alcohol, sodium benzoate, potassium sorbate, parabens and derivatives, such as methyl paraben, propyl paraben, sorbic acid and its salts, propionic acids and its salts, sulfur dioxide and sulfites, acetic acid and acetates, and nitrites and nitrates.

The compositions can contain suitable sweeteners and flavorings.

C. EXEMPLARY COMPOSITIONS AND THEIR PREPARATION

The compositions provided herein are emulsions and powders produced by drying, generally spray-drying the emulsions. The following sections describe the emulsions and powders in more detail.

1. Preparation of the Emulsions

The ingredients in the emulsions prepared as described above and in the examples, contain the lactoferrin and probiotic; an oil, such as MCT oil, a surfactant, such as a sucrose fatty acid ester (SFAE) (sold under the trademark DK Ester® by Dai-Ichi Kogyo Seiyaku Co., Ltd, Japan); optionally an emulsion stabilizer, such as a blend of xanthan gum, guar gum and sodium alginate, such as those sold under the trademark SALADIZER®, available from TIC Gums, Inc. (Belcamp, Md.); a binder, such as maltodextrin (sold by Archer Daniels Midland Company, Decatur, Ill.) and a highly branched cyclic dextrin (HBCD) (sold under the trademark Cluster Dextrin® by Glico Nutrition, Japan); stabilizers, including vitamin C (sold by Pure Assay Ingredients, Walnut, Calif.), potassium bicarbonate, and green tea extracts that contained 40% or 50% epigallocatechin gallate (EGCG) (Guilin Layn Natural Ingredients, Corp., Guilin, China); sweeteners that included erythritol, *stevia* (sold under the trademark Stevia® Leaf Powder Extract, Product code STE091, by MiniStar International Inc.), and sorbitol; flavor agents that included pink grapefruit, natural mandarin orange (346316), natural watermelon (600171), and natural sour yuzu (347528), all sold by Gold Coast Ingredients, Inc. (Commerce, Calif.), natural fresh orange (L-17283), natural blueberry (BL-238), natural watermelon (WM-122), and natural sour yuzu (L-20609), all sold by Mission Flavors and Fragrances, Inc. (Foothill Ranch, Calif.), natural orange tangerine (DABJ826) and natural blueberry pomegranate (DABJ831), sold by Wild Flavors (Erlanger, Ky.), and green tea flavor, sold by Kerry, Inc. (Beloit, Wis.); a pH adjuster, citric acid; and a polar solvent, water, which was purified city water, purified as described above.

In general, emulsions (e.g., oil-in-water emulsions) are colloidal dispersions of two immiscible liquids (e.g., oil and water or other aqueous liquid), containing a continuous and a dispersed phase. Emulsions can be used to disperse non-polar ingredients in aqueous liquids. In an oil-in-water emulsion, the dispersed phase is an oil phase and the continuous phase is an aqueous (water) phase. There is a need for emulsions (e.g., oil-in-water emulsions) containing non-polar ingredients in aqueous liquids and methods and compositions for generating products, such as the water-soluble powders, that are free-flowing, i.e., not sticky. In particular, emulsions are needed that are more suitable and desirable for human consumption of the non-polar ingredients, for example, beverages. For example, emulsions having improved clarity (e.g., small particle size, low turbidity), stability (e.g., lack of separation), taste and smell, that can form powders that are free-flowing, i.e., not sticky, and water-soluble are provided herein.

Typically, the provided emulsions containing the concentrates containing non-polar ingredients are nanoemulsions, which are emulsions having dispersed droplets (particles) with diameters less than 1000 nm or less than about 1000 nm, typically, less than 500 nm or less than about 500 nm, typically less than 300 nm or about 300 nm, typically less than 250 or less than about 250 nm, typically less than 200 nm or less than about 200 nm, for example, less than or less than about 5, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 110, 120, 130, 140, 150, 160, 170, 180, 190, or 200 nm. Typically, the provided nanoemulsion compositions are oil-in-water nanoemulsions, containing the non-polar ingredients dispersed in aqueous liquid.

The provided emulsion compositions are stabilized by one or more surfactants and/or co-surfactants and/or emulsion stabilizers. Surfactants form an interfacial film in the emulsion, between the oil and polar phase, providing stability. Typically, the nanoemulsions of the provided compositions contain micelles, in which one or more surfactant surrounds the non-polar compound. The micelles are dispersed in the polar phase.

The provided emulsions contain the pre-emulsion concentrates containing non-polar ingredients and/or probiotics, which can be spray-dried to provide non-polar compounds and/or probiotics in a powder, such as free-flowing, water-soluble powder. The emulsions can be made using any concentrate containing probiotics, a sugar fatty acid ester, and lactoferrin, such as the pre-emulsion concentrates provided herein.

Exemplary concentrations of the total amount of probiotic plus mucoadhesive protein, such as lactoferrin in the emulsions are at or at least about 5%, 7%, 10%, 12%, 15%, 17%, 20%, 22%, or 25% (wt %) of the emulsion, such as about or at 10% (wt %) of the emulsion. The amount of surfactant, such as SFAE is about 3-10%. The amount of oil, such as MCT oil, is about or is 10-20%, by weight, the amount of binder, such as dextrin or maltodextrin, is 4-20%, the amount of polar solvent, such as water is about 40%-65%, the amount of stabilizer, such as $KHCO_3$, ascorbic acid, or bicarbonate and mixtures thereof is about 0.1% to 5%, such as about or at 1-5% or 3-5%, by weight of the emulsion composition.

a. Formulating the Emulsions

In the provided methods, the emulsions are formulated by selecting ingredients and concentration ratios of the ingredients that yield compositions having one or more desired properties. The ingredients typically include a concentrate that contains lactoferrin, probiotic, a surfactant, such as a sugar fatty acid ester, e.g., sucrose fatty acid ester; and a polar solvent, e.g., water. In some examples, the emulsions further include one or more of a stabilizer, a binder, e.g., maltodextrin, a co-surfactant, an emulsion stabilizer, and a pH adjuster. In the provided emulsions, a surfactant, such as a sugar fatty acid ester, e.g., sucrose fatty acid ester, is present in place of or in combination with a binder, e.g., maltodextrin. For example, the emulsions provided herein can contain a surfactant, such as such as a sugar fatty acid ester, e.g., sucrose fatty acid ester, and not contain a binder, e.g., maltodextrin. In other examples, the emulsions provided herein contain a mixture of surfactant, such as a sugar fatty acid ester, e.g., sucrose fatty acid ester, and binder, e.g., maltodextrin.

b. Exemplary Ingredients and Typical Concentration Ranges

Exemplary ingredients and concentrations also are described in Section B above. Each emulsion provided herein contains probiotics and a mucoadhesive protein, such as lactoferrin. The emulsions contain between about 2% and 15% wt % probiotic, and at least 2% mucoadhesive protein, such as lactoferrin, so that the total amount of the two is between about 5% and 35%, such as about 25% wt % of the powder, and the powder contains at least 5%, by weight, mucoadhesive protein, such as lactoferrin, when the emulsion is spray dried. The mucoadhesive protein, such as lactoferrin plus probiotic is about 5%-20%, such as about 10%-15%, by weight, of the emulsion before the emulsion is spray dried.

i. Surfactants

The provided emulsions contain surfactants. The surfactants herein are not polyalkylene derivatives of vitamin E, including PEG-derivative of vitamin E, nor do the emulsions include any vitamin E derivative. For example, in addition to the pre-emulsion concentrate containing non-polar ingredients and/or probiotics, the emulsions can contain one or more surfactants. In the provided methods for producing the emulsions, the surfactant is added to the polar phase, the oil phase, or to the water and the oil phase. The emulsions further can contain one or more co-surfactants or emulsifiers. Typically, the surfactants are natural surfactants, for example, a surfactant that is G.R.A.S. (generally recognized as safe) by the FDA and/or Kosher certified. In an exemplary embodiment, the surfactant is a sugar-derived surfactant, for example, a sugar fatty acid ester, e.g., sucrose fatty acid ester.

The surfactants aggregate in aqueous liquids, such as in the provided emulsions, to form micelles. The hydrophilic portions of the surfactant molecules are oriented toward the outside of the micelle, in contact with the aqueous medium, while the hydrophobic portions of the surfactant molecules are oriented toward the center of the micelle. The micelles can contain more than one surfactant and/or co-surfactant. Properties of the provided compositions, for example, the particle size of the composition and desirable properties related to the particle size, are influenced by the choice of surfactant and the relative amount (concentration) of surfactant. For example, the HLB of the surfactant can affect particle size, clarity, taste, smell, crystal formation and other properties of the provided compositions, for example, the ability of a emulsion to form a free-flowing, i.e., not sticky, powder after spray-drying the emulsion. Similarly, the concentration of the surfactant compared with the concentrations of other ingredients, particularly compared with the concentration of mucoadhesive protein, such as lactoferrin, and probiotics can affect various desirable properties, for example, the ability to form a free-flowing, i.e., not sticky, powder after spray-drying the emulsion.

Surfactants (and co-surfactants) are molecules that contain hydrophobic and hydrophilic portions. In one example, the hydrophobic portion is a hydrophobic tail and the hydrophilic portion is a hydrophilic head of the surfactant molecule. The HLB value of a surfactant is derived from a semi-empirical formula; HLB values are used to index surfactants according to their relative hydrophobicity and hydrophilicity. An HLB value is a numerical representation of the relative representation of hydrophilic groups and hydrophobic groups in a surfactant or mixture of surfactants. The weight percent of these respective groups indicates properties of the molecular structure. See, for example, Griffin, W. C. *J. Soc. Cos. Chem.* 1:311 (1949).

Surfactant HLB values range from 1-45, while the range for non-ionic surfactants typically is from 1-20. The more lipophilic a surfactant is, the lower its HLB value. Conversely, the more hydrophilic a surfactant is, the higher its HLB value. Lipophilic surfactants have greater solubility in oil and lipophilic substances, while hydrophilic surfactants dissolve more easily in aqueous liquids. In general, surfactants with HLB values greater than 10 or greater than about 10 are called "hydrophilic surfactants," while surfactants having HLB values less than 10 or less than about 10 are referred to as "hydrophobic surfactants." HLB values are known for a number of surfactants.

Exemplary of surfactants that can be used in the provided methods and compositions are surfactants having an HLB value of between 12 or about 12 and 20 or about 20, for example, 12, 13, 14, 15, 16, 17, 18, 19, 20, about 12, about 13, about 14, about 15, about 16, about 17, about 18, about 19 or about 20.

The surfactants typically are, and typically have an HLB value between at or about 12 and at or about 20. Particular examples of suitable surfactants for use in the provided compositions include non-ionic surfactants, such as sugar derived surfactants, including fatty acid esters of sugars and sugar derivatives. For example, sugar fatty acid esters include fatty acid esters of sucrose, glucose, maltose and other sugars, esterified to fatty acids of varying lengths (e.g., varying numbers of carbons). The fatty acids typically have carbon chains between 8 and 28 carbons in length, and typically between 8 and 20, or between 8 and 18 or between 12 and 18, such as, but not limited to, stearic acid (18 carbons), oleic acid (18 carbons), palmitic acid (16 carbons), myristic acid (14 carbons) and lauric acid (12 carbons). Typically, the sugar ester surfactants are sucrose ester surfactants, typically sucrose fatty acid ester surfactants.

The emulsions provided herein contain a surfactant, such as a sugar fatty acid ester, e.g., sucrose fatty acid ester, where the total amount of surfactant, e.g., sucrose fatty acid ester, is typically present in an amount as a percentage (%) by weight of the emulsion (wt %), e.g., from at or about 1 wt % to at or about 20 wt %, such as between or between about 1% and 3%, 1% and 5%, 1% and 7%, 1% and 10%, 1% and 12%, 1% and 15%, 1% and 17%, 1% and 20%, 3% and 5%, 3% and 7%, 3% and 10%, 3% and 12%, 3% and 15%, 3% and 17%, 3% and 20%, 5% and 7%, 5% and 10%, 5% and 12%, 5% and 15%, 5% and 17%, 5% and 20%, 7% and 10%, 7% and 12%, 7% and 15%, 7% and 17%, 7% and 20%, 10% and 12%, 10% and 15%, 10% and 17%, 10% and 20%, 12% and 15%, 12% and 17%, 12% and 20%, 15% and 17%, 15% and 20%, and 17% and 20%, sugar fatty acid ester, e.g., sucrose fatty acid ester, by weight of the powder compositions. Exemplary concentrations of the total amount of sugar fatty acid ester, e.g., sucrose fatty acid ester in the emulsions are at or about or at least 1%, 3%, 5%, 7%, 10%, 12%, 15%, 17%, and 20% (wt %) of the emulsions. Generally, the surfactant is present in the emulsions in an amount between about or at 1% to 10%, such as 2% to 5% by weight.

ii. Sucrose Fatty Acid Ester Surfactants

Sucrose fatty acid ester surfactants contain one or more sucrose fatty acid esters, which are non-ionic surfactants that contain sucrose in the hydrophilic portions and fatty acids in the hydrophobic portions. The sucrose fatty acid esters can be made by well-known methods (see, for example, U.S. Pat. Nos. 3,480,616; 3,644,333; 3,714,144; 4,710,567; 4,898,935; 4,996,309; 4,995,911; 5,011,922 and 5,017,697 and International Patent Application Publication No. WO 2007/082149), typically in an esterification reaction as described below.

Because sucrose contains eight hydroxy (—OH) groups, the esterification reaction can join the sucrose molecule to one fatty acid molecule, or can join it to a plurality of, fatty acid molecules, producing different degrees of esterification, e.g., mono-, di-, tri- and poly- (up to octa-) fatty acid esters, but primarily mono-, di-, and/or tri-esters. The degree of esterification can depend on conditions of esterification. The esterification reaction can be carried out with a single type of fatty acid, or a plurality of fatty acids, such as fatty acids with varying carbon chain lengths, branched and linear fatty acids, and/or saturated or unsaturated fatty acids. The esterification reaction with a single fatty acid can produce a single ester, and typically forms more than one ester, such as mono- di-, tri- and/or poly-esters, formed from one reaction. The relative amounts of mono- di-tri- and/or poly-esters can depend on reaction conditions.

The fatty acid in the sucrose fatty acid ester can be any fatty acid, and can contain between 4 and 28 carbon atoms, typically between 8 and 28 carbon atoms, and typically between 8 and 25 carbon atoms, such as between 8 and 18 carbon atoms, such as 8, 9, 10, 11, 12, 13, 14, 15, 16, 17 and 18 carbon atoms. The fatty acid can be synthetic or naturally occurring, and include linear and branched fatty acids. The fatty acids include, but are not limited to, myristic acid, palmitic acid, stearic acid, oleic acid, caproic acid, capric acid, myristic acid, decanoic acid and pelargonic acid.

Thus, the sucrose fatty acid ester surfactants include sucrose monoesters, diesters, triesters and polyesters, and mixtures thereof, and typically contain sucrose monoesters. The sucrose fatty acid ester surfactants include single fatty acid esters and also include homogeneous mixtures of sucrose esters, containing members with different lengths of fatty acid carbon chain and/or members with different degrees of esterification. For example, the sucrose fatty acid ester surfactants include mixtures of monoesters, diesters, triesters, and/or polyesters. The sugar ester surfactants further include sucrose fatty acid ester analogs and homologs and mixtures thereof.

Sucrose fatty acid esters are compounds having the following formula shown below:

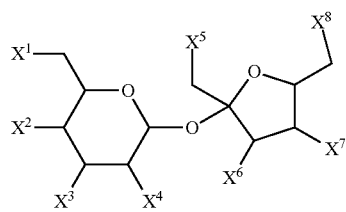

where each of $X^1$, $X^2$, $X^3$, $X^4$, $X^5$, $X^6$, $X^7$ and $X^8$ independently is:
a hydroxyl (—OH) group, or

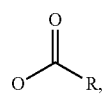

where:
each R is an alkyl group having 3-27 carbon atoms; and

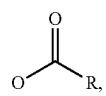

when more than one of $X^1$, $X^2$, $X^3$, $X^4$, $X^5$, $X^6$, $X^7$ and $X^8$ is each R can be a different alkyl group (e.g., having different number of carbon atoms and/or different saturation), or can be the same alkyl group.

Typically, in the provided sucrose fatty acid ester surfactants, each R has between 7 and 27 carbon atoms, and typically between 7 and 19 atoms, such as 7, 8, 9, 10, 11, 12, 13, 14, 15, 16, 17, 18, or 19 carbon atoms or between 7 and 17 carbon atoms.

An alkyl group can be a straight chain or branched alkyl group, can be substituted or unsubstituted, and can be a saturated "saturated alkyl group," meaning that it does not contain any alkene or alkyne groups; or an "unsaturated alkyl group," meaning that it contains at least one alkene or alkyne group. An alkyl group that includes at least one carbon-carbon double bond (C=C) also is referred to by the term "alkenyl," and alkenyl groups optionally can be substituted. An alkyl group that includes at least one carbon-carbon triple bond (C≡C) also is referred to by the term "alkynyl," and alkynyl groups optionally can be substituted.

Typically, the sucrose fatty acid ester surfactants contain sucrose fatty acid monoesters, having the structure set forth below, where one of $X^1$, $X^2$, $X^3$, $X^4$, $X^5$, $X^6$, $X^7$ and $X^8$ (typically $X^1$) is

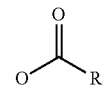

and the other seven of $X^1$, $X^2$, $X^3$, $X^4$, $X^5$, $X^6$, $X^7$ and $X^8$ are each, independently, —OH. An exemplary monoester has the following structure:

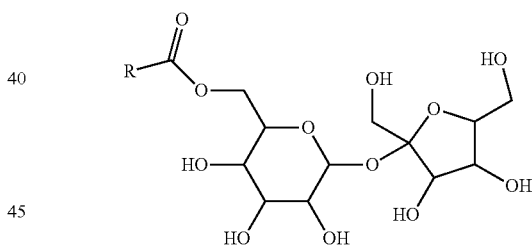

where R is an alkyl group having 3-27 carbons, and typically 7-27 carbons.

The sucrose fatty acid esters include blends of sucrose fatty acid esters, which typically include monoesters, and can also include diesters, triesters and polyesters, which have structures according to Scheme V, above, where two (diesters), three (triesters) or more (polyesters) of $X^1$, $X^2$, $X^3$, $X^4$, $X^5$, $X^6$, $X^7$ and $X^8$, (and typically $X^1$ and $X^8$) independently, are

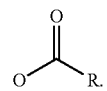

In general, sucrose fatty acid esters, including mixtures of sucrose fatty acid esters, can have varying HLB values, such as HLB values ranging from at or about 1 to at or about 20. The HLB value of the sucrose fatty acid ester generally depends on the degree of esterification (e.g., the average degree of esterification in a mixture of different esters). Typically, the lower the degree of esterification (e.g., average degree), the higher the HLB value of the sucrose fatty acid ester or mixture thereof. Exemplary sucrose esters include sucrose distearate (HLB=3), sucrose distearate/monostearate (HLB 12), sucrose dipalmitate (HLB=7.4); sucrose monostearate (HLB=15), sucrose monopalmitate (HLB>10); sucrose monolaurate (HLB 15). Typically, the sucrose fatty acid ester surfactants in the provided compositions have an HLB value of between at or about 14 and at or about 20, such as at or about 14, 15, 16, 17, 18, 19, or 20, and typically between at or about 14 and at or about 18, such as, but not limited to, HLB values of at or about 15, 16 and 17, such as, for example, sucrose ester surfactants including sucrose monopalmitate, sucrose monolaurate and sucrose monostearate.

The sugar ester surfactants include sucrose ester blends, for example, sucrose ester mixtures containing a specified amount (e.g., percent, by weight) of sucrose monoesters. Exemplary surfactants include sucrose ester mixtures having at least at or about 50%, by weight (w/w), monoester, such as at or about or at least at or about 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100%, by weight (w/w), sucrose monoesters, and typically at least at or about 60%, by weight or at least at or about 70%, by weight (w/w), monoesters. The surfactants include mixtures of sucrose esters containing at least at or about 50% sucrose monoesters, mixtures of sucrose esters containing at least at or about 60% sucrose monoesters, mixtures of sucrose esters containing at least at or about 70% sucrose monoesters, mixtures of sucrose esters containing at least at or about 80% sucrose monoesters, and mixtures of sucrose esters containing at least at or about 90% sucrose monoesters, for example, mixtures containing at or about 72% sucrose monoesters, at or about 61% sucrose monoesters, or at or about 90% sucrose monoesters.

The sucrose fatty acid ester surfactants include sucrose fatty acid monoesters, such as sucrose monocaprylate, sucrose monodecanoate, sucrose monolaurate, sucrose monomyristate, sucrose monopalmitate, sucrose monostearate, sucrose monopelargonate, sucrose monoundecanoate, sucrose monotridecanoate, sucrose monopentadecanoate and sucrose monoheptadecanoate. The sucrose fatty acid esters further include mixtures containing varying percentages of monoesters, diesters, triesters and polyesters, such as, but not limited to, a mixture having at or about 72% monoesters, 23% diesters, 5% triesters and 0% polyesters; a mixture having at or about 61% monoesters, 30% diesters, 7% triesters, and 2% polyesters; and a mixtures having at or about 52% monoesters, 36% diesters, 10% triesters and 2% polyesters.

The sucrose fatty acid ester surfactants include sucrose fatty acid esters sold under the trademark DK Ester®, produced by Dai-Ichi Kogyo Seiyaku Co., Ltd of Japan (which, in some examples, can be produced according to the methods described in U.S. Pat. Nos. 4,898,935; 4,996,309; 4,995,911; 5,011,922 and 5,017,697, and distributed through Montello Inc., Tulsa, Okla.), such as the F-160 and F-140 grade esters sold under the trademark DK Ester®, and sucrose esters sold under the trademark SURFHOPE® SE PHARMA, by Mitsubishi-Kagaku Foods Corporation, distributed by Mitsubishi Chemical Performance Polymers, Inc. These sucrose fatty acid esters are mixtures of esters with different degrees of esterification. The sucrose fatty acid esters further include Ryoto™ sugar esters, which are food-grade esters sold by Mitsubishi-Kagaku Foods Corporation, distributed by Mitsubishi Chemical Performance Polymers, Inc. Exemplary sucrose fatty acid esters sold under the trademark DK Ester®, and those sold under the trademarks SURFHOPE® SE PHARMA and Ryoto™ sugar esters, are listed in the table below. The table lists the average degree of esterification or the fatty acid composition within the mixture, and the HLB of the sucrose fatty acid ester surfactant. Any of the surfactants in the table below can be used. Typically, the surfactant (e.g., a surfactant listed in the table below), has an HLB value between at or about 12 and at or about 20, typically between at or about 15 and at or about 18, e.g., but not limited to, those surfactants in the table having an HLB of 15 or 16, such as the sucrose fatty acid ester surfactant sold under the trade mark DK ESTER® F-160, produced by Dai-Ichi Kogyo Seiyaku Co., Ltd of Japan, and distributed through Montello Inc., Tulsa, Okla. Other exemplary sucrose fatty acid ester surfactants are described in Youan et al., AAPS PharmaSci 2003; 5(2) Article 22; 1-9 and in Okamoto et al., Biol. Pharm. Bull. 28(9): 1689-1694 (2005).

Exemplary Sucrose Fatty Acid Ester (SFAE) Surfactants

| Sucrose Fatty Acid Ester trademark and catalog number | Average Degree of Esterification | Fatty acid composition | H.L.B. | Distribution (by weight) of Ester Mono:Di:Tri:Poly |
|---|---|---|---|---|
| DK Ester ® F-160 | 1.23 | | 16 | 72% monoester; 23% diester; 5% triester |
| DK Ester ® F-140 | 1.35 | | 13 | 61% monoester; 30% diester; 7% triester; 2% polyester |
| DK Ester ® F-110 | 1.48 | | 11 | 52% monoester; 36% diester; 10% triester; 2% polyester |
| DK Ester ® F-90 | 1.53 | | 9.5 | 45% monoester; 39% diester; 12% triester; 4% polyester |
| DK Ester ® F-70 | 1.60 | | 8 | 39% monoester; 45% diester; 12% triester; 4% polyester |
| DK Ester ® F-50 | 1.69 | | 6 | 34% monoester; 46% diester; 17% triester; 3% polyester |
| DK Ester ® F-20W | 3.11 | | 2 | 11% monoester; 21% diester; 14% triester; 54% polyester |

-continued

| Sucrose Fatty Acid Ester trademark and catalog number | Average Degree of Esterification | Fatty acid composition | H.L.B. | Distribution (by weight) of Ester Mono:Di:Tri:Poly |
|---|---|---|---|---|
| DK Ester ® F-10 | 4.85 | | 1 | 0% monoester; 5% diester; 11% triester; 84% polyester |
| SURFHOPE ® SE PHARMA J-1205 | | C12 (100%) | 5 | 32% monoester; 68% di-/tri-/poly-esters |
| SURFHOPE ® SE PHARMA J-1216 | | C12 (100%) | 16 | 81% monoester; 19% di-/tri-/poly-esters |
| SURFHOPE ® SE PHARMA J-1616 | | C16 (80%); C18 (20%) | 16 | 79% monoester; 21% di-/tri-/poly-esters |
| SURFHOPE ® SE PHARMA J-1805 | | C16 (70%); C18 (30%) | 5 | 30% monoester; 70% di-/tri-/poly-esters |
| SURFHOPE ® SE PHARMA J-1807 | | C16 (70%); C18 (30%) | 7 | 41% monoester; 59% di-/tri-/poly-esters |
| SURFHOPE ® SE PHARMA J-1816 | | C16 (70%); C18 (30%) | 16 | 75% monoester; 25% di-/tri-/poly-esters |
| SURFHOPE ® SE PHARMA D-1803 | | Sucrose stearate (approximately 70% stearate) | 3 | Approximately 20% monoester; approximately 80% di-/tri-/poly-esters |
| SURFHOPE ® SE PHARMA D-1803F | | Sucrose stearate (70% stearate) | 3 | 20% monoester; 80% di-/tri-/poly-esters |
| SURFHOPE ® SE PHARMA D-1805 | | Sucrose stearate (70% stearate) | 5 | 30% monoester; 70% di-/tri-/poly-esters |
| SURFHOPE ® SE PHARMA D-1807 | | Sucrose stearate (70% stearate) | 7 | 40% monoester; 60% di-/tri-/poly-esters |
| SURFHOPE ® SE PHARMA D-1809 | | Sucrose stearate (70% stearate) | 9 | 50% monoester; 50% di-/tri-/poly-esters |
| SURFHOPE ® SE PHARMA D-1811 | | Sucrose stearate (70% stearate) | 11 | 55% monoester; 45% di-/tri-/poly-esters |
| SURFHOPE ® SE PHARMA D-1811F | | Sucrose stearate (70% stearate) | 11 | 55% monoester; 45% di-/tri-/poly-esters |
| SURFHOPE ® SE PHARMA D-1815 | | Sucrose stearate (70% stearate) | 15 | 70% monoester; 30% di-/tri-/poly-esters |
| SURFHOPE ® SE PHARMA D-1816 | | Sucrose stearate (70% stearate) | 16 | 75% monoester; 25% di-/tri-/poly-esters |
| SURFHOPE ® SE PHARMA D-1615 | | Sucrose palmitate (80% palmitate) | 15 | 70% monoester; 30% di-/tri-/poly-esters |
| SURFHOPE ® SE PHARMA D-1616 | | Sucrose palmitate (80% palmitate) | 16 | 80% monoester; 20% di-/tri-/poly-esters |
| SURFHOPE ® SE PHARMA D-1216 | | Sucrose laurate (95% laurate) | 16 | 80% monoester; 20% di-/tri-/poly-esters |
| Ryoto ™ S-970 | | Sucrose stearate | 9 | 50% monoester |
| Ryoto ™ S-1170 | | Sucrose stearate | 11 | 55% monoester |
| Ryoto ™ S-1570 | | Sucrose stearate | 15 | 70% monoester |
| Ryoto ™ S-1670 | | Sucrose stearate | 16 | 75% monoester |
| Ryoto ™ P-1570 | | Sucrose palmitate | 15 | 70% monoester |
| Ryoto ™ P-1670 | | Sucrose palmitate | 16 | 80% monoester |
| Ryoto ™ LWA-1570 | | Sucrose laurate | 15 | 70% monoester |
| Ryoto ™ L-1695 | | Sucrose laurate | 16 | 80% monoester |
| Ryoto ™ OWA-1570 | | Sucrose oleate | 15 | 70% monoester | iii. Production of Sucrose Esters

As noted above, methods for producing sucrose esters are well known (see, for example, U.S. Pat. Nos. 3,480,616; 3,644,333; 3,714,144; 4,710,567; 4,898,935; 4,996,309; 4,995,911; 5,011,922 and 5,017,697 and International Patent Application, Publication No. WO 2007/082149). The sucrose fatty acid surfactants can be produced by any known method, and typically are produced in an esterification reaction, for example, by reacting sucrose with a methyl ester of the desired fatty acid, such as a solvent process, where sucrose is reacted with a methyl ester of a fatty acid in the presence of a catalyst (e.g., potassium carbonate) and an organic solvent (e.g., dimethyl formamide (DMF) or dimethyl sulfoxide (DMSO)), followed by purification, or in an aqueous medium process, where sucrose is mixed in a molten mixture with fatty acid salt using water without an organic solvent and then reacted with a higher fatty acid methyl ester in the presence of a catalyst, followed by purification, and such as by any of the methods described in International Patent Application Publication No. WO 2007/082149, whereby a sucrose molecule (which is a disaccharide containing one six-carbon aldo-sugar glucose linked to a five-carbon keto-sugar fructose, having the formula: C12H22011) is joined to one or more fatty acids.

For example, the sucrose fatty acid ester can be produced by esterification using dimethyl formamide (DMF) as a solvent, by producing a methyl ester of the fatty acid and then reacting the methyl ester with sucrose in DMF in the presence of a catalyst (e.g., potassium carbonate), for example, for 4-6 hours at 83-95° C., for example, using 30 to 127 parts sucrose to 30 parts methyl ester of the fatty acid (e.g., methyl stearate), 2 parts potassium carbonate and 300 parts solvent; by a similar method, but using dimethyl sulfoxide (DMSO) as the solvent, for example, as described in U.S. Pat. No. 3,480,616; or, as described in U.S. Pat. No. 3,644,333, by mixing sucrose with methyl fatty acid and sodium fatty acid and previously prepared sucrose ester, using potassium carbonate as a catalyst and water as a solvent; or, as described in U.S. Pat. No. 3,714,144, where sodium, potassium or lithium soap of the fatty acid is reacted in a molten sugar solution for two to twenty minutes under vacuum at 170-190° C., and purified, for example, as described in U.S. Pat. No. 4,710,567, by adding aqueous salt solution followed by three-phase separation. In one example, the sucrose fatty acid esters are prepared and purified as described in U.S. Pat. Nos. 4,898,935; 4,996,309; 4,995,911; 5,011,922 and 5,017,697, by producing the esters by chemical catalysis, such as with the solvent process, e.g., using a DMSO solvent and potassium carbonate catalyst, or aqueous solution method, followed by extraction and purification of the sucrose fatty acid esters, e.g., by adjusting pH, precipitation, separation and neutralization and filtration.

In another example, the sucrose fatty acid esters can be produced, as described in International Patent Application Publication No. WO 2007/082149, by mixing and reacting sucrose and vinyl esters of the fatty acids which can produce sucrose fatty acid ester mixtures with a monoester content of at or about 90%, and/or an acid value of less than 1. Briefly, this process can be carried out by dissolving sucrose in a solvent (e.g., DMSO), at a reaction temperature of between at or about 30° C. and at or about 60° C., such as between about 40° C. and 60° C. (e.g., at 60° C.), and a catalyst added and the mixture stirred, such as for 30 minutes, followed by removal of undissolved catalyst by decanting or filtration, followed by addition of vinyl fatty acid, and reaction, such as for at or about 15 minutes, with monitoring to measure amount of vinyl fatty acid ester, for example, until the amount of vinyl fatty acid ester reaches no more than at or about 10%, by weight (w/w), of the starting amount. The amount of sucrose and vinyl ester can vary. In one example, the ratio of sucrose to vinyl ester is between at or about 2:1 and at or about 8:1. In one example, the sucrose is added at a concentration of at or about 400 nm and the vinyl ester added at a concentration of at or about 100 nM. The catalyst can be catalyzed by a base, such as metal oxides, metal hydroxides and metal carbonates, such as potassium hydroxide, sodium hydroxide, potassium carbonate, sodium carbonate and lithium carbonate, which can be added at a concentration of between at or about 1.5 grams/L and at or about 6 g/L of reaction volume. In one example, the vinyl ester is vinyl stearate and the catalyst is potassium carbonate. The resulting mixture can then purified, such as by vacuum distillation and addition of sodium chloride to effect emulsification and purification methods described in International Patent Application Publication No. WO 2007/082149.

iv. Stabilizers

The emulsions provided herein can contain a stabilizer or a stabilizing system. Stabilizers include any compound used to stabilize the non-polar ingredients in the emulsions. The stabilizer or stabilizing system aids in retaining one or more organoleptic properties of the compositions, for example the appearance, taste or odor. The compositions provided herein, including the emulsions and spray-dried powders, containing non-polar ingredients and a stabilizer or stabilizing system can retain one or more organoleptic properties of the composition for a period of time after formulation, such as at or about 1, 2, 3, 4, 5, 6, or 7 days, at or about 1, 2, 3, 4, 5, 6, 8, 12, 18, 24, or 36 weeks, at or about 1, 2, 3, 4, 5, 6, 8, 12, 18, 24, or 36 months, or at or about 1, 2, 3, or 4 years. The stabilizers include, but are not limited to, carbonates and bicarbonates, acids, antioxidants, and any combination thereof. Typically the stabilizer or stabilizing system are food-approved, i.e., edible or ingestible, stabilizers, for example, stabilizers that are safe and/or approved for human consumption.

Typically, when present, the total amount of stabilizers included in the provided emulsions is less than 20% or about 20%, typically less than 10% or about 10%, for example, less than 20%, 15%, 10%, 5%, 4.5%, 4%, 3.5%, 3%, 2.5%, 2%, 1.5%, 1%, 0.5% or 0.1%, by weight, of the emulsion.

(a) Bicarbonates and Carbonates

Exemplary of a stabilizer used in the provided emulsions is a bicarbonate or carbonate, for example, any edible or food-approved bicarbonate or carbonate. Examples of suitable bicarbonates and carbonates include sodium bicarbonate, potassium bicarbonate, sodium carbonate, potassium carbonate, calcium carbonate, magnesium carbonate, zinc carbonate, and any combination thereof. In some examples, the carbonate or bicarbonate is a carbonated beverage, such as a soda, flavored soda, carbonated water or carbonated juice. Alternatively, the beverage can be carbonated by the addition of carbon dioxide. Selection of suitable bicarbonates and carbonates for use in the provided beverage compositions is within the skill of the skilled artisan.

(b) Edible or Ingestible Acids

In one example, the stabilizer used in the emulsions contains one or more acids, for example, any compound added to the emulsion that can lower the pH of the emulsion. The acid can be, for example, an edible, ingestible or food-approved acid. Exemplary of suitable acids for use in the provided emulsions are citric acid, phosphoric acid, adipic acid, ascorbic acid, lactic acid, malic acid, fumaric acid, gluconic acid, succinic acid, tartaric acid, maleic acid, and any combination thereof. In one example, the acid is citric acid.

(c) Antioxidants

In one example, the stabilizer used in the emulsion contains an antioxidant, for example, a molecule that is capable of inhibiting the oxidation of other molecules. Antioxidants include molecules that scavenge free radicals. Suitable antioxidants include those that are used as ingredients in dietary supplements. The antioxidant can be a natural antioxidant or a synthetic antioxidant.

Examples of antioxidants include, but are not limited to hormones, carotenoids, carotenoid terpenoids, non-carotenoid terpenoids, flavonoids, flavonoid polyphenolics (e.g., bioflavonoids), flavonols, flavones, phenols, polyphenols, esters of phenols, esters of polyphenols, nonflavanoid phenolics, isothiocyanates, vitamins and vitamin cofactors, such as vitamin A, vitamin C, vitamin E, vitamin E phosphate and ubiquinone (ubidecarenone, coenzyme Q, coenzyme Q10), ascorbic acid, citric acid, rosemary oil, minerals, such as mineral selenium and manganese, melatonin, α-carotene, β-carotene, lycopene, lutein, zeanthin, crypoxanthin, resveratrol, eugenol, quercetin, catechin, gossypol, hesperetin, curcumin, ferulic acid, thymol, hydroxytyrosol, tumeric, thyme, olive oil, lipoic acid, glutathione, gulamine, oxalic acid, tocopherol-derived compounds, di-alpha-tocopheryl phosphate, tocotrienols, butylated hydroxyanisole, butylated hydroxytoluene, ethylenediaminetetraacetic acid, tert-butylhydroquinone, acetic acid, pectin, tocotrienol, tocopherol, coenzyme Q10 (coQ10), zeaxanthin, astaxanthin, canthaxantin, saponins, limonoids, kaempfedrol, myricetin, isorhamnetin, proanthocyanidins, quercetin, rutin, luteolin, apigenin, tangeritin, hesperetin, naringenin, erodictyol, flavan-3-ols (e.g., anthocyanidins), green tea extract, gallocatechins, epicatechin and its gallate forms, epigallocatechin and its gallate forms, theaflavin and its gallate forms, thearubigins, isotlavone phytoestrogens, genistein, daidzein, glycitein, anythocyanins, cyaniding, delphinidin, malvidin, pelargonidin and peonidin. In one example, the antioxidant is vitamin C. In another example, the antioxidant is a coenzyme Q-containing compounds, such as ubiquinone (ubidecarenone, coenzyme Q coenzyme Q10).

v. Polar Solvents

The emulsions provided herein include one or more polar solvents. Polar solvents are well known in the art. The polarity of a solvent generally indicates which compounds are soluble in the solvent, and with which other solvents/liquids the solvent is miscible. Generally speaking, polar compounds are more readily solubilized in water and other polar solvents than are non-polar ingredients and ingredients. Polar solvents are more likely to be miscible with water and other polar solvents and liquids. The emulsions generally contains between about 40% and 65% by weight of one or more polar solvents, such as water.

The polarity of a solvent can be assessed by measuring a number of different parameters according to well-known methods (see, e.g., Przybitek, "High Purity Solvent Guide," Burdick and Jackson Laboratories, Inc., 1980), such as by determining a property of the solvent, such as the dielectric constant, the dipole moment or the polarity index. For example, polar solvents generally have high dielectric constants, typically dielectric constants greater than at or about 15 (see, e.g., Lowery et al., "Mechanism and Theory in Organic Chemistry," Harper Collins Publishers, 3rd ed., 1987, p. 177), such as at or about 15, 16, 17, 18, 19, 20, 21, 22, 23, 24, 25, 26, 27, 28, 29, 30, 31, 32, 33, 34, 35, 40, 45, 50, 55, 60, 65, 70, 75, 80 85, 90 or greater than 90. For example, the dielectric constant of water is at or about 80.10 at 20° C. Polar solvents generally have high polarity indices, typically greater than at or about 3 (see, e.g., Snyder, "Classification of the solvent properties of common liquids" (1974) J. Chromatog. A 92:223-230), such as at or about 3, 4, 5, 6, 7, 8 or 9 or greater than 9. Polar solvents generally have large dipole moments, typically greater than at or about 1.4 Debye, such as at or about 1.4, 1.5, 1.6, 1.7, 1.8, 1.9, 2.0, 2.1, 2.2, 2.3, 2.4, 2.5, 2.6, 3.0, 3.5, 4 or greater than 4 Debye (see, e.g., "CRC Handbook of Chemistry and Physics," Lide, ed., 82nd edition, CRC Press, 2001, p. 15(14)-15(18)). Other methods of assessing solvent polarity are known in the art, including, but not limited to, the Kosower Z scale (Kosower, "An introduction to physical organic chemistry," Wiley, 1969, p. 293), the donor number and donor acceptor scale (Gutmann, "Solvent effects on the reactivities of organometallic compounds" (1976) Coord. Chem. Rev. 18:225-255), and the Hildebrand solubility parameters (see, e.g., Giddings et al., "High pressure gas chromatography of nonvolatile species. Compressed gas is used to cause migration of intractable solutes" (1968) Science 162:67-73).

Polar solvents include polar protic solvents and polar aprotic solvents. A polar protic solvent (e.g., water, methanol, ethanol) contains a hydrogen atom attached to an electronegative atom, such that the hydrogen has a proton-like character and/or the bond between the hydrogen and electronegative atom is polarized. Polar aprotic solvents, on the other hand (e.g., acetone, acetonitrile), generally do not contain positively polarized hydrogen atoms.

The polar solvents in the provided compositions typically are polar protic solvents, including, but not limited to, water; alcohols, such as dihydric alcohols which contain two hydroxyl groups (for example, glycols, e.g., propylene glycol, ethylene glycol, tetraethylene glycol, triethylene glycol, trimethylene glycol), trihydric alcohols which contain three hydroxyl groups (e.g., glycerin, butane-1,2,3-triol, pentane-1,3,5-triol, 2-amino-2-hydroxymethyl-propane-1,3-diol), monohydric alcohols (e.g., methanol, ethanol, propanol, isopropanol, n-butanol and t-butanol) and other alcohols; and acids, such as acetic acid and formic acid. Other polar solvents include, but are not limited to, acetone, acetonitrile, butyl acetate, dimethylformamide, dimethyl sulfoxide, dioxane, ethyl acetate, tetrahydrofuran and hexamethylphosphoric triamide. Typically, the polar solvent is water, or is an alcohol that typically contains two or more hydroxyl groups, such as a trihydric or dihydric alcohol, such as, but not limited to, glycerol and propylene glycol.

The amount of the polar solvent typically is present in a high concentration, for example, the total amount of polar solvent as a percentage (%) by weight of the liquid concentrate (wt %) can be, e.g., between or between about 25% and 70%, such as between or between about 35% and 65%, such as 35% to 40%, 35% to 45%, 35% to 50%, 35% to 55%, 35% to 60%, 35% to 65%, 40% to 45%, 40% to 50%, 40% to 55%, 40% to 60%, 40% to 65%, 45% to 50%, 45% to 55%, 45% to 60%, 45% to 65%, 50% to 55%, 50% to 60%, 50% to 65%, 55% to 60%, 55% to 65%, and 60% to 65% polar solvent, by weight, of the emulsion. Exemplary concentrations of the polar solvent in the emulsions are at least or are at least about 45%, 48%, 50%, 52%, 55%, 56%, 57%, 58%, 60%, 62%, 65%, 68%, and 70% (w/w) of the emulsion.

In the provided methods for making the emulsions, the polar solvent is added to the polar phase. In one example, the polar solvent is water, e.g., purified water, such as water that is purified prior to adding it to the concentrate formula, for example, by charcoal filter, ion exchange, reverse osmosis, UV sterilization and/or filtering using a filter, for example, a 50-100 micron filter. Typically, when a filter is used, it is an end point of use filter, which filters the water before it reaches the tank in the provided process. Alternatively, previously filtered water can be added to the concentrates.

vi. Binders

The provided emulsions can further contain a binder. The binder can be any material capable of adhering other materials together, for example, during drying. Exemplary binders include, but are not limited to, polysaccharides, polyols, starches, and gums. For example, the binder can be, e.g., maltodextrin, lactose, sucrose, starch, polyethylene glycol, hypromellose, methylcellulose, macrocrystalline cellulose, polyethylene glycol, sorbitol, other sugars, and pectin. An exemplary binder is maltodextrin, a moderately sweet polysaccharide produced from starch as a creamy white hygroscopic powder. Maltodextrin is easily digestible, being absorbed as rapidly as glucose. Maltodextrin can be derived from any starch. In the U.S., this starch is usually corn or potato, whereas, elsewhere (e.g., Europe), it is commonly wheat.

When present, the amount of binder, e.g., maltodextrin, typically is present in the emulsions an amount of between or between about 5% and 20% binder, such as between or between about 5% and 7%, 5% and 10%, 5% and 12%, 5% and 15%, 5% and 17%, 5% and 20%, 7% and 10%, 7% and 12%, 7% and 15%, 7% and 17%, 7% and 20%, 10% and 12%, 10% and 15%, 10% and 17%, 10% and 20%, 15% and 17%, 15% and 20%, and 17% and 20%, by weight of the emulsion.

Typically, when a binder, e.g., maltodextrin, is present, the total amount of binder, e.g., maltodextrin, and surfactant, for example, sugar fatty acid ester, e.g., sucrose fatty acid ester, is between about 5% and 40% binder and sugar fatty acid ester, such as between or between about 5% and 10%, 5% and 15%, 5% and 20%, 5% and 25%, 5% and 30%, 5% and 35%, 5% and 40%, 10% and 15%, 10% and 20%, 10% and 25%, 10% and 30%, 10% and 35%, 10% and 40%, 15% and 20%, 15% and 25%, 15% and 30%, 15% and 35%, 15% and 40%, 20% and 25%, 20% and 30%, 20% and 35%, 20% and 40%, 25% and 30%, 25% and 35%, 25% and 40%, 30% and 35%, 30% and 40%, and 35% and 40% total binder and surfactant, e.g., sucrose fatty acid ester, by weight of the emulsion.

vii. Co-Surfactants (Emulsifiers)

The emulsions can further contain one or more co-surfactants (emulsifiers). For example, a co-surfactant can be included to improve emulsification of the non-polar compounds and/or the stability of the emulsion, for example, by preventing or slowing oxidation of the non-polar compounds and ingredients. Exemplary of a co-surfactant that can be used in the provided concentrates is a phospholipid, for example, phosphatidylcholine. Other exemplary co-surfactants include non-ionic surfactants, such as sugar-derived surfactants, including fatty acid esters of sugars and sugar derivatives, PEG derivatives of sterols, and PEG-sorbitan fatty acid esters. Other exemplary co-surfactants are fish collagen, for example, the fish collagen sold by Norland Products Inc. (Cranbury Township, N.J.) and saponin, such as saponin from quillaja bark, including the saponin from quillaja bark sold by Desert King International (San Diego, Calif.) and Sigma Aldrich (St. Louis, Mo.).

When present, the amount of the co-surfactant typically is present in a concentration less than or less than about 10%, typically less than or less than about 5%, for example, the total amount of co-surfactant as a percentage (%), by weight, of the emulsion (wt %) can be, e.g., less than or less than about 10%, such as less than or about 5%, 4.5%, 4%, 3.5%, 3.15%, 3%, 2.5%, 2%, 1.75%, 1.5%, 1.25%, 1%, 0.75%, 0.5%, 0.25%, 0.15% or less, by weight, of the emulsion.

Exemplary of the co-surfactants that can be used in the provided emulsions are phospholipids. Phospholipids are amphipathic lipid-like molecules, typically containing a hydrophobic portion at one end of the molecule and a hydrophilic portion at the other end of the molecule. A number of phospholipids can be used as co-surfactants in the provided compositions, for example, lecithin, including phosphatidylcholine (PC), phosphatidylethanolamine (PE), distearoylphosphatidylcholine (DSPC), phosphatidylserine (PS), phosphatidylglycerol (PG), phosphatidic acid (PA), phosphatidylinositol (PI), sphingomyelin (SPM) or a combination thereof. Typically, the phospholipid is phosphatidylcholine (PC), which sometimes is referred to by the general name "lecithin." Exemplary of the phospholipids that can be used as co-surfactants in the provided compositions are the phospholipids sold by Lipoid, LLC (Newark, N.J.), for example, Purified Egg Lecithins, Purified Soybean Lecithins, Hydrogenated Egg and Soybean Lecithins, Egg Phospholipids, Soybean Phospholipids, Hydrogenated Egg and Soybean Phospholipids, Synthetic Phospholipids, PEGylated Phospholipids and phospholipid blends. Exemplary of the phosphatidylcholine that can be used as a co-surfactant in the provided compositions is the phosphatidylcholine composition sold by Lipoid, LLC, under the name Lipoid S100, which is derived from soy extract and contains greater than or greater than about 95% phosphatidylcholine.

viii. Emulsion Stabilizers (Co-Emulsifiers)

The emulsions further can contain one or more emulsion stabilizers (co-emulsifiers), which can be used to stabilize the emulsions containing the pre-emulsion concentrates. For example, the emulsion stabilizer can increase the viscosity of the concentrate. One or more emulsion stabilizers can be added, for example, during formulation after evaluation of an initial emulsion, particularly if the oil and polar phases of the initial emulsion appear to be separating. Addition of the emulsion stabilizer can prevent separation of the oil and polar phases.

Exemplary of an emulsion stabilizer that can be included in the provided emulsions is a composition containing a blend of gums, for example, gums used as emulsifying agents, for example, a blend containing one or more of xanthan gum, guar gum and sodium alginate. Exemplary of such an emulsion stabilizer includes the emulsion stabilizer sold under the trademark Saladizer® emulsifier, available from TIC Gums, Inc. (Belcamp, Md.). Other gums can be included in the emulsion stabilizer, for example, gum acacia, ester gums and sugar beet pectin. Exemplary emulsion stabilizers include modified food starches. These include the modified gum acacia sold under the trademark TIC Pretested® Ticamulsion® A-2010 Powder, available from TIC Gums, Inc. (Belcamp, Md.). Other exemplary emulsion stabilizers containing an ester gum are, for example, the emulsion stabilizer sold under the trademark TIC Pretested® Ester Gum 8BG, available from TIC Gums, Inc. (Belcamp, Md.) or from Hercules/Pinova (Brunswick, Ga.). Other emulsion stabilizers sold by Ingredion™, Inc. (Westchester, Ill.) under the trademarks CAPSUL®, FIRM-TEX®, THERMFLO®, THERMTEX®, and TEXTRA® and others, can be included in the compositions provided herein. Other blends of similar gums can also be used as emulsion stabilizers.

Also exemplary of an emulsion stabilizer is whey protein. Whey protein is a protein contained in the milk serum (whey) obtained by removing casein and other components from milk, and comprises lactoalbumin, lactoglobulin, and lactoferrin as main components. Whey protein is known to have such functions as a stamina improver, a fatigue reliever, and an immunity enhancer. In addition, it is used as a protein supplement material in athletic nutrient foods and diet foods. Whey proteins are often used in food emulsion systems because of their ability to stabilize oil-in-water (O/W) emulsions. An exemplary whey protein is the whey protein isolate sold by Marquez Brothers International (Hanford, Calif.).

Another exemplary emulsion stabilizer is green tea extract, which is high in epigallocatechin gallate (EGCG) and epicatechin gallate (ECG). Green tea extract is known to have high antioxidant activity and the ability to provide stability to emulsions. An exemplary green tea extract that can be used in the emulsions provided herein is a green tea extract that contains 40% EGCG, sold by Guilin Layn Natural Ingredients, Corp. (Guilin, China).

When present, the emulsion stabilizer is typically present at a concentration of less than 10%, such as less than or less than about 10%, 9%, 8%, 7%, 6%, 5%, 4%, 3%, 2%, or 1%, by weight, of the emulsion. For example, the emulsion stabilizer can be added to the polar phase at a concentration of between 0.01% or about 0.01% and 1% or 2%, for example, more than 0.01% but less than 0.1%, 0.2%, 0.3%, 0.4%, 0.5%, 1%, or 1.5% (wt %).

ix. pH Adjusters

One or more pH adjusters can be added to the emulsions at an appropriate concentration to achieve a desired pH. One or more of a plurality of pH adjusting agents can be used. The pH adjusting agent typically is safe for human consumption, for example, GRAS certified. The pH adjuster can be citric acid. An exemplary pH adjuster includes the citric acid sold by Mitsubishi Chemical (Dublin, Ohio). Another exemplary pH adjuster is phosphoric acid, such as Food Grade 80% Phosphoric Acid, sold by Univar.

2. Powder Compositions Containing Probiotics and a Mucoadhesive Proteins

The emulsions containing the pre-emulsion concentrates provided herein are dried, such as by evaporation, spray drying, lyophilization, or other drying method, to produce the powders. The water-soluble powders are prepared by drying the emulsions provided herein, i.e., removing all of the polar solvent, e.g., water, and volatile components from the emulsions to form a powder that does not contain any, or only minimal amounts, of polar solvent, e.g., water. The resulting powders contain at least about 5% of the mucoadhesive protein, and up to about 25%-35% the mucoadhesive protein and probiotic. The mucoadhesive protein is linked to the probiotic as described, whereby the shelf life of the probiotic is more than 3 months, and is 12 months or longer, such that the concentration of probiotic is within at least about 10% of the original concentration. Removal of the volatile components, including the polar solvent, e.g., water, from the emulsion results in an increased concentration (i.e., wt %) of each ingredient in the powder compared to the corresponding emulsion. For example, the emulsions provided herein contain between or between about 10 wt % and 35 wt % mucoadhesive and probiotic.

Methods of producing powders from liquid compositions, e.g., emulsions, are well known to the skilled artisan. Exemplary processes for producing powders include, but are not limited to spray drying, freeze drying, evaporation, lyophilization, or absorption plating. The methods for forming the powders include spray drying. Spray drying processes and spray drying equipment are described generally in Perry's Chemical Engineers' Handbook, pp. 20-57 (Sixth Edition 1984). More details on spray drying processes and equipment are reviewed by Marshall (1954) "Atomization and Spray-Drying," Chem. Eng. Prog. Monogr. 50: Series 2 and Masters, "Spray Drying Handbook" (Fourth Edition 1985). Methods for spray drying are well known (see, e.g. U.S. Pat. Nos. 5,430,021 and 6,534,085 and U.S. Publication No. US 2007/0184117). In general, spray drying is used to dry a heated liquid by passing it through hot gas. One or more spray nozzles is used to atomize the liquid in a cooling tower or chamber. As the material is atomized (sprayed), the surface tension causes a uniform spherical particle to form, which is passed through the cooling chamber and hardens into a solid intact sphere. The spray dried particles can be between at or about 0.5 microns and at or about 100 microns, and typically are less than at or about 10 microns, typically less than at or about 5 microns, and typically less than at or about, or at or about, 1 micron.

The powder compositions provided herein can be made using any emulsion containing probiotics, a sugar fatty acid ester, and mucoadhesive protein, e.g., lactoferrin, such as the emulsions provided herein.

a. Formulating the Powder Compositions

The powder compositions provided herein are water-soluble and have high concentrations of the probiotic for example, at least 5%, 10%, 20%, 30%, or 40%, (generally between about 5% and 25%, inclusive), and are stable and free-flowing, i.e., not sticky. The powders also contain a surfactant, for example, a sugar fatty acid ester, e.g., a sucrose fatty acid ester, that also acts as a binder and/or in combination with a binder, that does not contribute to the oil load of the powder, thus allowing for the high concentrations of probiotic ingredients. The sugar fatty acid esters, such as sucrose fatty acid esters, are present in the water-soluble powders in place of or in combination with a binder, and result in powders that are water-soluble, free flowing, i.e., not sticky.

A number of parameters of the concentrates and emulsions, including ingredients, their relative concentrations, and methods for making the concentrates and emulsions, affect the ability of emulsion to form a free-flowing, i.e., not sticky, powder when a high concentration of non-polar ingredient is present. By extension, these parameters of the concentrates and emulsions also affect the advantageous properties of the powders, for example, the solubility of the powder, for example, in an aqueous solution.

The methods for forming the powders include spray drying. Spray drying processes and spray drying equipment are described generally in Perry's Chemical Engineers' Handbook, pages 20-54 to 20-57 (Sixth Edition 1984). More details on spray drying processes and equipment are reviewed by Marshall, "Atomization and Spray-Drying," 50 Chem. Eng. Prog. Monogr. Series 2 (1954), and Masters, Spray Drying Handbook (Fourth Edition 1985). Methods for spray drying are well known (see, e.g. U.S. Pat. Nos. 5,430,021 and 6,534,085 and U.S. Application Publication No. US 2007/0184117). In general, spray drying is used to dry a heated liquid by passing it through hot gas. One or more spray nozzles is used to atomize the liquid in a cooling tower or chamber. As the material is atomized (sprayed), the surface tension causes a uniform spherical particle to form, which is passed through the cooling chamber and hardens into a solid intact sphere. The spray dried particles can be between at or about 0.5 microns and at or about 100 microns, and typically are less than at or about 10 microns, typically less than at or about 5 microns, and typically less than at or about, or at or about, 1 micron.

Provided are methods for spray drying the liquid emulsion compositions to form powder compositions. In the spray drying methods, the liquid emulsion compositions can be heated, e.g. to a temperature between at or about 90 and at or about 140° F., typically between 100° F. and 130° F., e.g. at or about 100, 105, 110, 115, 120, 125, or 130° F. The compositions can be mixed while heating, such as with any of the mixers described herein, for example, homogenizers (e.g. reversible homogenizers and piston-driven homogenization).

For spray drying, one or more excipients are mixed with a polar solvent, typically water, and heated, e.g. to a temperature between at or about 80° F. and at or about 150° F., typically between 110° F. and 140° F., e.g. at or about 110, 115, 120, 125, 130, 135 or 140° F., depending on the dryer. In one example, the excipient is mixed with water in an amount of one part excipient (by weight) to two parts water (by weight). The excipient-solvent (e.g. water) mixture can be mixed while heating, e.g. using any of the mixers described herein, for example, homogenizers (e.g. reversible homogenizers and piston-driven homogenizers) with heating during the mixing. The heated liquid emulsion composition and the heated water-excipient mixture then are mixed together, such as by transferring one mixture to the other, e.g. by any of the transfer means provided herein. Typically, the two mixtures are homogenized, e.g. with a reversible homogenizer or piston-driven homogenizer or any other homogenizer. The homogenized mixture then is subject to spray drying using a spray dryer.

Exemplary of the spray dryers are cyclone spray dryers. During spray drying with cyclone spray dryers, the homogenized mixture is pumped into an atomizing device where it is broken into small droplets. Upon contact with a stream of hot air, the moisture is removed very rapidly from the droplets while still suspended in the drying air. The dry powder is separated from the moist air in cyclones by centrifugal action. The centrifugal action is caused by the great increase in air speed when the mixture of particles and air enters the cyclone system. The dense powder particles are forced toward the cyclone walls while the lighter, moist air is directed away through the exhaust pipes. The powder settles to the bottom of the cyclone where it is removed through a discharging device. Sometimes the air-conveying ducts for the dry powder are connected with cooling systems which admit cold air for transport of the product through conveying pipes. Cyclone dryers have been designed for large production schedules capable of drying ton-lots of powder per hour.

As will be appreciated by one of skill in the art, the inlet temperature and the outlet temperature of the spray drier are not critical but will be of such a level to provide the desired particle size, of less than at or about 1 micron, and to result in a powder that has a desired property. Typically, the ability of the free flowing powder to yield a clear (or relatively clear) liquid dilution composition upon dilution in an aqueous medium is the desired property that is evaluated. In this regard, the inlet and outlet temperatures are adjusted depending on the melting characteristics of the liquid emulsion components and the composition of the homogenized liquid emulsion concentrate/excipient mixture. The inlet temperature is between at or about 60° C. and at or about 170° C. with outlet temperatures between at or about 40° C. to at or about 120° C. Typically inlet temperatures are from at or about 90° C. to at or about 120° C. and outlet temperatures are from at or about 60° C. to at or about 90° C. In other embodiments, or with alternative dryers, the inlet temperature may be between at or about 200° C. and at or about 350° C. with outlet temperatures between at or about 200° C. to at or about 350° C. Typically inlet temperatures are from at or about 250° C. to at or about 300° C. and outlet temperatures are from at or about 250° C. to at or about 300° C. The flow rate which is used in the spray drying equipment will generally be at or about 3 mL per minute to at or about 15 mL per minute. The atomizer air flow rate will vary between values of at or about 25 L per minute to at or about 50 L per minute. Commercially available spray dryers are well known to those of skill in the art, and suitable settings for any particular dispersion can be readily determined by one of skill in the art without undue experimentation. Operating conditions such as inlet temperature and outlet temperature, feed rate, atomization pressure, flow rate of the drying air, and nozzle configuration can be adjusted in accordance with the manufacturer's guidelines.

In some examples, the dry powder is stored into a capsule form or is pressed into a tablet. For use as tablets, the compositions typically contain multiple other excipients. These excipients include tablet disintegrants, such as corn starch, glidants, such as silicon dioxide, and lubricants such as magnesium stearate. Ordinarily these compositions contain minor amounts by weight of glidants and lubricants, e.g., each two percent (2%) or less by weight. Tablet disintegrants are optionally present, and, if present, are included in sufficient amounts to assure that the tablet disintegrates upon ingestion. For example, disintegrants, such as corn starch, can be employed at concentrations of from about zero to about 30 percent by weight of the composition.

b. Ingredients and Concentration Ranges

Each of the provided powder compositions contains an emulsion that has been dried to remove all or almost all of the polar solvent, e.g., water, and other volatile components. The resulting powder contains mucoadhesive protein, such as lactoferrin, bound to the probiotic, such that the powder contains at least about 5% of each, generally up to 20% of each for a total of about 20% to 35% by weight. Other ingredients include the oil, sucrose fatty acid ester surfactant and/or other surfactant, binder, such as cluster dextrin, and stabilizer, such as $KHCO_3$. The emulsions include the polar protic solvent, and optional additional volatile components. Because of the formulation of the emulsion to contain the relatively high concentrations of mucoadhesive protein and probiotic, the shelf life (time during which at least 90% of the original amount of probiotic) retained is long, more than 3 months, as much as a year or more. This is a property of the emulsions and powders.

In some examples, the emulsion optionally contains a preservative, where the preservative does not harm the probiotic. The emulsions, and thus, the powder compositions provided herein additionally contain a surfactant, such as a sugar fatty acid ester, e.g., sucrose fatty acid ester, in place of or in combination with a binder, e.g., maltodextrin, dextrin, cluster dextrin, and additional ingredients, including, but not limited to, stabilizers, e.g., bicarbonates or carbonates, acids, and/or antioxidants, co-surfactants (emulsifiers), e.g., phospholipids and/or PEG-derived surfactants, emulsion stabilizers (co-emulsifiers), pH adjusters, e.g., citric acid, and any of the ingredients provided herein in Section 1, with the exception of volatile components, such as polar solvents, e.g., water.

The powder compositions that contain high the mucoadhesive protein and probiotic, and a sugar fatty acid ester surfactant in place of or in combination with a binder, e.g., maltodextrin, exhibit desirable properties, for example, the powder is a free-flowing, i.e., not sticky, powder that is water-soluble. The powder compositions contain a sugar fatty acid ester surfactant in place of or in combination with a binder, e.g., dextrin, cluster dextrin and/or maltodextrin. Typically, the sugar fatty acid ester is a sucrose fatty acid ester. The surfactant, e.g., sucrose fatty acid ester, does not contribute to the oil load of the composition, thus allowing the addition of high concentrations of non-polar ingredients and formation of a free-flowing, i.e., not sticky, powder. In one example, the powder contains a sugar fatty acid ester, e.g., sucrose fatty acid ester, in place of a binder, e.g., maltodextrin. In another example, the powder contains a sugar fatty acid ester, e.g., sucrose fatty acid ester, in combination with a binder, e.g., maltodextrin.

The powder compositions provided herein contain a surfactant, such as a sugar fatty acid ester, e.g., sucrose fatty acid ester, where the total amount of surfactant, e.g., sucrose fatty acid ester, is typically present in an amount as a percentage (%) by weight of the powder compositions (wt %), e.g., from at or about 5 wt % to at or about 30 wt %, such as between or between about 5% and 7%, 5% and 10%, 5% and 12%, 5% and 15%, 5% and 17%, 5% and 20%, 5% and 25%, 5% and 30%, 7% and 10%, 7% and 12%, 7% and 15%, 7% and 17%, 7% and 20%, 7% and 25%, 7% and 30%, 10% and 12%, 10% and 15%, 10% and 17%, 10% and 20%, 10% and 25%, 10% and 30%, 12% and 15%, 12% and 17%, 12% and 20%, 12% and 25%, 12% and 30%, 15% and 17%, 15% and 20%, 15% and 25%, 15% and 30%, 17% and 20%, 17% and 25%, 17% and 30%, 20% and 25%, 20% and 30%, and 25% and 30% sugar fatty acid ester, e.g., sucrose fatty acid ester, by weight of the powder compositions. Exemplary concentrations of the total amount of sugar fatty acid ester, e.g., sucrose fatty acid ester in the powder compositions are at least or at or about 5%, 7%, 10%, 12%, or 15% up to about 20% (wt %) of the powder compositions.

The powder compositions provided herein can contain a binder. Exemplary binders include, e.g., dextrin, cluster dextrin, maltodextrin. Typically, when a binder, is present in the powder composition, the total amount of binder, e.g., maltodextrin, and surfactant, such as a sugar fatty acid ester, e.g., sucrose fatty acid ester, is typically present in a total amount as a percentage (%) by weight of the powder compositions (wt %), e.g., from at or about 5 wt % to at or about 60 wt %, such as between or between about 4 wt % and 10 wt %, 5 wt % and 15 wt %, 5 wt % and 20 wt %, 5 wt % and 25 wt %; or 15 wt % and 30 wt %, all inclusive.

D. EXEMPLARY METHODS FOR PREPARING THE EMULSIONS

Methods for preparing compositions and powders containing high amounts of non-polar ingredients and a sugar fatty acid ester-binder mixture are provided herein. Equipment for use in the methods and general steps of the methods are described below. The methods include bench-top manufacturing processes, which are used to make small quantities of the concentrates. The methods also include scaled-up manufacturing processes, which are used to make larger batches of the compositions and powders. Any of the bench-top processes can be scaled up to perform the methods using the scaled-up processes. Any of the provided compositions and powders can be made using either scaled-up or bench-top processes. The compositions provided herein can be made following the methods provided in U.S. Pat. No. 8,282,977 and U.S. Patent Publication Nos. 2009-0297491 and 2012-0016026.

1. Equipment Employed in the Methods

Equipment used in various steps of the provided methods for making the compositions and powders can include, for example, vessels, such as tanks, for mixing the water and oil phases and the product; scales; mixers, for example standard mixers and homogenizers; heating and cooling apparatuses, such as water-jacketed tanks, hot plates, water baths and chillers (coolers), including recirculating coolers; transfer apparatuses, for example, transfer devices, such as, pumps, hoses and sanitary fittings; ball valves; purifiers, for example, filters, such as carbon filters, ion exchange equipment, reverse osmosis equipment, end-point filters and end product filters; evaluation devices, for example, pH and temperature meters; and other equipment. The choice of equipment depends on a plurality of factors, including batch size and the manufacturing process.

a. Scales

One or more scales can be used to measure the amount of the ingredients before adding them to the appropriate vessel. Alternatively, the ingredients can be weighed in the vessel, for example, in a tank on top of a scale.

Any of a plurality of well-known, commercially-sold scales can be used to weigh the ingredients. The choice of scale(s) can depend on a number of factors, including the mass of the product being made (e.g., the batch size) and the ingredient being weighed. In one example, multiple scales are used to weigh the various ingredients of the compositions and products. In general, relatively larger capacity (i.e., weight) scale(s) are used in making larger batches of the products while relatively smaller capacity scale(s) are used in making smaller batches.

Exemplary of the scales used to weigh the ingredients using the provided methods are a Toledo Scale (Model GD13x/USA); a Sartorius Basic Analytical Scale (Model BA110S), which is a basic series analytical scale with a 110 g capacity and a resolution of 0.1 mg; and an OHAUS Scale (Model CS2000), which is a compact portable digital scale having a 2000 g capacity and a resolution of 1 g.

b. Purifiers

Purifiers, such as filters, are used in the provided methods to remove impurities from the ingredients prior to their addition to and/or from the composition or product or to and/or from a phase of the composition or product. For example, the water added to the polar phase typically is purified water. In one example, one or more purifiers, for example, carbon filters, ion exchange purifiers, reverse osmosis purifiers, and/or end-point filters can be used to filter water, for example, city water, prior to its addition to the polar phase. For example, the water can be filtered to remove impurities, such as sediment, from the water.

Purifiers that can be used with the provided methods include filters, for example, 100 micron filters and carbon filters, which are filters that use activated carbon to remove impurities by chemical adsorption. Carbon filtering typically is used for water purification and is particularly effective at filtering out chlorine, sediment, volatile organic compounds and other impurities. Typically, the particles removed by carbon filters are between about 0.5 microns and about 50 microns. Other filters are well known and can be used with the provided methods.

The purifiers also include reverse osmosis purifiers, which use mechanical pressure to purify liquids, for example, water. In one example, the pressure forces the water through a semi-permeable membrane to remove impurities.

The purifiers also include exchange purifiers, for example, an ion exchange purifier. The ion exchange purifier can use a resin bed, such as a zeolite resin bed, to replace salts, such as cations, e.g., magnesium and calcium, with other cations, such as sodium and potassium cations. Such purifiers can be purchased, for example, from Aqua-Pure Filters (Clarkston, Mich.).

In one example, the purifier is an end-product filter (e.g., a 100 micron filter; Product No. BPEM 100-5GP; FSI, Michigan City, Ind.). This filter is used to filter any impurities out of the final product (e.g., the final pre-emulsion composition). Other filters also are known and can be used with the provided methods.

c. Vessels

One or more, typically two or more, vessels can be used in the methods to contain the ingredients of the provided compositions and powders, for example, during mixing and/or heating or cooling. The vessels can be tanks, for example, water-jacketed tanks; pots; and/or beakers, for example, Pyrex® beakers. Separate vessels (e.g., an oil phase tank and a polar phase tank) can be used for mixing and heating the ingredients of the oil phase and the polar phase prior to combining the two phases. In some examples, an additional vessel, for example, a holding and/or packaging tank, can be used for holding and/or packaging the compositions and powders and/or for addition/mixing of additional ingredients to the compositions and powders.

A number of vessels are available for mixing ingredients. Typically, the vessels are cleaned, for example, rinsed, soaped and/or sanitized, according to known procedures prior to use and between uses, such as with the cleaning procedures described below.

In the bench-top process, the vessel can be a container, for example, a bench-top container, such as a flask, beaker (e.g., a Pyrex® beaker), vial, measuring container, bottle and/or other bench-top container.

In the scaled-up manufacturing process, the vessels can be tanks, for example, polar phase tanks, oil phase tanks and holding/packaging tanks. Typically, the tanks are equipped with one or more mixers, for example, a standard mixer and/or homogenizer, which are used to mix the ingredients that are added to the tank. In one example, the tank is further equipped with a heating and/or cooling device. For example, the tank can be a water-jacketed tank. The temperature of the water-jacketed tank is controlled through the water jacket, for example, to heat the contents, such as during mixing.

Exemplary of the tanks that can be used with the provided methods are water-jacketed tanks, for example, the Overly 550 gallon water-jacketed tank (Model 10576501G), which has a 550 gallon capacity and typically is used as a polar phase tank, the Schweitzer's 450 gallon tank (Model #5214-C), which has a 450 gallon capacity and typically is used as an oil phase tank and the Royal 190 gallon water-jacketed tank (Model 9977-5), which has a 190 gallon capacity and can be used as a water or oil phase tank when mixing smaller volumes. Other tanks are well known and can be used with the provided methods for mixing the compositions and powders, for example, the phases of the composition.

d. Mixers

Mixers are used in the methods to blend, mix and/or emulsify the compositions and ingredients, mixtures and phases of the compositions. In some examples, the mixers can be used to keep the ingredients and/or mixture circulating to maintain temperature, viscosity and/or other parameters of the mixture. Suitable mixers include, but are not limited to, standard mixers, for example, those that can be used to mix ingredients and maintain a homogeneous mixture, such as while heating a mixture of ingredients. Exemplary of the standard mixers are LIGHTNIN® mixers (LIGHTNIN®, Rochester, N.Y.), for example, Model Numbers XJC117 and ND-2. In one example, the LIGHTNIN® mixers are fixed-mount, gear drive high-flow mixers, for use with closed tanks. Another example of a standard mixer is a mixer sold by the IKA® corporation, for example, overhead IKA® mixers. Exemplary IKA® mixers Model Nos. RW-14 Basic and RE-16S, which are laboratory stirrers that can be used to mix ingredients. In some examples, the mixer can be attached to the vessel, e.g., the tank, such as by mounting or clamping onto the tank, such as at the top of the tank. In other examples, the mixer can be placed in the vessel for mixing.

The mixer can be a homogenizer which can be used, for example, to emulsify mixtures, i.e., form an emulsion. The homogenizer can be used to mix phases of the compositions, e.g., oil and polar phases, after combining the phases, in order to form an emulsion. The homogenizer provides high-shear dispersion of solids and emulsification of immiscible liquids at high shear rates. Suitable homogenizers include, but are not limited to, high-shear homogenizers, for example, reversible homogenizers sold by Arde Barinco, Inc. (Norwood, N.J.). Exemplary Arde Barinco, Inc. reversible homogenizers are Model CJ-50 (a 3600 rpm mixer having a 6-inch rotor diameter, tip speed of 5575 ft/minute, emersion depth of 33 inches, and six separate openings at the bottom and top, which concentrate the liquid into six chambers, reducing the surface volume and creating a shear effect); and Model CJ-4E (a 10,000 rpm mixer with fan-cooled motor, optimized for 1 to 5 gallon batch sizes, having a 1.875 inch rotor diameter, tip speed of 4920 rpm, and immersion depth of 16 inches). The homogenizers further include other homogenizers, for example, other reversible homogenizers sold by Arde Barinco, Inc.

In one example, the homogenizer is attached to the top of the vessel, for example, the tank, for example, by clamps or by channel locks and an electrical hoist. In another example, the homogenizer is placed in the vessel. The Arde Barinco reversible homogenizers contain axial flow impellers, which create two distinct mixing actions, depending on direction. Downward "vortex flow" pulls solids from the top and bottom of the mixture, while upward "umbrella flow" controls mixing at the highest shear and recirculation rates without splashing or incorporating air. The reversible homogenizers typically are equipped with an adjustable baffle plate, which can be adjusted to control the type of mixing, for example at different times during mixing, e.g., during emulsification.

A number of other mixers are well known and can be used with the provided methods. Exemplary of suitable mixers that can be used with the provided methods are homogenizers, inline mixers, ribbon mixers, plow mixers, paddle mixers, Forberg® mixers, conveyors, bag dumps and compactors, V-blenders, blade mixers, double cone mixers, continuous mixers, speedflow mixers, batch mixers, double ribbon blenders, paddle and ribbon mixers with choppers, plow blenders, turbulent mixers, fluidizing mixers sold under the trademark Forberg®, air mixers, active mixers, passive mixers, top-entry mixers, side-entry mixers, static mixers, fixed-entry mixers, portable mixers (e.g., direct and gear drive), sanitary mixers, drum mixers, bulk container (IBC) mixers, lab stirrers, variable speed mixers, dough mixer, vertical mixer, spiral mixer, twin arm mixer, fork mixer, double spiral mixer, all agitators, agitator mixers, Banbury® mixers, rubber mixers, Blondheim® mixers, churn mixers, conical mixers, continuous mixers, disperser mixers, pan mixers, emulsifier mixers, Hobart® mixers, liquefier mixers, Littleford® mixers, meat mixers, plow mixers, Mix-Muller® mixers, vertical screw mixers (e.g., Nauta® mixers), Oakes® mixers, planetary mixers, pony mixers, pug mixers, Ross™ mixers, rotary mixers, Sigma® mixers, single arm mixers, tote bin mixers, tumble mixers, vacuum mixers, Turbolizer® mixers, twin shell mixers, V-type mixers, zigzag mixers, side-arm mixers, hand-held mixers, stir rods, stir bars, magnetic mixers, overhead mixers (e.g., mechanical and/or electric overhead mixers), and any mixer known to those of skill in the art.

e. Heating/Cooling Apparatuses

Equipment that can be used in the methods includes heating and cooling apparatuses. The heating and cooling apparatuses can be used to control the temperature of the ingredients and combinations thereof, such as while generating the compositions and products.

Heating apparatuses that can be used in the provided methods are those that are capable of heating the mixture to between at or about 45° C. and at or about 85° C., for example, to at or about 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C., 81° C., 82° C., 83° C., 84° C. or 85° C. Typically, the heating apparatus is used to heat the mixtures to a temperature of between at or about 40° C. to at or about 70° C.

The heating apparatus can be a water jacket, for example, a water jacket on a water-jacketed tank, which can be controlled, for example, by a control panel, such as to adjust the temperature of the contents of the tank. Other suitable heating apparatuses are immersible and/or submersible heaters, for example, 12 KW or 13 KW sanitary heaters, including food-grade heaters, that can be immersed into the tanks, typically while mixing and typically when higher temperatures are required, such as when temperatures greater than 60° C. or about 60° C., or greater than 80° C. or about 80° C. are required. The heating apparatuses also include stoves, for example, propane stoves, and hot plates, for example, Thermolyne® hot plates (e.g., Model Nos. 846925 and SP46615).

The cooling apparatus can be any apparatus that can cool the ingredients and combinations thereof, such as rapidly cooling and/or cooling while mixing the ingredients. Typically, the cooling apparatus is capable of cooling the mixtures to a temperature between at or about 25° C. and at or about 45° C., for example, to at or about 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C. or 45° C. In some examples, the cooling apparatus can cool the mixture to a temperature between at or about 30° C. and at or about 35° C. Typically, the cooling is rapid cooling. For example, the compositions can be cooled to a temperature between at or about 30° C. and at or about 35° C. in at or about 15 minutes to at or about 2 hours, for example, in at or about 30 minutes to at or about 60 minutes, such as in at or about 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60 minutes. In an exemplary method, the compositions can be cooled to a temperature between at or about 30° C. to at or about 35° C. in at or about 30 minutes to at or about 60 minutes.

Suitable cooling apparatuses for use in the methods include chillers, for example, recirculating coolers. The cooling apparatuses can be attached to the vessel, such as remotely or by a tank mounted in the cooler, to repeatedly circulate fluid from the tank, through the chiller and back to the vessel, to rapidly cool and maintain the temperature of the mixture during mixing. Exemplary of cooling apparatuses that can be attached to the tank and used with the provided methods are open-loop chillers and closed-loop chillers, for example, those sold by Turmoil (West Swanzey, N.H.), such as Model No. OC-1000 RO. Suitable cooling apparatuses also include water baths and ice baths, for example, water baths and/or ice baths in which the vessel is placed, for example, during homogenizing. Other cooling apparatuses are well known by those of skill in the art and can be used with the provided methods.

f. Transfer Devices

Transfer devices can be used with the provided methods to transfer liquid from one vessel to another vessel. Transfer devices can be used in the methods to combine the phases and form the emulsion. For example, transfer device can be used to transfer the polar phase from the polar phase vessel to the oil phase vessel or to transfer the oil phase from the oil phase vessel to the polar phase vessel. Transfer devices include, for example, transfer pumps and associated accessories (e.g., fittings), including ball valves, sanitary fittings (for example, sanitary fittings sold by Grainger®, Inc. (Lake Forrest, Ill.)) and transfer hoses (for example, hoses sold by Sani-Tech® West (Oxnard, Calif.)), such as food grade hoses attached to a transfer pump, for example, the food grade Sani-Tech® STHT®-R-HD braid-reinforced heavy duty silicone hose. Suitable transfer pumps include the Teel™ Pump (Model 2P377B; Grainger®, Inc., Lake Forrest Ill.), a self-priming pump having a power rating of 2 HP, 60 Hz voltage, 208-230/460 AC, speed of 3450 rpm; and other pumps, such as self-priming pumps from Grainger®, Inc. The transfer device can also include equipment for manually transferring the liquid to another vessel, for example, by pouring, pipetting and/or other well-known methods of manually transferring liquids.

g. Evaluation Equipment

Evaluation equipment includes equipment that can be used to evaluate properties of the products and/or phases of the products, such as the temperature, pH, clarity, color, activity, smell and/or taste of the products. Suitable evaluation equipment includes pH and temperature meters, such as the pH and temperature meter sold by Hanna Instruments (Model No. HI 8314; Ann Arbor, Mich.), which can be used to measure the temperature and the pH of the product. Temperature meters can also include temperature probes, for example, digital and/or water-proof temperature probes, such as temperature probes sold by Cooper-Atkins (Middlefield, Conn.), for example, the Cooper-Atkins digital waterproof temperature probe (Model #DPP400W). The products can be evaluated and analyzed to verify the amounts of the non-polar ingredients and to verify that the products meet industry standards, such as to verify that the products do not contain levels of microbials and heavy metals that are above acceptable levels. Typically, these tests are performed by sending a sample of the product to a commercial testing facility, as described in section D.2.h., below.

2. General Methods for Producing the Compositions

In general, the methods useful for making the emulsions provided herein are performed by generating an oil phase (e.g., a pre-emulsion concentrate) and generating a polar phase and combining (e.g., using a transfer device) and mixing the phases to form emulsions. The powders are generated from the emulsions, for example, by drying the emulsions. For example, the powders can be prepared by evaporation, spray drying, lyophilization, or any other drying method. The oil and polar phases typically are generated in separate vessels. The vessels can be, for example, tanks. Generation of the polar phase and generation of the oil phase can be performed simultaneously or sequentially, in any order. Typically, both phases are heated to a desired temperature prior to combining the phases. For example, the phases can be heated to between 60° C. and 70° C. prior to combining the phases. The provided methods can include additional steps. In some examples, the additional steps include evaluating properties of the products, adding additional ingredients (e.g., taste-modifying agents), packaging and/or filtering.

The provided methods can be performed using a bench-top manufacturing process (for small batch sizes) or performed using a scaled-up manufacturing process (for larger batch sizes). Each of the provided products can be made with either the bench-top or scaled-up process. In one example, the product is first made with the bench-top process and then the method is scaled-up to make larger quantities of the product.

The bench-top process can be performed on a bench, counter, table or any other suitable surface. Typically, the bench-top process is used to make emulsions having relatively smaller volumes than those made with the scaled-up process. For example, volumes less than 1 L or about 1 L, or less than 1 gallon or about 1 gallon, for example, less than or about 500 mL, for example, less than or about 1000 mL, 900 mL, 800 mL, 700 mL, 600 mL, 500 mL, 450 mL, 400 mL, 350 mL, 300 mL, 250 mL, 200 mL, 150 mL, 100 mL, or 50 mL or less, can be made using the bench-top process.

For the bench-top process, the equipment can be sufficiently compact to be used on a bench-top or other similar surface, and can be sufficiently compact to be moved, for example, lifted, by the artisan using the methods. For example, the vessels, such as polar phase vessels, oil phase vessels, holding vessels, and packaging vessels, can be bench-top vessels. Exemplary bench-top vessels include, for example, flasks, beakers, vials, measuring containers, bottles and/or other bench-top containers. In some examples, the vessel in the bench-top process is a Pyrex® beaker.

Typically, the mixers for use in the bench-top processes of the provided methods are mixers that can be used in the bench-top vessels. Mixers that can be used in the bench-top vessels include, for example, standard mixers, such as hand-held mixers, stir rods, stir bars, magnetic mixers and overhead mixers, including, for example, mechanical and/or electric overhead mixers, and any other mixer that is suitable for use in the bench-top vessel. Exemplary standard mixers include those sold by IKA®, for example, overhead IKA® mixers, such as Model Nos. RW-14 Basic and RE-16S, which are laboratory stirrers and can be used to mix ingredients, such as to generate the oil and polar phases. Suitable bench-top mixers also include homogenizers, for example, reversible homogenizers. An exemplary reversible homogenizer is the Arde Barinco reversible homogenizer, Model no. CJ-4E, which can be used to emulsify the phases.

Typically, the heating and cooling apparatuses are those that can be used with the bench-top vessels, such as hot plates, ice baths and/or water baths, into (or onto) which the vessels can be placed, for example, for rapid cooling. The evaluation device used in the bench-top process, for example, the temperature and/or pH meters, typically are capable of being placed in the bench-top vessels.

For the bench-top process, combining the oil and polar phases typically is carried out manually, e.g., by pouring, pipetting and/or another manual transfer device.

The scaled-up manufacturing process of the methods typically is used to make products of relatively larger volumes, such as volumes greater than 1 L or about 1 L, or greater than 1 gallon (gal) or about 1 gallon. For example, volumes greater than or about 0.5 L, for example, greater than or about 0.5 L, 1 L, or 2 L, or greater than or about 1 gal, 2 gal, 3 gal, 4 gal, 5 gal, 6 gal, 7 gal, 8 gal, 9 gal, 10 gal, 11 gal, 12 gal, 13 gal, 14 gal, 15 gal, 16 gal, 17 gal, 18 gal, 19 gal, 20 gal, 21 gal, 22 gal, 23 gal, 24 gal, 25 gal, 26 gal, 27 gal, 28 gal, 29 gal, 30 gal, 40 gal, 50 gal, 60 gal, 70 gal, 80 gal, 90 gal, 100 gal, 150 gal, 200 gal, 250 gal, 300 gal, 350 gal, 400 gal, 450 gal, 500 gal, 550 gal, 600 gal, 650 gal, 700 gal, 800 gal, 900 gal, or 1000 gal or more, can be made using the scaled-up manufacturing process.

In general, equipment used for the scaled-up process is compatible with larger volume batches (batch sizes). For example, the vessels for use in the scaled-up processes can be tanks, for example, water-jacketed tanks, which are equipped with water jackets that can be used as heating apparatuses to heat the oil and polar phase ingredients during generation of the oil and polar phases. The water jackets typically are controlled via control panels. The transfer device can include devices attached to and connecting the tanks, such as transfer pumps and associated fittings, for example, ball valves and hoses that are attached to the tanks. Mixers for use in the scaled-up process can be standard mixers, for example, mounted mixers, such as LIGHTNIN® mixers, e.g., Model Nos. XJC117 (a fixed-mount, gear drive high-flow mixer) and ND2.

Prior to beginning the methods, the water jacket lines on any water-jacketed oil phase and polar phase tank can be bled. The water jacket switches can then be turned on to maintain a pressure in the water jackets of between at or about 20 psi and at or about 40 psi (pounds per square inch). If the pressure in the water jacket falls below 20 psi during the method, the line can be bled and checked for bubbles while purging the line.

a. Oil Phase Ingredients

Typically, oil phase ingredients include one or more lipophilic and/or amphipathic ingredients including the mucoadhesive protein, such as lactoferrin and probiotic. Oil phase ingredients typically do not include aqueous ingredients or hydrophilic ingredients. Certain ingredients, for example, ingredients having hydrophobic and hydrophilic moieties, for example, surfactants and co-surfactants, can be added to either the oil or the polar phase, or to the oil and the polar phase. Exemplary of ingredients used in the oil phase of the provided concentrates are non-polar ingredients, for example, non-polar compounds, including any of the non-polar compounds provided herein; pH adjusters, for example, citric acid; surfactants; co-surfactants, for example, sucrose fatty acid esters; preservatives, such as benzyl alcohol; and oils, for example, non-polar solvents and other oil phase ingredients.

Oil phase ingredients can be added to the oil phase simultaneously and/or sequentially, for example, in any order or in a specific order. In one example, one or more oil phase ingredients is added first, prior to addition of further ingredient(s). In one example, when the oil phase ingredients include a surfactant, a preservative, and a non-polar ingredient, these ingredients are added sequentially, in the following order: 1) surfactant; 2) preservative; and 3) non-polar ingredient. In another example, when the oil phase ingredients include a surfactant and a non-polar ingredient, the ingredients are added sequentially, in the following order: 1) surfactant and 2) non-polar compound. In another example, when the oil phase ingredients include a preservative and a non-polar compound, the ingredients are added sequentially, in the following order: 1) surfactant and 2) non-polar ingredient. Alternatively, the oil phase ingredients can be added in a different order, for example, any order. Two or more oil phase ingredients can be added simultaneously.

Typically, when the oil phase includes a surfactant, particularly when the surfactant is a surfactant that is solid at room temperature, for example, tocopherol polyethylene glycol succinate surfactant, the surfactant is the first oil phase ingredient added to the oil phase vessel. Typically, the non-polar ingredient is the last ingredient added to the oil phase vessel.

b. Oil Phase Production

To produce the oil phase, appropriate amounts of the oil phase ingredients are added to the oil phase vessel. Oil phase vessels can include tanks, for example, water-jacketed tanks, such as, but not limited to, the Royal 190 Gallon water-jacketed tank, or any other tank described herein. The amounts of the oil phase ingredients are measured, e.g., weighed, either prior to adding to the oil phase vessel or are weighed/measured in the oil phase vessel. In one example, the oil phase ingredients are measured by weighing the ingredients on a scale (e.g., one or more of the scales described herein; the choice of scale depends on the desired amount of the ingredient), before addition to the oil phase vessel. Typically, the appropriate amount of the oil phase ingredient is calculated based on the desired concentration (e.g., weight by weight (w/w), molarity (M), volume by weight (v/w) or volume by volume (v/v)), of the ingredient in the final product.

In general, the oil phase ingredients are added, mixed and/or heated in the oil phase vessel. Mixing the oil phase ingredients can be carried out with a standard mixer or other mixer, such as, but not limited to, the mixers described herein, for example, a Lightning mixer (e.g., Model No. XJC117, a fixed-mount gear drive high-flow mixer). Heating the oil phase ingredients is carried out using a heating apparatus, such as those described herein, typically a water jacket on a water-jacketed tank. In one example, the ingredients are heated to temperatures between at or about 30° C. and at or about 85° C., for example, to at or about 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C., 81° C., 82° C., 83° C., 84° C. or 85° C. In one example, the oil phase ingredients are heated to a temperature of between at or about 35° C. and 45° C., for example, by adjusting the temperature on a water-jacketed tank.

The oil phase ingredients can be added to the oil phase vessel simultaneously or sequentially in any order. In one example, one or more of the ingredients are added, mixed and/or heated, prior to the addition of the other ingredients to the vessel.

In an exemplary method provided herein, the oil phase is generated by heating a surfactant, such as a sucrose fatty acid ester surfactant, e.g., SFAE, in the oil phase vessel. The oil phase is then heated to the desired temperature, for example, to a temperature of between at or about 35° C. and 45° C., by adjusting the temperature on a water-jacketed tank, until dissolved. After the oil phase reaches the desired temperature, e.g., at or about 35° C. to 45° C., a non-polar ingredient, such as the non-polar ingredients described herein, is added to the oil phase. In some examples, the oil phase ingredients are mixed (e.g., using a mixer as provided herein) during generation of the oil phase. Typically, the oil phase ingredients are mixed until combined and maintained at the desired temperature, e.g., between at or about 35° C. and 45° C., prior to combining with the polar phase.

c. Polar Phase Ingredients

The polar phase includes one or more polar solvents, such as water, and other polar phase ingredients. Typically, polar phase ingredients are hydrophilic and/or amphipathic ingredients of the emulsion. For example, oils and other lipophilic ingredients typically are not added to the polar phase. Certain ingredients, for example, ingredients having hydrophobic and hydrophilic moieties, for example, surfactants and co-surfactants, can be added to either the oil or the polar phase, or to the oil and the polar phase. Exemplary polar phase ingredients include, but are not limited to, polar solvents, e.g., water, typically filtered water; stabilizers, for example, bicarbonates, such as potassium bicarbonate, vitamins, such as vitamin C, green tea extract, such as a green tea extract that contains epigallocatechin gallate (EGCG), and fish collagen; binders, such as maltodextrin and fish collagen; emulsion stabilizers; pH adjusters, for example, citric acid; flavors; surfactants; co-surfactants, for example, sucrose fatty acid esters; co-emulsifiers; and preservatives.

Polar phase ingredients can be added to the polar phase simultaneously and/or sequentially, in a specific order. In one example, one or more polar phase ingredients are added first and heated, prior to addition of further ingredient(s). In one example, when the polar phase ingredients include a polar solvent and an emulsion stabilizer, these ingredients are added sequentially, in the following order: 1) polar solvent, and 2) emulsion stabilizer. In one example, when the polar phase ingredients include water and an emulsion stabilizer, these ingredients are added sequentially, in the following order: 1) water, and 2) emulsion stabilizer. In another example, when the polar phase ingredients include a surfactant, a polar solvent (e.g., water) and an emulsion stabilizer, these ingredients are added to the polar phase vessel sequentially, in the following order: 1) surfactant; 2) polar solvent (e.g., water); 3) emulsion stabilizer. Alternatively, the polar phase ingredients can be added in any other order. Typically, when the polar phase includes a surfactant, particularly when the surfactant is a surfactant that is solid at room temperature, for example, tocopherol polyethylene glycol succinate surfactant, the surfactant is the first polar phase ingredient added to the polar phase vessel. Typically, when the polar phase ingredients include an emulsion stabilizer, the emulsion stabilizer is the last ingredient added to the polar phase vessel.

d. Polar Phase Production

To produce the polar phase, appropriate amounts of the polar phase ingredients are added to the polar phase vessel. Polar phase vessels can include tanks, for example, water-jacketed tanks such as, but not limited to, the Overly 550 gallon water-jacketed tank, or any other tank described herein. The amounts of the polar phase ingredients are measured, e.g., weighed, either prior to adding to the polar phase vessel or are measured in the polar phase vessel. In one example, the polar phase ingredients are measured by weighing the ingredients on a scale (e.g., one or more of the scales described herein; the choice of scale depends on the desired amount of the ingredient), before addition to the polar phase vessel. Typically, the appropriate amount of the polar phase ingredient is calculated based on the desired concentration (e.g., weight by weight (w/w), molarity (M), volume by weight (v/w) or volume by volume (v/v)), of the ingredient in the final product.

Polar phase ingredients can include water, typically purified water. In one example, unpurified water, for example, city water, is purified to remove impurities using one or more purifiers (e.g., purifiers described herein) prior to adding it to the polar phase vessel. In another example, unpurified water, for example, city water, is purified by passing the water through the following purifiers, typically sequentially, in the following order: a carbon filter, an ion exchange purifier, a reverse osmosis purifier and an end-point filter, for example, a 100 micron end-point filter.

In general, the polar phase ingredients are added, mixed and/or heated in the polar phase vessel. The polar phase vessel can be a polar phase tank, for example, a water-jacketed tank, such as one of the tanks described herein (e.g., an Overly 550 gallon water-jacketed tank). In one example, ingredients are heated to temperatures between at or about 45° C. and at or about 65° C., for example, to at or about 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., or 65° C. In one example, the polar phase ingredients are heated to a temperature of between at or about 45° C. and 55° C., for example, by adjusting the temperature on a water-jacketed tank or using another heating apparatus.

The mixing can be carried out with a standard mixer, a homogenizer, or any other suitable mixer, such as, but not limited to, the mixers described herein. Exemplary mixers include standard mixers, such as Lightnin® mixers (e.g., Model No. XJC117, a fixed-mount gear drive high-flow mixer) and homogenizers, such as Arde Barinco reversible homogenizers (e.g., Model No. CJ-4E). The mixer can be attached to the top of the polar phase vessel, for example, attached to the tank, such as mounted on the top of the tank.

The polar phase ingredients can be added to the polar phase simultaneously or sequentially in any order. Typically, the water, e.g., purified water, is added before adding the other polar phase ingredients. In one example, one or more of the ingredients are mixed and/or heated in the polar phase tank before adding the other polar phase ingredients.

In an exemplary method provided herein, the polar phase is generated by heating water, e.g., purified water, in the polar phase vessel to the desired temperature, for example, to a temperature of between at or about 45° C. and 55° C. After the polar phase reaches the desired temperature, e.g., between at or about 45° C. and 55° C., an emulsion stabilizer, such as the SALADIZER® brand emulsion stabilizer (blend of xanthan gum, guar gum and sodium alginate) is added to the polar phase. The polar phase is then mixed using a mixer such as a homogenizer, for example an Arde Barinco® reversible homogenizer (e.g., Model No. CJ-4E), typically using the "reverse" setting. The homogenizer can be attached to the top of the polar phase vessel. Additional polar phase ingredients are then added to the polar phase tank at a temperature of between at or about 45° C. and 55° C. The mixture is then mixed until the ingredients are dispersed, using a mixer, such as a standard polar phase mixer, for example, a Lightn® mixer (e.g., Model No. XJC117). Typically the heat is maintained at a temperature of between at or about 45° C. and 55° C. Typically, the ingredients are mixed until combined and maintained at the desired temperature e.g., between at or about 45° C. and 55° C., until combining with the oil phase.

e. Combining Phases

After the oil phase and the polar phase are generated, the phases can be combined, for example, by using a transfer device, and mixed, e.g., homogenized, to form an emulsion. In one example, the oil phase is transferred from the oil phase vessel to the polar phase vessel. In another example, the polar phase is transferred from the polar phase vessel to the oil phase vessel. In another example, the oil and polar phases are transferred to another vessel, such as an emulsifying vessel.

Transfer devices can include any device for transferring the contents of one vessel to another vessel, as described above. For example, suitable transfer devices include transfer pumps and associated equipment, such as, but not limited to, combinations of sanitary fittings, hoses and/or ball valves; manual transfer devices, for example, pouring and/or pipetting device; and any other suitable transfer device known to those of skill in the art. Typically, the phases are kept clean, e.g., sterile, during transfer. Sterility of the phases can be maintained, for example, by transfer devices having sanitary fittings and/or by combining the phases in a sterile environment. In one example, the transfer device includes a transfer pump, for example, a Teel™ pump (Model No. 2P377B; Grainger®, Inc.), sanitary fittings, transfer hoses, for example, food grade hoses, such as those sold under the trademark Sani-Tech® West, and ball valves, which are attached to the tanks and connect the tanks.

Simultaneous with and/or subsequent to the combination of the phases, a mixer, for example, a homogenizer (e.g., a reversible homogenizer), can be used to emulsify the water and oil phases. In one example, a homogenizer, e.g., a homogenizer mounted on one of the tanks, is turned on, the ball valves are opened, and the transfer pump is turned on to effect transfer of the contents of one tank to another, for example, to transfer the contents of the oil phase tank to the polar phase tank. As the phases are combined, they can be mixed by the homogenizer to form an emulsion. The position of the homogenizer in the tank can be adjusted, for example, by adjusting a baffle plate, e.g., moving the baffle plate further into/out of the mixture, in order to achieve and maintain the emulsion. Typically, the phases are homogenized (i.e., emulsified) by operating the mixer, e.g., homogenizer, at a speed sufficient to form an emulsion. In one example, the homogenizer is operated at a speed of between at or about 1000 and at or about 1500 rpm. Mixing typically is continued until the phases are combined, typically in an emulsion.

f. Cooling

The emulsion can be cooled during and/or after mixing to promote stability and emulsification, for example, by preventing or minimizing oxidization. The cooling can be rapid cooling and can be performed using one or more cooling apparatuses, for example, any of the cooling apparatuses described herein or any cooling apparatus known to those of skill in the art. Suitable cooling apparatuses for use with the methods include recirculating coolers and water and ice baths. An exemplary cooling apparatus is a recirculating cooler, such as those sold by Turmoil (Model No. OC-1000 RO; West Swanzey, N.H.). When the cooling apparatus is a recirculating cooler, fluid from the vessel containing the combined oil and polar phases is circulated through the cooler, typically while mixing, and then back to the vessel, to rapidly cool and maintain the temperature of the mixture during mixing. Typically, the phases are mixed and cooled until the phases are emulsified and the temperature of the emulsification reaches between at or about 25° C. and at or about 43° C., typically between at or about 30° C. and at or about 35° C. For example, the emulsification can be cooled to a temperature of at or about 25° C., 26° C., 27° C., 28° C., 29° C., 30° C., 31° C., 32° C., 33° C., 34° C., 35° C., 36° C., 37° C., 38° C., 39° C., 40° C., 41° C., 42° C. or 43° C. Typically, when the cooling is rapid cooling, the temperature can be reached in less than or about 2 hours, typically less than or about 1 hour. For example, the emulsification can be cooled to the desired temperature, e.g., between at or about 25° C. and at or about 43° C., in at or about 30 minutes to at or about 60 minutes, such as in at or about 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60 minutes.

Cooling can be performed before or after additional steps, such as adding additional ingredients and/or evaluation of the product. In one example, the cooling is carried out after the addition of additional ingredients, for example, taste-modifying agents, and/or pH adjusting agents.

g. Spray Drying

After combining the oil phase and polar phase to form the emulsion, the emulsion can be dried into a powder. An exemplary method of drying includes spray drying. In the methods provided herein, the powder formed is a free-flowing, i.e., not sticky, powder. Free-flowing powders can be obtained using techniques well known in the art, such as, but not limited to, spray drying, freeze drying or absorption plating. Typically, the emulsion is dried, for example, spray dried, into a powder after the emulsion has been cooled to a desired temperature, e.g., between or between about 25° C. and 43° C., such as at or about 30° C.

The methods for forming the powders include spray drying. Spray drying processes and spray drying equipment are described generally in Perry's Chemical Engineers' Handbook, pp. 20-57 (Sixth Edition 1984). More details on spray drying processes and equipment are reviewed by Marshall (1954) "Atomization and Spray-Drying," Chem. Eng. Prog. Monogr. 50: Series 2 and Masters, "Spray Drying Handbook" (Fourth Edition 1985). Methods for spray drying are well known (see, e.g., U.S. Pat. Nos. 5,430,021 and 6,534,085 and U.S. Publication No. 2007/0184117). In general, spray drying is used to dry a heated liquid by passing it through hot gas. One or more spray nozzles is used to atomize the liquid in a cooling tower or chamber. As the material is atomized (sprayed), the surface tension causes a uniform spherical particle to form, which is passed through the cooling chamber and hardens into a solid intact sphere. The spray dried particles can be between at or about 0.5 microns and at or about 100 microns, and typically are less than at or about 10 microns, typically less than at or about 5 microns, and typically less than at or about, or at or about, 1 micron.

Exemplary of a spray dryer is a cyclone spray dryer. During spray drying with a cyclone spray dryer, the homogenized mixture is pumped into an atomizing device where it is broken into small droplets. Upon contact with a stream of hot air, the moisture is removed very rapidly from the droplets while still suspended in the drying air. The dry powder is separated from the moist air in cyclones by centrifugal action. The centrifugal action is caused by the great increase in air speed when the mixture of particles and air enters the cyclone system. The dense powder particles are forced toward the cyclone walls while the lighter, moist air is directed away through the exhaust pipes. The powder settles to the bottom of the cyclone where it is removed through a discharging device. Sometimes the air-conveying ducts for the dry powder are connected with cooling systems which admit cold air for transport of the product through conveying pipes. Cyclone dryers have been designed for large production schedules capable of drying ton-lots of powder per hour.

The methods provided herein produce powders using a standard spray dryer. The liquid to be dried, for example a solution, suspension or emulsion, may be fed into an atomizer to generate the powder. The atomizer may be, for example, a rotary (wheel) atomizer or nozzle atomizer. In some examples, a fluid bed dryer may also be used. The atomizer is typically an open-mode design with single-point powder discharge, an open-mode design with dual-point powder discharge, or a closed-cycle design with single-point powder discharge, or an alternative form of atomizer. In some examples, the atomizer is contained within a dryer consisting of a feed pump to funnel in the liquid, for example the emulsion, an atomizer, an air heater, an air dispenser, a drying chamber, systems for powder recovery, and process control systems.

In order to prepare the dry powder using a spray drier, the liquid, e.g., emulsion, is fed into a rotary wheel or high pressure nozzle atomizer at a uniform rate, and thereby converted into a spray of droplets. The pattern of the resultant droplets may be largely dependent on the properties of the liquid to be spray dried, including its bulk density, in conjunction with the speed and configuration of the atomizer wheel. In desirable conditions, rotation of the atomizer wheel occurs with minimal vibration, at high peripheral speeds and with smooth internal surfaces, for maximum efficacy. The optimum speed and wheel configuration for a specific liquid can be determined empirically by one of skill in the art. In some examples, the spray of droplets contacts the hot air, for example air at a temperature of about or 160° C. or about or 280° C., present in the drying chamber, triggering the formation of dry particles and cooling of the hot air due to the evaporation of water or chemical solvent from the concentrated liquid sample. The resultant powder and cooler, humid air are separately, and continuously, discharged from the chamber. In some examples, the dry powder is cooled and bagged after separation from the cooler, humid air. After powder recovery, some powders are rewet by re-dissolving the powder in water or a solvent and the composition is subject to a second round of spray drying and collection. In some examples the powders are then sifted, for example through a 60-80 μm mesh screen.

As will be appreciated by one of skill in the art, the inlet temperature and the outlet temperature of the spray drier are not critical but will be of such a level to provide the desired particle size, of less than at or about 1 micron, and to result in a powder that has a desired property. The inlet and outlet temperatures can be adjusted depending on the melting characteristics and composition of the emulsion. The inlet temperature typically is between at or about 60° C. and at or about 170° C. with outlet temperatures between at or about 40° C. to at or about 120° C. Typical inlet temperatures are from at or about 90° C. to at or about 120° C. and typical outlet temperatures are from at or about 60° C. to at or about 90° C. The flow rate which is used in the spray drying equipment will generally be at or about 3 mL per minute to at or about 15 mL per minute. The atomizer air flow rate will vary between values of at or about 25 L per minute to at or about 50 L per minute. Commercially available spray dryers are well known to those of skill in the art, and suitable settings for any particular dispersion can be readily determined by one of skill in the art without undue experimentation. Operating conditions such as inlet temperature and outlet temperature, feed rate, atomization pressure, flow rate of the drying air, and nozzle configuration can be adjusted in accordance with the manufacturer's guidelines.

In some examples, a processing aid, such as additional solvent, for example, water, is added to the emulsion. The processing aid, e.g., water, allows the emulsion to pass through the pump of the dryer more easily, for example, by making the emulsion less thick. The processing aid, for example, water, is evaporated during the drying process and is not present in the final dry powder.

In some examples, the dry powder is stored into a capsule form or is pressed into a tablet. For use as tablets, the compositions typically contain multiple other excipients. These excipients include tablet disintegrants, such as corn starch, glidants, such as silicon dioxide, and lubricants such as magnesium stearate. Ordinarily these compositions contain minor amounts by weight of glidants and lubricants, e.g., each two percent (2%) or less by weight. Tablet disintegrants are optionally present and, if present, are included in sufficient amounts to assure that the tablet disintegrates upon ingestion. For example, disintegrants, such as corn starch, can be employed at concentrations of from about zero to about 30 percent by weight of the composition.

Free flowing, i.e., not sticky, powders also can be used to administer the non-polar ingredients by inhalation using a dry powder inhaler (DPI). Such dry powder inhalers typically administer the ingredient as a free-flowing powder that is dispersed in the air-stream during inspiration. In order to achieve a free flowing powder, the ingredients are typically formulated with a suitable excipient such as lactose or starch. For example, such a dry powder formulation can be made, for example, by combining the lactose with the active agent and then dry blending the components. Alternatively, if desired, the active agent can be formulated without an excipient. The pharmaceutical composition is then typically loaded into a dry powder dispenser, or into inhalation cartridges or capsules for use with a dry powder delivery device. Examples of dry powder inhaler delivery devices include those sold under the trademarks Diskhaler® (GlaxoSmithKline, Research Triangle Park, NC) (see, e.g., U.S. Pat. No. 5,035,237); Diskus® (GlaxoSmithKline) (see, e.g., U.S. Pat. No. 6,378,519; Turbuhaler® (AstraZeneca, Wilmington, Del.) (see, e.g., U.S. Pat. No. 4,524,769); Rotahaler® (GlaxoSmithKline) (see, e.g., U.S. Pat. No. 4,353,365) and HandiHaler® (Boehringer Ingelheim). Further examples of suitable DPI devices are described in U.S. Pat. Nos. 5,415,162; 5,239,993; and 5,715,810 and references cited therein.

h. Filtration, Additions, Evaluation and Packaging

After combining the oil and polar phases to form a mixture, i.e., emulsion, or after drying the emulsion to form a dry powder, one or more additional steps can be carried out to modify, evaluate, analyze and/or package the product. Typically, taste-modifying agents are added to the emulsion, such as flavoring agents (e.g., flavoring agents that confer fruit flavors, such as peach, or other flavors, such as pina colada) and sweetening agents (e.g., sucralose). Other ingredients can be added, such as masking agents (e.g., NAT masking agent) and pH adjusting agents (e.g., acids, such as, but not limited to citric acid). The pH adjusting agent can be used to adjust the pH of the emulsion, for example, to a neutral pH, typically between about 7 and 8.

Before and/or after adding additional ingredients, the product can be evaluated, such as by measuring the pH and/or the temperature. Measurements can be taken using an instrument such as those described herein. In one example, additional ingredients (e.g., pH adjusters) are added based on information obtained by evaluating the product. The product can be analyzed and evaluated to verify and/or determine other properties of the product, for example, to verify that the product contains the appropriate amounts of the non-polar ingredients and other ingredients. For example, the products can be evaluated to verify the concentration of probiotic, and to confirm that heavy metal (e.g., arsenic, cadmium, mercury, lead and others) levels are within the acceptable range according to food and beverage standards. In another example, the acceptable heavy metal levels are not more than 10 ppm heavy metals and not more than 0.2 ppm lead and 2 ppm arsenic. When a standard exists for a particular amount and/or property, the amount/property is verified by tests in accordance with U.S. Pharmacopeia (USP) and/or AOAC (Association of Analytical Communities) standards. Samples can be analyzed in accordance with these standards by sending a sample of the product to a commercial testing facility, such as Eurofins U.S. (Des Moines, Iowa) or Advanced Botanical Consulting & Testing, Inc. (Tustin, Calif.), or any other facility that performs tests in accordance with these standards.

For example, the amount of fatty acids can be verified according to AOAC standards, for example, by gas chromatography (GC), gas liquid chromatography (GLC) or other fatty acid profiling methods. The levels of heavy metals, such as lead and arsenic, are tested using inductively coupled plasma mass spectrometry (ICP-MS), or by sending a sample of the composition for testing to a testing facility, such as Eurofins U.S. (Des Moines, Iowa) or Advanced Botanical Consulting & Testing, Inc. (Tustin, Calif.), or any other facility capable of performing such tests. Additionally, Fourier transform infrared spectroscopy (FTIR) typically is used to obtain a fingerprint of the product, to verify that no other compounds except the desired ingredients are present in the product.

The emulsifications can be purified, for example, filtered, prior to use or drying, using any of purification device described herein or any other suitable purification device. Water can be added in the case of evaporation, to bring the product up to the appropriate volume. HPLC, GC, GLC, FTIR and ICP-MS can be performed according to well-known methods (see, for example, Analytical Chemistry: An Introduction, 6th Ed., Douglas A. Skoog et al. (1994) Chapters 22 (FTIR) and 27 (GC/GLC, HPLC) and U.S. Pat. No. 6,265,717 (ICP-MS)).

After evaluation, purification, and/or addition of all the ingredients, the product, e.g., emulsion or dry powder, can be packaged, for example, into large containers for storage or into smaller containers for administration, such as bottles or ampoules, syringes and packets. The products can be transferred to the packaging containers using a transfer device, such as a transfer device described herein, including transfer pumps and fittings as described above or by manual transfer. For example, the product can be packaged for storage in containers, such as totes, e.g., 275 gallon totes (such as the 275 gallon bottle with a reconditioned CageTote tank IBC, Item No. REN275; Qualserv Enterprises, Inc. (www.qualservcontainer.com)), by transferring the mixture using a food grade hose (e.g. Sani-Tech® STHT®-R-HD braid-reinforced heavy duty silicone hose; sold by Sani-Tech® West, Inc.). After transfer, the tote can be closed and sealed, e.g., tied, such as with a cable tie. Sealed containers can contain nitrogen to replace air.

i. Cleaning the Equipment

The equipment used in the provided methods can be cleaned prior to and/or after use, such as in a sink and/or rinsing the vessels, e.g., tanks, and hose lines. The tanks can be cleaned by filling with hot water, washing with soap and water, and rinsing with water. The pH of the water can be checked before discharging the water from the vessel. The water can be adjusted to the desired pH, for example to a pH between 6 and 9, by adding a pH adjusting agent, such as soda ash, citric acid and/or $H_3PO_4$. After discharging the water from the vessel, the tanks can be sanitized, such as with isopropyl alcohol (IPA), and let dry.

E. METHODS OF USE

Typically, the compositions are provided for administration to humans and animals in unit or multiple dosage forms. Each unit-dose contains a predetermined quantity of the agent to be delivered sufficient to produce the desired effect, in association with the required additives in the composition. Unit-dose forms can be administered in fractions or multiples thereof. Examples of unit dosage include capsules filled with liquid compositions. A multiple-dose form is a plurality of identical unit-dosage forms packaged in a single container to be administered in segregated unit-dose form. Examples of multiple-dose forms include vials and bottles. The powders can be diluted into a suitable beverage for oral ingestion. The emulsions can be directly ingested. The powders or emulsions can be provided in capsules, the powders can be formed into tablets.

F. ARTICLES OF MANUFACTURE

The compositions provided herein can be packaged as articles of manufacture containing packaging material, a composition provided herein, and a label that indicates the manner in which the composition is used In certain embodiments, the compositions can be packaged as articles of manufacture containing packaging material, a composition provided herein suitable for mucosal administration, and a label that indicates that the composition is used for delivery of dietary supplements. In certain embodiments, the compositions can be packaged as articles of manufacture containing packaging material, a composition provided herein suitable for mucosal administration, and a label that indicates that the composition is used for delivering a therapeutic agent to a subject in need thereof.

The articles of manufacture provided herein contain packaging materials. Packaging materials for use in packaging pharmaceutical products are well known to those of skill in the art. See, e.g., U.S. Pat. Nos. 5,323,907; 5,052,558 and 5,033,252. Examples of pharmaceutical packaging materials include, but are not limited to, blister packs, bottles, tubes, inhalers, pumps, bags, vials, containers, bottles, and any packaging material suitable for a selected formulation and intended mode of administration and treatment.

The following examples are exemplary only and are not intended to limit the scope of the subject matter claimed herein.

G. EXAMPLES

Example 1

Preparation of Dry Powder Containing *Bifidobacterium Longum* and MCT Oil

Appropriate quantities of the raw materials were weighed for the 300 g batch as shown below:

| Ingredient | %/serving before evaporation | g/batch | %/serving after evaporation |
|---|---|---|---|
| Water | 57.500 | 172.5 | 0.00 |
| KHCO₃ | 3.333 | 10 | 7.84 |
| Cluster Dextrin | 6.367 | 19.1 | 14.98 |
| SFAE | 4.250 | 12.75 | 10.00 |
| Saladizer ® emulsifier | 0.067 | 0.2 | 0.16 |
| Lactoferrin | 6.187 | 18.56 | 14.56 |
| BL-05 *Bifidobacterium Longum* 80-100B per g | 4.667 | 14 | 10.98 |
| MCT Oil | 17.630 | 52.89 | 41.48 |
| Totals | 100.000 | 300.0 | 100.00 |

The polar phase was prepared by weighing the appropriate amounts of water, Saladizer® emulsifier, Cluster Dextrin, SFAE and KHCO3 and then mixing at a temperature of approximately 50° C.

The oil phase was prepared by weighing the appropriate amounts of MCT oil, *Bifidobacterium Longum* (Jarrow) and lactoferrin. Then, *Bifidobacterium Longum* and lactoferrin were mixed into the MCT oil at a temperature of approximately 40° C.

The emulsion was prepared by adding the oil phase to the polar phase, slowly while mixing at low to medium (1000-15000 RPM) using an Arde Barinco Mixer Type 74D (Serial No. L-1274) until the mixture is homogeneous, or approximately 5 minutes. The emulsion was allowed to cool in a cooler with mixing to 30° C.

The emulsions were then spray dried into dry powders. The dry powder was prepared using a standard spray dryer equipped with a rotary atomizer nozzle or a standard spray nozzle. Alternatively, a fluid bed dryer or box dryer can be used. The emulsion was added to a tank and mixed with a mixer when necessary to keep the liquid homogenous during the spray drying process. The liquid was then pumped to the top of the spray dryer (GEA Niro, Denmark) and sprayed through a nozzle atomizer into the spray dryer, typically kept at a temperature of 160° C., or up to approximately 280° C. When the spray dryer was equipped with a fluid bed, the liquid was sprayed through a rotary atomizer at lower temperatures into the spray dryer. Water then evaporated and pooled at the top of the dryer, while the powder collected at the floor bottom of the dryer, where it was recovered. After recovering the powder, some powders were rewet or instantized by redissolving the dry powder in water at a 1:3 or 1:1 powder to water ratio (e.g., 30-50 g powder was dissolved in 100 g of water) and spray drying a second time. The powders were then sifted/filtered using a 60-80 micron mesh screen.

Some emulsions required the addition of extra water (i.e., evaporation water) as a processing aid to make the emulsion thinner and able to pass through the dryer pump more easily. The extra water was added to the emulsion at 35° C. and was evaporated during the spray dry process, along with the rest of the water in the emulsion. The resulting powder was cooled to 35° C. and packaged into appropriate containers.

Example 2

Preparation of Dry Powder Containing *Bifidobacteria Infantis* and MCT Oil

Appropriate quantities of the raw materials were weighed for the 500 g batch as shown below:

| Ingredient | %/serving before evaporation | g/batch | %/serving after evaporation |
|---|---|---|---|
| Water | 57.500 | 287.5 | 0.00 |
| KHCO3 | 3.333 | 16.667 | 7.84 |
| Cluster Dextrin | 6.367 | 31.833 | 14.98 |
| SFAE | 4.250 | 21.25 | 10.00 |
| Saladizer ® emulsifier | 0.067 | 0.333 | 0.16 |
| Lactoferrin | 6.187 | 30.9333 | 14.56 |
| *Bifidobacteria Infantis* | 4.667 | 23.3333 | 10.98 |
| MCT Oil | 17.630 | 88.15 | 41.48 |
| Totals | 100.000 | 500.000 | 100.00 |

The polar phase was prepared by weighing the appropriate amounts of water, Saladizer® emulsifier, Cluster Dextrin, SFAE and KHCO3 and then mixing at a temperature of approximately 50° C.

The oil phase was prepared by weighing the appropriate amounts of MCT oil, *Bifidobacteria Infantis* (Danisco) and lactoferrin. Then, *Bifidobacteria Infantis* and lactoferrin were mixed into the MCT oil at a temperature of approximately 40° C.

The emulsion was prepared by adding the oil phase to the polar phase slowly while mixing at low to medium (1000-15000 RPM) using an Arde Barinco Mixer Type 74D (Serial No. L-1274) until the mixture is homogeneous, or approximately 5 minutes. The emulsion was allowed to cool in a cooler with mixing to 30° C.

The emulsions were then spray dried into dry powders. The dry powder was prepared using a standard spray dryer equipped with a rotary atomizer nozzle or a standard spray nozzle. Alternatively, a fluid bed dryer or box dryer can be used. The emulsion was added to a tank and mixed with a mixer when necessary to keep the liquid homogenous during the spray drying process. The liquid was then pumped to the top of the spray dryer (GEA Niro, Denmark) and sprayed through a nozzle atomizer into the spray dryer, typically kept at a temperature no more than 160° C., or up to approximately 280° C. When the spray dryer was equipped with a fluid bed, the liquid was sprayed through a rotary atomizer at lower temperatures into the spray dryer. Water then evaporated and pooled at the top of the dryer, while the powder collected at the floor bottom of the dryer, where it was recovered. After recovering the powder, some powders were rewet or instantized by redissolving the dry powder in water at a 1:3 or 1:1 powder to water ratio (e.g., 30-50 g powder was dissolved in 100 g of water) and spray drying a second time. The powders were then sifted/filtered using a 60-80 micron mesh screen.

Some emulsions required the addition of extra water (i.e., evaporation water) as a processing aid to make the emulsion thinner and able to pass through the dryer pump more easily. The extra water was added to the emulsion at 35° C. and was evaporated during the spray dry process, along with the rest of the water in the emulsion. The resulting powder was cooled to 35° C. and packaged into appropriate containers.

Example 3

Preparation of Dry Powder Containing *Bifidobacteria Lactis* and MCT Oil

Appropriate quantities of the raw materials were weighed for the 500 g batch as shown below:

| Ingredient | %/serving before evaporation | g/batch | %/serving after evaporation |
|---|---|---|---|
| Water | 57.500 | 287.5 | 0.00 |
| KHCO3 | 3.333 | 16.667 | 7.84 |
| Cluster Dextrin | 6.367 | 31.833 | 14.98 |
| SFAE | 4.250 | 21.25 | 10.00 |
| Saladizer ® emulsifier | 0.067 | 0.333 | 0.16 |
| Lactoferrin | 6.187 | 30.9333 | 14.56 |
| BL-04-500B *Bifidobacteria lactis* | 4.667 | 23.3333 | 10.98 |
| MCT Oil | 17.630 | 88.15 | 41.48 |
| Totals | 100.000 | 500.000 | 100.00 |

The polar phase was prepared by weighing the appropriate amounts of water, Saladizer® emulsifier, Cluster Dextrin, SFAE and KHCO3 and then mixing at a temperature of approximately 50° C.

The oil phase was prepared by weighing the appropriate amounts of MCT oil, *Bifidobacteria Lactis* (Danisco) and lactoferrin. Then, *Bifidobacteria Lactis* and lactoferrin were mixed into the MCT oil at a temperature of approximately 40° C.

The emulsion was prepared by adding the oil phase to the polar phase slowly while mixing at low to medium (1000-15000 RPM) using an Arde Barinco Mixer Type 74D (Serial No. L-1274) until the mixture is homogeneous, or approximately 5 minutes. The emulsion was allowed to cool in a cooler with mixing to 30° C.

The emulsions were then spray dried into dry powders. The dry powder was prepared using a standard spray dryer equipped with a rotary atomizer nozzle or a standard spray nozzle. Alternatively, a fluid bed dryer or box dryer can be used. The emulsion was added to a tank and mixed with a mixer when necessary to keep the liquid homogenous during the spray drying process. The liquid was then pumped to the top of the spray dryer (GEA Niro, Denmark) and sprayed through a nozzle atomizer into the spray dryer, typically kept at a temperature no more than 160° C., or up to approximately 280° C. When the spray dryer was equipped with a fluid bed, the liquid was sprayed through a rotary atomizer at lower temperatures into the spray dryer. Water then evaporated and pooled at the top of the dryer, while the powder collected at the floor bottom of the dryer, where it was recovered. After recovering the powder, some powders were rewet or instantized by redissolving the dry powder in water at a 1:3 or 1:1 powder to water ratio (e.g., 30-50 g powder was dissolved in 100 g of water) and spray drying a second time. The powders were then sifted/filtered using a 60-80 micron mesh screen.

Some emulsions required the addition of extra water (i.e., evaporation water) as a processing aid to make the emulsion thinner and able to pass through the dryer pump more easily. The extra water was added to the emulsion at 35° C. and was evaporated during the spray dry process, along with the rest of the water in the emulsion. The resulting powder was cooled to 35° C. and packaged into appropriate containers.

Example 4

Preparation of Dry Powder Containing *Lactobacillus acidophilus* and MCT Oil

Appropriate quantities of the raw materials were weighed for the 500 g batch as shown below:

| Ingredient | %/serving before evaporation | g/batch | %/serving after evaporation |
|---|---|---|---|
| Water | 57.500 | 287.5 | 0.00 |
| KHCO3 | 3.333 | 16.667 | 7.84 |
| Cluster Dextrin | 6.367 | 31.833 | 14.98 |
| SFAE | 4.250 | 21.25 | 10.00 |
| Saladizer ® emulsifier | 0.067 | 0.333 | 0.16 |
| Lactoferrin | 6.187 | 30.9333 | 14.56 |
| LA-14 Lactobacillus acidophilus | 4.667 | 23.3333 | 10.98 |
| MCT Oil | 17.630 | 88.15 | 41.48 |
| Totals | 100.000 | 500.000 | 100.00 |

The polar phase was prepared by weighing the appropriate amounts of water, Saladizer® emulsifier, Cluster Dextrin, SFAE and KHCO3 and then mixing at a temperature of approximately 50° C.

The oil phase was prepared by weighing the appropriate amounts of MCT oil, *Lactobacillus acidophilus* (Danisco) and lactoferrin. Then, *Lactobacillus acidophilus* and lactoferrin were mixed into the MCT oil at a temperature of approximately 40° C.

The emulsion was prepared by adding the oil phase to the polar phase slowly while mixing at low to medium (1000-15000 RPM) using an Arde Barinco Mixer Type 74D (Serial No. L-1274) until the mixture is homogeneous, or approximately 5 minutes. The emulsion was allowed to cool in a cooler with mixing to 30° C.

The emulsions were then spray dried into dry powders. The dry powder was prepared using a standard spray dryer equipped with a rotary atomizer nozzle or a standard spray nozzle. Alternatively, a fluid bed dryer or box dryer can be used. The emulsion was added to a tank and mixed with a mixer when necessary to keep the liquid homogenous during the spray drying process. The liquid was then pumped to the top of the spray dryer (GEA Niro, Denmark) and sprayed through a nozzle atomizer into the spray dryer, typically kept at a temperature no more than 160° C., or up to approximately 280° C. When the spray dryer was equipped with a fluid bed, the liquid was sprayed through a rotary atomizer at lower temperatures into the spray dryer. Water then evaporated and pooled at the top of the dryer, while the powder collected at the floor bottom of the dryer, where it was recovered. After recovering the powder, some powders were rewet or instantized by redissolving the dry powder in water at a 1:3 or 1:1 powder to water ratio (e.g., 30-50 g powder was dissolved in 100 g of water) and spray drying a second time. The powders were then sifted/filtered using a 60-80 micron mesh screen.

Some emulsions required the addition of extra water (i.e., evaporation water) as a processing aid to make the emulsion thinner and able to pass through the dryer pump more easily. The extra water was added to the emulsion at 35° C. and was evaporated during the spray dry process, along with the rest of the water in the emulsion. The resulting powder was cooled to 35° C. and packaged into appropriate containers.

Example 5

Preparation of Dry Powder Containing Probio-Tec® *Lactobacillus rhamnosus* GG sold under the trademark LGG®) and MCT Oil

| Ingredient | %/serving before evaporation | g/batch | %/serving after evaporation |
|---|---|---|---|
| Water | 57.500 | 345 | 0.00 |
| KHCO3 | 3.333 | 20 | 7.84 |
| Cluster Dextrin | 6.367 | 38.2 | 14.98 |
| SFAE | 4.250 | 25.5 | 10.00 |
| Saladizer ® emulsifier | 0.067 | 0.4 | 0.16 |
| Lactoferrin | 6.187 | 37.12 | 14.56 |
| *Lactobacillus rhamnosus* GG (sold under the trademark Probio-Tec ® LGG ®) | 4.667 | 28 | 10.98 |
| MCT Oil | 17.630 | 105.78 | 41.48 |
| Totals | 100.000 | 600.0000 | 100.00 |

The polar phase was prepared by weighing the appropriate amounts of water, Saladizer® emulsifier, Cluster Dextrin, SFAE and KHCO3 and then mixing at a temperature of approximately 50° C.

The oil phase was prepared by weighing the appropriate amounts of MCT oil, *Lactobacillus rhamnosus* GG (sold under the trademark Probio-Tec® LGG®) and lactoferrin. Then, *Lactobacillus rhamnosus* GG (sold under the trademark Probio-Tec® LGG®) and lactoferrin were mixed into the MCT oil at a temperature of approximately 40° C.

The emulsion was prepared by adding the oil phase to the polar phase, slowly while mixing at low to medium (1000-15000 RPM) using an Arde Barinco Mixer Type 74D (Serial No. L-1274) until the mixture is homogeneous, or approximately 5 minutes. The emulsion was allowed to cool in a cooler with mixing to 30° C.

The emulsions were then spray dried into dry powders. The dry powder was prepared using a standard spray dryer equipped with a rotary atomizer nozzle or a standard spray nozzle. Alternatively, a fluid bed dryer or box dryer can be used. The emulsion was added to a tank and mixed with a mixer when necessary to keep the liquid homogenous during the spray drying process. The liquid was then pumped to the top of the spray dryer (GEA Niro, Denmark) and sprayed through a nozzle atomizer into the spray dryer, typically kept at a temperature no more than 160° C., or up to approximately 280° C. When the spray dryer was equipped with a fluid bed, the liquid was sprayed through a rotary atomizer at lower temperatures into the spray dryer. Water then evaporated and pooled at the top of the dryer, while the powder collected at the floor bottom of the dryer, where it was recovered. After recovering the powder, some powders were rewet or instantized by redissolving the dry powder in water at a 1:3 or 1:1 powder to water ratio (e.g., 30-50 g powder was dissolved in 100 g of water) and spray drying a second time. The powders were then sifted/filtered using a 60-80 micron mesh screen.

Some emulsions required the addition of extra water (i.e., evaporation water) as a processing aid to make the emulsion thinner and able to pass through the dryer pump more easily. The extra water was added to the emulsion at 35° C. and was evaporated during the spray dry process, along with the rest of the water in the emulsion. The resulting powder was cooled to 35° C. and packaged into appropriate containers.

Example 6

Stability of Probio-Tec® *Lactobacillus rhamnosus* GG (Sold Under the Trademark LGG®) in MCT Emulsion and Dry Powder To assess the stability of the resulting emulsion and powder, the initial amount and the amount after 2 weeks accelerated testing of *Lactobacillus rhamnosus* GG (LGG®) was assessed by Innovatical Laboratories, LLC in accordance with International Conference on Harmonization (ICH) guidelines for Stability Testing of a Dietary Supplement Product. Normal conditions consist of 25±2° C./65%±5% Relative Humidity (RH) and accelerated conditions were conducted at 40±2° C./75%±5% RH. The environment chamber used for the following experiments was Model PRA-1AP, Serial number 2980 made by Tabai Espec Corp. 12 weeks of monitoring at accelerated conditions can be extrapolated to 2 years of room temperature condition based on ICH stability guidelines. Two weeks at accelerated conditions is equivalent to 4 months at normal conditions. Four weeks at accelerated conditions is equivalent to 8 months at normal conditions. Six weeks at accelerated conditions is equivalent to 1 year at normal conditions. The results of each test were compiled of at least 3 batches of testing. The *Lactobacillus rhamnosus* GG (LGG®) was stable in both the emulsion and powder form after 6 weeks accelerated treatment, which extrapolates to 1 year under normal conditions. The results are set forth in the table below:

|  | T = 0 | T = 2 weeks (accelerated) | T = 4 weeks (accelerated) | T = 6 weeks (accelerated) |
| --- | --- | --- | --- | --- |
| Emulsion | $3.70 \times 10^{10}$ CFU/mL | $4.00 \times 10^{10}$ CFU/ml | $5.0 \times 10^{10}$ CFU/g | $4.00 \times 10^{10}$ CFU/ml |
| Powder | $5.2 \times 10^{10}$ CFU/g | $5.0 \times 10^{10}$ CFU/g | $6.0 \times 10^{10}$ CFU/g | $5.0 \times 10^{10}$ CFU/g |

Example 7

Stability of *Bifidobacteria Infantis, Lactobacillus Rhamnosus* GG (LGG®), *Bifidobacterium Lactis* and *Lactobacillus Acidophilus* in MCT Emulsion To assess the stability of the resulting emulsion, the amount of probiotic present in the emulsion after 3 months under normal conditions was assessed by Innovatical Laboratories, LLC using the ICH test method detailed in Example 11. The probiotics were stable in emulsion form after 3 months under normal conditions. The results are set forth in the table below:

|  | specification | result |
| --- | --- | --- |
| *Bifidobacteria Infantis,* | 4 Billion cfu/15 g | 6 Billion cfu/15 g |
| *Lactobacillus rhamnosus* GG (LGG ®) | 40 Billion cfu/15 g | 70.5 Billion cfu/15 g |
| *Bifidobacterium Lactis* | 40 Billion cfu/15 g | 70.5 Billion cfu/15 g |
| *Lactobacillus Acidophilus* | 16 Billion cfu/15 g | 15 Billion cfu/15 g |
| *Bifidobacterium Longum* | 8 Billion cfu/g | 10 Billion cfu/g |

Example 8

Compositions of MCT Emulsions Containing *Bifidobacteria Infantis, Bifidobacterium Lactis, Bifobacterium Longum, Lactobacillus Acidophilus* and *Lactobacillus rhamnosus* GG (LGG®)

The amounts of probiotics and various components in the resulting emulsions were assessed. The results are set forth in the table below:

|  | CFU/1 mL | Heavy metals (ppm) | Lead (ppm) | Arsenic (ppm) | Mercury (ppm) | Cadmium (ppm) |
| --- | --- | --- | --- | --- | --- | --- |
| *Bifidobacteria Infantis,* | 5 billion | 10 | 0.12 | 2.4 | 0.07 | 1 |
| *Bifidobacterium Lactis* | 50 billion | 10 | 0.12 | 2.4 | 0.07 | 1 |
| *Bifidobacterium Longum* | 20 billion | 10 | 0.12 | 2.4 | 0.07 | 1 |
| *Lactobacillus Acidophilus* | 20 billion | 10 | 0.12 | 2.4 | 0.07 | 1 |

-continued

|  | CFU/1 mL | Heavy metals (ppm) | Lead (ppm) | Arsenic (ppm) | Mercury (ppm) | Cadmium (ppm) |
|---|---|---|---|---|---|---|
| *Lactobacillus rhamnosus* GG (LGG®) | 35 billion | 10 | 0.12 | 2.4 | 0.07 | 1 |

Example 9

Powder Compositions Containing *Bifidobacteria Infantis, Bifidobacterium Lactis, Bifobacterium Longum, Lactobacillus Acidophilus* and *Lactobacillus rhamnosus* GG (Sold Under the Trademark LGG®)

The amounts of probiotics and various components in the resulting powders were assessed. The results are set forth in the table below:

|  | CFU/1 mL | Heavy metals (ppm) | Lead (ppm) | Arsenic (ppm) | Mercury (ppm) | Cadmium (ppm) |
|---|---|---|---|---|---|---|
| *Bifidobacteria Infantis* | 5 billion | 10 | 0.12 | 2.4 | 0.07 | 1 |
| *Bifidobacterium Lactis* | 50 billion | 10 | 0.12 | 2.4 | 0.07 | 1 |
| *Bifidobacterium Longum* | 8 billion | 10 | 0.12 | 2.4 | 0.07 | 1 |
| *Lactobacillus Acidophilus* | 20 billion | 10 | 0.12 | 2.4 | 0.07 | 1 |
| *Lactobacillus rhamnosus* GG (LGG®) | 35 billion | 10 | 0.12 | 2.4 | 0.07 | 1 |

Example 10

Stability of Powder and Emulsion Contain *Lactobacillus rhammosus* GG

Emulsions and powders prepared as described herein, containing the probiotic with associated lactoferrin were tested for stability (number of colony forming units) as a function of time. The testing was conducted by a third party Advanced Botanica; Consulting & Testing, Inc. (Tustin, Calif.), in accord with their protocols to assess the viability of the probiotic bacteria in the powders and emulsions. The results indicate that the bacteria are viable in these formulations for at least a year. As data show, the numbers of bacteria remained constant for at least a year. Prior formulations that contain powders or just mixtures that include lactoferrin and probiotic are far less stable. Liquids are stored in refrigerators, and powders have shelf lives of 3 months or less.

Emulsion

| Time | Colony Forming units (CFU)/gram |
|---|---|
| 0 (initial) | $3.7 \times 10^{10}$ |
| 4 months | $4.0 \times 10^{10}$ |
| 8 months | $5.0 \times 10^{10}$ |
| *12 months | $4.0 \times 10^{10}$ |

Powder

| Time | Colony Forming units/gram |
|---|---|
| 0 (initial) | $5.2 \times 10^{10}$ |
| 4 months | $5.0 \times 10^{10}$ |
| 8 months | $6.0 \times 10^{10}$ |
| 12 months | $5.0 \times 10^{10}$ |

Since modifications will be apparent to those of skill in this art, it is intended that this invention be limited only by the scope of the appended claims.

What is claimed is:

1. A powder composition, comprising, by weight % of the composition:
   5%-25% probiotic; and
   5%-25% mucoadhesive protein,
   wherein:
   the total amount of probiotic and mucoadhesive protein is 20%-35%;
   30%-50% ingestible oil;
   5%-15% surfactant other than a vitamin E derivative;
   10%-20% binder; and
   4%-12% stabilizer.

2. The powder composition of claim 1, wherein the mucoadhesive protein is a lactoferrin; the oil is medium chain triglyceride (MCT) oil; the surfactant is a sucrose fatty acid ester; the binder is a dextrin or maltodextrin; and the stabilizer is a carbonate or bicarbonate.

3. A powder composition, comprising:
   5%-15% of sucrose fatty acid ester (SFAE) surfactant;
   5%-20% of dextrin or maltodextrin;
   5%-20% of probiotic;
   5%-20% of mucoadhesive protein; and
   30%-50% of medium chain triglyceride (MCT) oil,
   wherein
   the percentage is by weight.

4. The powder composition of claim 3, wherein:
   the amount of probiotic is 8%-15%, by weight; and
   the amount of mucoadhesive protein is 10%-17%, by weight.

5. A method for supplementing the diet of a subject with a probiotic, comprising administering a composition of claim 1 to the subject.

6. The powder composition of claim 1, wherein the mucoadhesive protein is selected from bovine lactoferrin, human lactoferrin, lactoferrin binding proteins, recombinant human lactoferrin, lactoferricin, lactoferricin b, transferrin binding proteins, bovine transferrin, ovotransferrin, neutrophil granules, apo-lactoferrin, immunoglobulin, albumin and lanthanide-lactoferrin.

7. The powder composition of claim 1, wherein the mucoadhesive protein is a lactoferrin.

8. The powder composition of claim 1, wherein the mucoadhesive protein is from a human or bovine source.

9. The powder composition claim 1, wherein the mucoadhesive protein is human lactoferrin.

10. The powder composition of claim 1, wherein the mucoadhesive protein is a transferrin.

11. The powder composition of claim 3, wherein the mucoadhesive protein is selected from bovine lactoferrin, human lactoferrin, lactoferrin binding proteins, recombinant human lactoferrin, lactoferricin, lactoferricin b, transferrin binding proteins, bovine transferrin, ovotransferrin, neutrophil granules, apo-lactoferrin, immunoglobulin, albumin and lanthanide-lactoferrin.

12. The powder composition of claim 3, wherein the mucoadhesive protein is a lactoferrin.

13. The powder composition of claim 3, wherein the mucoadhesive protein is from a human or bovine source.

14. The powder composition claim 3, wherein the mucoadhesive protein is human lactoferrin.

15. The powder composition of claim 3, wherein the mucoadhesive protein is a transferrin.

16. A method for supplementing the diet of a subject with a probiotic, comprising administering a composition of claim 3 to the subject.

* * * * *